(12) United States Patent
Stockley et al.

(10) Patent No.: US 11,370,784 B2
(45) Date of Patent: Jun. 28, 2022

(54) CYANO-SUBSTITUTED HETEROCYCLES WITH ACTIVITY AS INHIBITORS OF USP30

(71) Applicant: MISSION THERAPEUTICS LIMITED, Cambridge (GB)

(72) Inventors: Martin Lee Stockley, Cambridge (GB); Mark Ian Kemp, Cambridge (GB); Andrew Madin, Cambridge (GB)

(73) Assignee: MISSION THERAPEUTICS LIMITED, Cambridge (GB)

( * ) Notice: Subject to any disclaimer, the term of this patent is extended or adjusted under 35 U.S.C. 154(b) by 486 days.

(21) Appl. No.: 16/336,685

(22) PCT Filed: Oct. 4, 2017

(86) PCT No.: PCT/GB2017/052971
§ 371 (c)(1),
(2) Date: Mar. 26, 2019

(87) PCT Pub. No.: WO2018/065768
PCT Pub. Date: Apr. 12, 2018

(65) Prior Publication Data
US 2021/0284631 A1 Sep. 16, 2021

(30) Foreign Application Priority Data

Oct. 5, 2016 (GB) .................... 1616907
Jun. 28, 2017 (GB) .................... 1710331

(51) Int. Cl.
| | | |
|---|---|---|
| C07D 413/12 | (2006.01) | |
| C07D 265/30 | (2006.01) | |
| C07D 401/12 | (2006.01) | |
| C07D 401/14 | (2006.01) | |
| C07D 413/14 | (2006.01) | |
| C07D 417/12 | (2006.01) | |
| C07D 417/14 | (2006.01) | |
| C07D 471/04 | (2006.01) | |

(52) U.S. Cl.
CPC ......... *C07D 413/12* (2013.01); *C07D 265/30* (2013.01); *C07D 401/12* (2013.01); *C07D 401/14* (2013.01); *C07D 413/14* (2013.01); *C07D 417/12* (2013.01); *C07D 417/14* (2013.01); *C07D 471/04* (2013.01)

(58) Field of Classification Search
None
See application file for complete search history.

(56) References Cited

U.S. PATENT DOCUMENTS

2002/0016337 A1 2/2002 Cuny et al.

FOREIGN PATENT DOCUMENTS

| | | | |
|---|---|---|---|
| EP | 0034471 A1 * | 8/1981 | ............... A61P 9/12 |
| EP | 0034471 A1 | 8/1981 | |
| WO | 0177073 A1 | 10/2001 | |
| WO | 2006110884 A2 | 10/2006 | |
| WO | 2010120854 A1 | 10/2010 | |
| WO | 2016/046530 A1 | 3/2016 | |
| WO | 2016156816 A1 | 10/2016 | |
| WO | 2017/009650 A1 | 1/2017 | |
| WO | 2017/093718 A1 | 6/2017 | |
| WO | 2017/109488 A1 | 6/2017 | |
| WO | 2017103614 A1 | 6/2017 | |
| WO | 2017/141036 A1 | 8/2017 | |
| WO | 2017/149313 A1 | 9/2017 | |
| WO | 2017/158388 A1 | 9/2017 | |
| WO | 2017158381 A2 | 9/2017 | |
| WO | 2017163078 A1 | 9/2017 | |
| WO | 2018060689 A1 | 4/2018 | |
| WO | 2018060691 A1 | 4/2018 | |
| WO | 2018060742 A1 | 4/2018 | |
| WO | 2018220355 A1 | 12/2018 | |
| WO | 2018234775 A2 | 12/2018 | |

OTHER PUBLICATIONS

The International Search Report and Written Opinion, dated Nov. 16, 2017, in the corresponding PCT Appl. No. PCT/GB2017/052971.
Falgueyret et al., "Novel, Nonpeptidic Cyanamides as Potent and Reversible Inhibitors of Human Cathepsins K and L," J. Med. Chem. 2001, 44, 94-104.
Laine et al., "Discovery of Novel Cyanamide-Based Inhibitors of Cathepsin C," ACS Med. Chem. Lett. 2011, 2, 142-147.
Ward et al., "Quantitative Chemical Proteomic Profiling of Ubiquitin Specific Proteases in Intact Cancer Cells," ACS Chem. Biol. 2016, 11, 3268-3272.
Rydzewski et al, "Peptidic 1-Cyanopyrrolidines: Synthesis and SAR of a Series of Potent, Selective Cathepsin Inhibitors", Bioorganic & Medicinal Chemistry 10 (2002) 3277-3284.
Deaton et al, "Novel and potent cyclic cyanamide-based cathepsin K inhibitors", Bioorganic & Medicinal Chemistry Letters 15 (2005) 1815-1819.

(Continued)

*Primary Examiner* — Heidi Reese

(57) ABSTRACT

The present invention relates to cyano-substituted-heterocycles of Formula (I) with activity as inhibitors of deubiquitilating enzymes, in particular, ubiquitin C-terminal hydrolase 30 or ubiquitin specific peptidase 30 (USP30), having utility in a variety of therapeutic areas including cancer and conditions involving mitochondrial dysfunction.

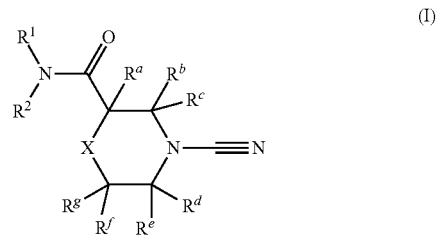

(I)

14 Claims, No Drawings

(56) References Cited

OTHER PUBLICATIONS

Oballa et al, "A generally applicable method for assessing the electrophilicity and reactivity of diverse nitrile-containing compounds", Bioorganic & Medicinal Chemistry Letters 17 (2007) 998-1002.

Zapf et al, "Covalent Inhibitors of Interleukin-2 Inducible T Cell Kinase (Itk) with Nanomolar Potency in a Whole-Blood Assay", J. Med. Chem. 2012, 55, 10047-10063.

Nakamura et al, "Regulation of Mitochondrial Morphology by USP30, a Deubiquitinating Enzyme Present in the Mitochondrial Outer Membrane", Molecular Biology of the Cell, vol. 19, 1903-1911, May 2008.

Bingol et al, "The mitochondrial deubiquitinase USP30 opposes parkin-mediated mitophagy", Nature vol. 510, 370-375, 2014.

Liang et al, "USP30 deubiquitylates mitochondrial Parkin substrates and restricts apoptotic cell death", EMBO Reports, 1-10, 2015; DOI 10.15252/embr.201439820.

Komander et al, "Breaking the chains: structure and function of the deubiquitinases", Nature Reviews Molecular Cell Biology, 10, 550-563, 2009.

Bedford et al., "Ubiquitin-like protein conjugation and the ubiquitin-proteasome system as drug targets", Nature Rev. Drug Discovery, 10:29-46, 2011.

Catalano et al, "Constrained analogues of tocainide as potent skeletal muscle sodium channel blockers towards the development of antimyotonic agents", European Journal of Medicinal Chemistry, 43(11), 2008, 2535-2540.

De Candia Modesta et al, "Investigation of platelet aggregation inhibitory activity by phenyl amides and esters of piperidinecarboxylic acids", Bioorganic and Medicinal Chemistry, 11(7), 2003, 1439-1450.

* cited by examiner

CYANO-SUBSTITUTED HETEROCYCLES WITH ACTIVITY AS INHIBITORS OF USP30

This application is a National Stage Application of PCT/GB2017/052971 filed Oct. 4, 2017, which claims priority from UK Patent Application No. 1616907.0 filed on Oct. 5, 2016 and UK Patent Application No. 1710331.8, filed on Jun. 28, 2017. The priority of said PCT and UK Patent Applications are claimed. Each of the prior mentioned applications is hereby incorporated by reference herein in its entirety.

The present invention relates to a class of cyano-substituted-heterocycles with activity as inhibitors of deubiquitilating enzymes, in particular, ubiquitin C-terminal hydrolase 30 or ubiquitin specific peptidase 30 (USP30), uses thereof, processes for the preparation thereof and composition containing said inhibitors. These inhibitors have utility in a variety of therapeutic areas including cancer and conditions involving mitochondrial dysfunction.

Ubiquitin is a small protein consisting of 76 amino acids that is important for the regulation of protein function in the cell. Ubiquitylation and deubiquitylation are enzymatically mediated processes by which ubiquitin is covalently bound or cleaved from a target protein by deubiquitylating enzymes (DUBs), of which there are approximately 95 DUBs in human cells, divided into sub-families based on sequence homology. The USP family are characterised by their common Cys and His boxes which contain Cys and His residues critical for their DUB activities. The ubiquitylation and deubiquitylation processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis.

Ubiquitin is a master regulator of mitochondrial dynamics. Mitochondria are dynamic organelles whose biogenesis, fusion and fission events are regulated by the post-translational regulation via ubiquitylation of many key factors such as mitofusins. While ubiquitin ligases such as parkin are known to ubiquitylate a number of mitochondrial proteins, until recently, deubiquitylating enzymes remained elusive. USP30 is a 517 amino acid protein which is found in the mitochondrial outer membrane (Nakamura et al., Mol Biol 19:1903-11, 2008). It is the sole deubiquitylating enzyme bearing a mitochondrial addressing signal and has been shown to deubiquitylate a number of mitochondrial proteins. It has been demonstrated that USP30 opposes parkin-mediated mitophagy and that reduction of USP30 activity can rescue parkin-mediated defects in mitophagy.

Mitochondrial dysfunction can be defined as diminished mitochondrial content (mitophagy or mitochondrial biogenesis), as a decrease in mitochondrial activity and oxidative phosphorylation, but also as modulation of reactive oxygen species (ROS) generation. Hence a role for mitochondrial dysfunctions in a very large number of aging processes and pathologies including but not limited to, neurodegenerative diseases (e.g. Parkinson's disease (PD), Alzheimer's disease, Huntington's disease, Amylotrophic Lateral Sclerosis (ALS), multiple sclerosis), cancer, diabetes, metabolic disorders, cardio-vascular diseases, psychiatric diseases (e.g. Schizophrenia), and osteoarthritis.

For example, Parkinson's disease affects around 10 million people worldwide (Parkinson's Disease Foundation) and is characterised by the loss of dopaminergic neurons in the substantia nigra. The exact mechanisms underlying PD are unclear; however mitochondrial dysfunction is increasingly appreciated as a key determinant of dopaminergic neuronal susceptibility in PD and is a feature of both familial and sporadic disease, as well as in toxin-induced Parkinsonism. Parkin is one of a number of proteins that have been implicated with early onset PD. While most PD cases are linked to defects in alpha-synuclein, 10% of Parkinson's cases are linked to specific genetic defects, one of which is in the ubiquitin E3 ligase parkin. Parkin and the protein kinase PTEN-induced putative kinase 1 (PINK1) collaborate to ubiquitylate mitochondrial membrane proteins of damaged mitochondria resulting in mitophagy. Dysregulation of mitophagy results in increased oxidative stress, which has been described as a characteristic of PD. Inhibition of USP30 could therefore be a potential strategy for the treatment of PD. For example, PD patients with parkin mutations leading to reduced activity could be therapeutically compensated by inhibition of USP30.

It has been reported that depletion of USP30 enhances mitophagic clearance of mitochondria and also enhances parkin-induced cell death. USP30 has also been shown to regulate BAX/BAK-dependent apoptosis independently of parkin over expression. Depletion of USP30 sensitises cancer cells to BH-3 mimetics such as ABT-737, without the need for parkin over expression. Thus, an anti-apoptotic role has been demonstrated for USP30 and USP30 is therefore a potential target for anti-cancer therapy.

The ubiquitin-proteasome system has gained interest as a target for the treatment of cancer following the approval of the proteasome inhibitor bortezomib (Velcade®) for the treatment of multiple myeloma. Extended treatment with bortezomib is limited by its associated toxicity and drug resistance. However, therapeutic strategies that target specific aspects of the ubiquitin-proteasome pathway upstream of the proteaseome, such as DUBs, are predicted to be better tolerated (Bedford et al., Nature Rev 10:29-46, 2011).

Accordingly, there is a need for compounds that are inhibitors of USP30 for the treatment of indications where inhibition of USP30 is indicated.

In accordance with a first aspect of the invention there is provided a compound of formula (I):

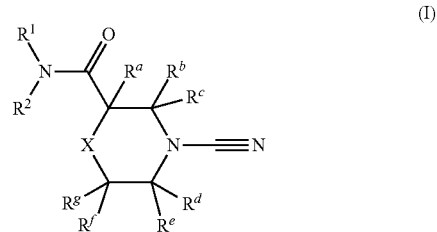

(I)

a tautomer thereof, or a pharmaceutically acceptable salt of said compound or tautomer, wherein:

X is selected from O, N($R^h$), and C($R^i$)($R^j$);

$R^a$ is selected from hydrogen, fluoro, optionally substituted $C_1$-$C_3$ alkyl, and optionally substituted $C_1$-$C_3$ alkoxy; or $R^a$ is linked to $R^b$ or $R^j$ to form an optionally substituted $C_3$-$C_4$ cycloalkyl ring;

$R^b$, $R^c$, $R^d$, and $R^e$, are each independently selected from hydrogen, an optionally substituted $C_1$-$C_3$ alkyl, and one or more spirocyclic groups where $R^b$ is linked to $R^c$ or $R^d$ is linked to $R^e$ to form an optionally substituted $C_3$-$C_4$ cycloalkyl, or $R^b$ is linked to $R^a$ or $R^e$ is linked to $R^f$ to form an optionally substituted $C_3$-$C_4$ cycloalkyl;

$R^f$ and $R^g$ are each independently selected from hydrogen, fluoro, cyano, an optionally substituted $C_1$-$C_3$ alkyl, an optionally substituted $C_1$-$C_3$ alkoxy, and one or more spirocyclic groups where $R^f$ is linked to $R^g$ to form an optionally substituted $C_3$-$C_4$ cycloalkyl ring, or $R^f$ is linked to $R^e$ or $R^g$ is linked to $R^i$ to form an optionally substituted $C_3$-$C_4$ cycloalkyl;

when X is O or $N(R^h)$, neither of $R^a$, $R^f$ or $R^g$, is fluoro or optionally substituted $C_1$-$C_3$ alkoxy;

$R^h$ is selected from hydrogen, optionally substituted $C_1$-$C_3$ alkyl, $C(O)R'$, $S(O)_2R'$, and a 3 to 6 membered heterocyclyl, heteroaryl, cycloalkyl or aryl ring via a $C_0$-$C_3$ alkylene linker;

$R'$ is selected from optionally substituted $C_1$-$C_3$ alkyl, and a 3 to 6 membered heterocyclyl, heteroaryl, cycloalkyl or aryl ring;

$R^i$ and $R^j$ are each independently selected from hydrogen, fluoro, cyano, optionally substituted $C_1$-$C_3$ alkyl, optionally substituted $C_1$-$C_3$ alkoxy, a 3 to 6 membered heterocyclyl, heteroaryl, cycloalkyl or aryl ring, and a spirocyclic group where $R^i$ is linked to $R^j$ or $R^j$ is linked to $R^g$ or $R^a$ to form an optionally substituted $C_3$-$C_4$ cycloalkyl;

$R^1$ is selected from hydrogen and optionally substituted $C_1$-$C_3$ alkyl;

$R^2$ is selected from a 5 to 10 membered, monocyclic or bicyclic, optionally substituted heteroaryl or aryl ring, and a 3 to 10 membered, monocyclic or bicyclic, substituted heterocyclyl or cycloalkyl ring; or $R^1$ and $R^2$ together form a 5 to 10 membered, monocyclic or bicyclic, optionally substituted heteroaryl ring, or a 4 to 10 membered, monocyclic or bicyclic, substituted heterocyclyl ring;

wherein $R^2$, or the ring formed by $R^1$ together with $R^2$, when substituted, is substituted with one or more -$Q^1(R^3)_n$ which may be the same or different, wherein: n is 0 or 1;

$Q^1$ represents $Q^{1a}$ or $Q^{1b}$; wherein $Q^{1a}$ is selected from halo, cyano, nitro, hydroxyl, —$SR^4$, —$NR^4R^5$, —$CONR^4R^5$, —$C_0$-$C_3$-alkylene-$NR^4COR^5$, —$NR^4CONR^5R^6$, —$COR^4$, —$C(O)OR^4$, —$SO_2R^4$, —$SO_2NR^4R^5$, —$NR^4SO_2R^5$, —$NR^4SO_2NR^5R^6$, —$NR^4C(O)OR^5$, optionally substituted —$C_1$-$C_6$ alkyl, optionally substituted $C_1$-$C_6$ alkoxy, and optionally substituted —$C_2$-$C_6$ alkenyl;

$Q^{1b}$ is selected from a covalent bond, an oxygen atom, a sulfur atom, —$OR^7$—, —$SO$—, —$SO_2$—, —$CO$—, —$C(O)O$—, —$C_0$-$C_3$-alkylene-$C(O)NR^4$—$C_0$-$C_3$ alkylene, —$C_0$-$C_3$-alkylene-$NR^4$—$C_0$-$C_3$ alkylene, —$C_0$-$C_3$-alkylene-$NR^4C(O)$—$C_0$-$C_3$ alkylene, —$NR^4CONR^5$—, —$SO_2NR^4$—, $NR^4SO_2$—, —$NR^4SO_2NR^5$—, —$NR^4C(O)O$—, —$NR^4C(O)OR^7$—, optionally substituted $C_1$-$C_6$ alkylene, and optionally substituted —$C_2$-$C_6$ alkenylene;

$R^3$ is a 3 to 10 membered monocyclic or bicyclic heterocyclyl, heteroaryl, cycloalkyl or aryl ring;

$R^4$, $R^5$ and $R^6$ are each independently selected from hydrogen and optionally substituted $C_1$-$C_6$ alkyl;

$R^7$ is optionally substituted $C_1$-$C_6$ alkylene;

wherein $R^3$ is optionally substituted with one or more substituents independently selected from halo, cyano, oxo, nitro, hydroxyl, —$SR^8$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^{2a}$-$R^{11}$, -$Q^{2a}$-O-$Q^{2b}$-$R^{11}$, -$Q^{2a}$-S-$Q^{2b}$-$R^{11}$, -$Q^{2a}$-SO-$Q^{2b}$-$R^{11}$, -$Q^{2a}$-$NR^8CONR^9R^{10}$, -$Q^{2a}$-$NR^8CONR^9$-$Q^{2a}$-$R^{11}$, -$Q^{2a}$-$NR^8R^9$, -$Q^{2a}$-$NR^8$-$Q^{2b}$-$R^{11}$, -$Q^{2a}$-$COR^9$, -$Q^{2a}$-CO-$Q^{2b}$-$R^{11}$, -$Q^{2a}$-$NR^8COR^9$, -$Q^{2a}$-$NR^8CO$-$Q^{2b}$-$R^{11}$, -$Q^{2a}$-$NR^8C(O)OR^9$, -$Q^{2a}$-$NR^8C(O)O$-$Q^{2b}$-$R^{11}$, -$Q^{2a}$-$SO_2R^8$, -$Q^{2a}$-$SO_2$-$Q^{2b}$-$R^{11}$, $Q^{2a}$-$CONR^8R^9$, -$Q^{2a}$-$CONR^8$-$Q^{2b}$-$R^{11}$, -$Q^{2a}$-$CO_2R^8$, -$Q^{2a}$-$CO_2$-$Q^{2b}$-$R^{11}$, -$Q^{2a}$-$SO_2NR^8R^9$, -$Q^{2a}$-$SO_2NR^8$-$Q^{2b}$-$R^{11}$, -$Q^{2a}$-$NR^8SO_2R^9$, -$Q^{2a}$-$NR^8SO_2$-$Q^{2b}$-$R^{11}$, -$Q^{2a}$-$NR^8SO_2NR^9R^{10}$ and -$Q^{2a}$-$NR^8SO_2NR^9$-$Q^{2b}$-$R^{11}$;

wherein $Q^{2a}$ and $Q^{2b}$ each independently represent a covalent bond, optionally substituted $C_1$-$C_6$ alkylene or optionally substituted $C_2$-$C_6$ alkenylene;

$R^8$, $R^9$ and $R^{10}$ are each independently selected from hydrogen and optionally substituted $C_1$-$C_6$ alkyl; and $R^{11}$ is an optionally substituted 3 to 10 membered heterocyclyl, heteroaryl, aryl or cycloalkyl.

Unless otherwise indicated, the term substituted means substituted by one or more defined groups. In the case where groups may be selected from more than one alternatives, the selected groups may be the same or different. The term independently means that where more than one substituent is selected from more than one possible substituents, those substituents may be the same or different.

In the context of the present specification, unless otherwise stated an alkyl, alkylene, alkoxy, alkenyl, alkenylene or alkynyl substituent (or linker) group or an alkyl, alkenyl moiety in a substituent group may be linear or branched. Alkyl, alkylene, alkenyl and alkenylene chains may also include intervening heteroatoms such as oxygen.

"$C_x$-$C_y$ alkyl" refers to a saturated aliphatic hydrocarbon group having x-y carbon atoms which may be linear or branched. For example $C_1$-$C_6$ alkyl contains from 1 to 6 carbon atoms and includes $C_1$, $C_2$, $C_3$, $C_4$, $C_5$ and $C_6$. "Branched" means that at least one carbon branch point is present in the group. For example, tert-butyl and isopropyl are both branched groups. Examples of $C_1$-$C_6$ alkyl groups include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. $C_1$-$C_6$ alkyl and $C_1$-$C_3$ alkyl within the definitions of $R^a$, $R^b$, $R^c$, $R^d$, $R^e$, $R^f$, $R^g$, $R^h$, $R^i$, $R^j$, $R^1$, $R^4$, $R^5$, $R^6$, $R^8$, $R^9$, $R^{10}$, $Q^{1a}$ and within the definition of substituents for $R^3$, may be unsubstituted or substituted with one or more of the substituents defined herein. Examples of substituted $C_1$-$C_6$ alkyl therefore include $CF_3$, $CH_2CF_3$, $CH_2CN$, $CH_2OH$ and $CH_2CH_2OH$.

A "$C_x$-$C_y$ alkylene" group or moiety may be linear or branched and refers to a divalent hydrocarbon group having one less hydrogen atom from $C_x$-$C_y$ alkyl as defined above. $C_1$-$C_6$ alkylene may include intervening heteroatoms such as oxygen, and therefore includes alkyleneoxy groups. Alkyleneoxy as employed herein also extends to embodiments in which the or an oxygen atom (e.g. a single oxygen atom) is located within the alkylene chain, for example $CH_2CH_2OCH_2$ or $CH_2OCH_2$. Examples of $C_1$-$C_6$ alkylene groups include methylene, methyleneoxy, ethylene, ethyleneoxy, n-propylene, n-propyleneoxy, n-butylene, n-butyleneoxy, methylmethylene and dimethylmethylene. Unless stated otherwise, $C_0$-$C_3$ alkylene, $C_1$-$C_6$ alkylene and $C_1$-$C_3$ alkylene within the definitions of $R^h$, $Q^{1a}$, $Q^{1b}$, $R^7$, $Q^{2a}$ and $Q^{2b}$, may be unsubstituted or substituted with one or more of the substituents defined herein.

"$C_2$-$C_6$ alkenyl" refers to a linear or branched hydrocarbon chain radical containing at least two carbon atoms and at least one double bond and includes $C_2$-$C_4$ alkenyl. Examples of alkenyl groups include ethenyl, propenyl, 2-propenyl, 1-butenyl, 2-butenyl, 1-hexenyl, 2-methyl-1- propenyl, 1,2-butadienyl, 1,3-pentadienyl, 1,4-pentadienyl and 1-hexadienyl. Unless stated otherwise, $C_2$-$C_6$ alkenyl within the definitions of $Q^{1a}$ and within the definition of substituents for $R^3$, may be unsubstituted or substituted with one or more of the substituents defined herein.

"$C_2$-$C_6$ alkenylene" refers to a linear or branched hydrocarbon group having one less hydrogen atom from $C_2$-$C_6$ alkenyl as defined above. Examples of $C_2$-$C_6$ alkenylene include ethenylene, propenylene and butenylene. Unless stated otherwise, $C_2$-$C_6$ alkenylene within the definition of substituents for $Q^{1b}$, $Q^{2a}$ and $Q^{2b}$, may be unsubstituted or substituted with one or more of the substituents defined herein.

"$C_2$-$C_6$ alkynyl" refers to a linear or branched hydrocarbon chain radical containing at least two carbon atoms and at least one triple bond. Examples of alkenyl groups include ethynyl, propynyl, 2-propynyl, 1-butynyl, 2-butynyl and 1-hexynyl. Unless specified otherwise, $C_2$-$C_6$ alkynyl, within the definitions of substituents for $R^3$, may be unsubstituted or substituted with one or more of the substituents defined herein.

"$C_1$-$C_6$ alkoxy" refers to a group or part of a group having an —O—$C_x$-$C_y$ alkyl group according to the definition of $C_x$-$C_y$ alkyl above. $C_1$-$C_6$ alkoxy contains from 1 to 6 carbon atoms and includes $C_1$, $C_2$, $C_3$, $C_4$, $C_5$ and $C_6$. Examples of $C_1$-$C_6$ alkoxy include methoxy, ethoxy, propoxy, isopropoxy, butoxy, pentoxy and hexoxy. Alkoxy as employed herein also extends to embodiments in which the or an oxygen atom (e.g. a single oxygen atom) is located within the alkyl chain, for example $CH_2CH_2OCH_3$ or $CH_2OCH_3$. Thus the alkoxy may be linked through carbon to the remainder of the molecule, for example, —$CH_2CH_2OCH_3$, or alternatively, the alkoxy is linked through oxygen to the remainder of the molecule, for example —$OC_{1-6}$ alkyl. In one instance, the alkoxy is linked through oxygen to the remainder of the molecule but the alkoxy group contains a further oxygen atom, for example —$OCH_2CH_2OCH_3$.

Unless specified otherwise, $C_1$-$C_6$ alkoxy and $C_1$-$C_3$ alkoxy within the definitions of $R^a$, $R^f$, $R^g$, $R^i$, $R^j$, $Q^{1a}$, and within the definition of substituents for $R^3$, may be unsubstituted or substituted with one or more of the substituents defined herein. Examples of substituted $C_1$-$C_6$ alkoxy therefore include $OCF_3$, $OCHF_2$, $OCH_2CF_3$, $CH_2CH_2OCH_3$ and $CH_2CH_2OCH_2CH_3$.

The term halo refers to chloro, bromo, fluoro or iodo, in particular chloro or fluoro. Haloalkyl and haloalkoxy groups may contain one or more halo substituents. Examples are trifluoromethyl and trifluoromethoxy. The term "oxo" means =O. The term "nitro" means $NO_2$ and includes $SF_5$ (a known mimetic of nitro).

Cycloalkyl, heterocyclyl, aryl and heteroaryl rings disclosed herein and within the definitions of $R^a$, $R^b$, $R^c$, $R^d$, $R^e$, $R^f$, $R^g$, $R^h$, $R^i$, $R^j$, R', $R^2$, $R^3$ and $R^{11}$ may be monocyclic or bicyclic. Bicyclic ring systems include bridged, fused and spiro ring systems. In particular, the bicyclic ring systems are fused ring systems. A substituent if present may be attached to any suitable ring atom which may be a carbon atom or, in the case of heteroaryl and heterocyclyl ring systems, a heteroatom.

"Cycloalkyl" refers to a monocyclic saturated or partially unsaturated, non-aromatic ring, wherein all of the ring atoms are carbon, and having the number of ring atoms as indicated. For example $C_3$-$C_{10}$ cycloalkyl refers to a monocyclic or bicyclic hydrocarbon ring containing 3 to 10 carbon atoms. Examples of $C_3$-$C_{10}$ cycloalkyl are cyclopropyl, cyclobutyl, cyclopentyl, cyclohexyl, cycloheptyl, cyclooctyl and decahydronaphthalenyl. Bicyclic cycloalkyl groups include bridged ring systems such as bicycloheptane and bicyclooctane. Unless specified otherwise, cycloalkyl within the definitions of $R^a$, $R^b$, $R^c$, $R^d$, $R^e$, $R^f$, $R^g$, $R^h$, $R^i$, $R^j$, R', $R^1$, $R^2$, $R^3$ and $R^{11}$, may be unsubstituted or substituted with one or more of the substituents defined herein.

An "aryl" group/moiety refers to any monocyclic or bicyclic hydrocarbon group comprising at least one aromatic group and having from 5 to 10 carbon atom ring members. Examples of aryl groups include phenyl and naphthyl. Bicyclic rings may be fused aromatic rings where both rings are aromatic, for example, naphthalenyl. Preferred aryl groups are phenyl and naphthyl, more preferably phenyl. Unless specified otherwise, aryl within the definitions of $R^h$, $R^i$, $R^j$, R', $R^2$, $R^3$ and $R^{11}$, may be unsubstituted or substituted with one or more of the substituents defined herein.

"Heteroaryl" as used herein means a polyunsaturated, monocyclic or bicyclic 5 to 10 membered aromatic moiety containing at least one and up to 5 heteroatoms, particularly 1, 2 or 3 heteroatoms selected from N, O and S, and the remaining ring atoms are carbon atoms, in stable combinations known to the skilled person. Heteroaryl ring nitrogen and sulfur atoms are optionally oxidised, and the nitrogen atom(s) are optionally quaternized. A heteroaryl ring can be a single aromatic ring or a fused bicyclic ring where the bicyclic ring system can be aromatic, or one of the fused rings is aromatic and the other is at least partially saturated. In particular examples, a bicyclic heteroaryl is one in which the entire fused ring system is aromatic. A bicyclic heteroaryl can have at least one heteroatom in either of the fused rings. For example, a bicyclic ring with an aromatic ring fused to a partially saturated ring may contain the at least one heteroatom in the aromatic ring or the partially saturated ring. Attachment of the bicyclic ring to the group it is a substituent of may be via either a heteroatom containing ring or a carbon only containing ring. The point of attachment of heteroaryl to the group it is a substituent of can be via a carbon atom or a heteroatom (e.g. nitrogen). Attachment of the bicyclic ring to the group it is a substituent of, in relation to the 6-membered cyano core, is from the aromatic ring. In particular, where $R^2$ is a bicyclic heteroaryl ring comprising an aromatic ring fused to a partially saturated ring, $R^2$ is attached to the nitrogen of the amide linked to the 6-membered cyano core from its aromatic ring. In instances where $R^1$ and $R^2$ together form a heteroaryl ring, the ring containing the amide nitrogen is aromatic and may be fused to a further aromatic ring or a partially saturated ring. Examples of heteroaryl rings include pyridinyl, pyrazinyl, pyrimidinyl, pyridazinyl, furanyl, pyrrolyl, oxazolyl, thiazolyl, thiadiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, quinoxalinyl, dihydrobenzoxazinyl, indolinyl, isoindolinyl, pyrrolopyridinyl, dihydropyrrolopyridinyl, tetrahydropyridopyrazinyl, tetrahydroquinolinyl and tetrahydroisoquinolinyl. Unless specified otherwise, heteroaryl within the definitions of $R^h$, $R^i$, $R^j$, R', $R^2$, $R^3$ and $R^{11}$, may be unsubstituted or substituted with one or more of the substituents defined herein.

"Heterocyclyl" as used herein in describing a ring means, unless otherwise stated, a monocyclic saturated or partially unsaturated, non-aromatic ring or a bicyclic saturated or partially unsaturated ring, wherein the bicyclic ring system is non-aromatic, the mono- or bicyclic ring having, for example, 3 to 10 members, 4 to 10 members or 5 to 10 members, where at least one member and up to 5 members, particularly 1, 2 or 3 members of the ring are heteroatoms selected from N, O and S, and the remaining ring atoms are carbon atoms, in stable combinations known to those of skill in the art. Heterocyclyl ring nitrogen and sulfur atoms are optionally oxidised, and the nitrogen atoms(s) are optionally quaternized. As used herein, the heterocyclyl ring may be a fused ring to another ring system to form a bicycle, i.e. one or two of the heterocyclyl ring carbons is common to an additional ring system. In instances where the heterocylcyl is a bicyclic ring, the second ring can be aromatic, e.g. a fused phenyl, pyridyl, pyrazolyl, or the like. A bicyclic heterocyclyl can have at least one heteroatom in either of the fused rings. For example, a bicyclic ring with an aromatic ring fused to a partially saturated ring may contain the at least one heteroatom in the aromatic ring or the partially saturated ring. Attachment of the bicyclic ring to the group it is a substituent of may be via either a heteroatom containing ring or a carbon only containing ring. The point of attachment of heterocyclyl to the group it is a substituent of can be via a carbon atom or a heteroatom (e.g. nitrogen). Attachment of the bicyclic ring to the group it is a substituent of, in relation to the 6-membered cyano core, is from the saturated or partially saturated (i.e. non-aromatic) ring. In particular, where $R^2$ is a bicyclic ring comprising a partially saturated ring fused to an aromatic ring, $R^2$ is attached to the nitrogen of the amide linked to the 6-membered cyano core from its non-aromatic partially saturated ring. In instances where $R^1$ and $R^2$ together form a bicyclic heterocyclyl ring, the ring containing the amide nitrogen may be partially saturated and fused to a further partially saturated ring or an aromatic ring. Alternatively, when $R^1$ and $R^2$ together form a bicyclic heterocyclyl ring, the ring containing the amide nitrogen may be saturated and fused to a further saturated or partially saturated ring. Examples of heterocyclyl groups include azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydrobenzoxazinyl, tetrahydroisoquinolinyl, pyrrolopyridinyl and dihydropyrrolopyridinyl. Unless specified otherwise, heterocyclyl within the definitions of $R^h$, $R^i$, $R^j$, R', $R^2$, $R^3$ and $R^{11}$, may be unsubstituted or substituted with one or more of the substituents defined herein.

"Optionally substituted" as applied to any group means that the said group may if desired be substituted with one or more substituents (e.g. 1, 2, 3 or 4 substituents) which may be the same or different.

Examples of suitable substituents for "substituted" and "optionally substituted" $C_1$-$C_6$ alkyl (including $C_1$-$C_4$ alkyl, $C_1$-$C_3$ alkyl and $C_1$-$C_2$ alkyl) and $C_1$-$C_6$ alkoxy (including $C_1$-$C_4$ alkoxy, $C_1$-$C_3$ alkoxy and $C_1$-$C_2$ alkoxy) and $C_2$-$C_6$ alkenyl (including $C_2$-$C_4$ alkenyl) and $C_2$-$C_6$ alkynyl (including $C_2$-$C_4$ alkynyl), for example, within the definitions of $R^a$, $R^b$, $R^c$, $R^d$, $R^e$, $R^f$, $R^g$, $R^h$, R', $R^i$, $R^j$, $R^1$, $R^4$, $R^5$, $R^6$, $R^8$, $R^9$, $R^{10}$, $Q^{1a}$, and within the definition of substituents for $R^3$, and $C_0$-$C_3$ and $C_1$-$C_6$ alkylene (including $C_1$-$C_3$ alkylene) and $C_2$-$C_6$ alkenylene, for example, within the definitions of $R^h$, $Q^{1a}$, $Q^{1b}$, $R^7$, $Q^{2a}$ and $Q^{2b}$, include $C_1$-$C_6$ alkoxy, halo, hydroxyl, thiol, cyano, amino and nitro, in particular, halo (preferably fluoro or chloro), hydroxyl and cyano.

Examples of suitable substituents for "substituted" and "optionally substituted" rings, i.e. cycloalkyl, heterocyclyl, aryl and heteroaryl rings, for example, within the definitions of $R^a$, $R^b$, $R^c$, $R^d$, $R^e$, $R^f$, $R^g$, $R^h$, $R^i$, $R^j$, R', $R^2$, $R^3$ and $R^{11}$, include halo, cyano, oxo, nitro, amino, amide, hydroxy, $C_1$-$C_6$ alkyl or $C_1$-$C_3$ alkyl, $C_1$-$C_6$ alkoxy or $C_1$-$C_3$ alkoxy, aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, mono-$C_{1-3}$ carbamoyl, di-$C_{1-3}$ carbamoyl or any of the above in which a hydrocarbyl moiety is itself substituted by halo, in particular fluoro, hydroxyl, cyano, amino or nitro. In groups containing an oxygen atom such as hydroxy and alkoxy, the oxygen atom can be replaced with sulfur to make groups such as thio (SH) and thio-alkyl (S-alkyl). Optional substituents therefore include groups such as S-methyl. In thio-alkyl groups, the sulfur atom may be further oxidised to make a sulfoxide or sulfone, and thus optional substituents therefore includes groups such as S(O)-alkyl and S(O)$_2$-alkyl.

Examples of suitable substituents for "substituted" and "optionally substituted" rings include in particular, halo, oxo, cyano, $C_1$-$C_3$ alkyl, $C_1$-$C_3$ alkoxy, heterocyclyl, cycloalkyl, heteroary or aryl, wherein the alkyl or alkoxy is optionally substituted with one or more (e.g. one, two or three) substituents selected from halo, hydroxyl, thiol, cyano, amino and nitro. In particular, suitable substituents for "substituted" and "optionally substituted" rings disclosed herein include fluoro, chloro, oxo, cyano, $C_1$-$C_3$ alkyl, $C_1$-$C_3$ alkoxy, wherein the alkyl or alkoxy is optionally substituted with one or more (e.g. one, two or three) substituents selected from $C_1$-$C_6$ alkoxy, halo, hydroxyl, thiol, cyano, amino and nitro, in particular, one or more fluoro.

Substituted groups thus include for example Br, Cl, F, CN, Me, Et, Pr, t-Bu, i-Bu, OMe, OEt, OPr, CH(CH$_3$)$_2$, CF$_3$, OCF$_3$, C(O)NHCH$_3$, cyclopropyl, phenyl, etc. In the case of aryl groups, the substitutions may be in the form of rings from adjacent carbon atoms in the aryl ring, for example cyclic acetals such as O—CH$_2$—O.

In one preferred aspect of the invention, X represents O.

In another preferred aspect, X represents N(R$^h$) wherein R$^h$ represents hydrogen, optionally substituted $C_1$-$C_3$ alkyl, C(O)R', S(O)$_2$R', or a 3 to 6 membered heterocyclyl, heteroaryl, cycloalkyl or aryl ring via a $C_0$-$C_3$ alkylene linker, and wherein R' represents optionally substituted $C_1$-$C_3$ alkyl or a 3 to 6 membered heterocyclyl, heteroaryl, cycloalkyl or aryl ring. Preferably, R$^h$ is selected from methyl, C(O)Me, S(O)$_2$Me, and phenyl.

In another preferred aspect, X represents C(R$^i$)(R$^j$) wherein R$^i$ and R$^j$ each independently represent hydrogen, fluoro, cyano, an optionally substituted $C_1$-$C_3$ alkyl, an optionally $C_1$-$C_3$ alkoxy, or a 3 to 6 membered heterocyclyl, heteroaryl, cycloalkyl or aryl ring or a spirocyclic group where R$^i$ is linked to R$^j$. The alkyl and alkoxy may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano. The heterocyclyl, heteroaryl, cycloalkyl and aryl rings may be unsubstituted or substituted. In particular, the heterocyclyl, heteroaryl, cycloalkyl and aryl may be unsubstituted or substituted with a substituent selected from halo, cyano, oxo, nitro, amino, amido, hydroxyl, $C_1$-$C_6$ alkyl or $C_1$-$C_3$ alkyl, $C_1$-$C_6$ alkoxy or $C_1$-$C_3$ alkoxy, wherein the alkyl and alkoxy may be optionally substituted with halo. Preferably, $R^i$ and $R^j$ each represent hydrogen.

Alternatively, $R^j$ may be linked to $R^a$ or $R^g$ to form an optionally substituted $C_3$-$C_4$ cycloalkyl ring. The cycloalkyl ring may be unsubstituted or substituted.

When X is O or N($R^h$), $R^a$ may represent hydrogen or an optionally substituted $C_1$-$C_3$ alkyl. $R^a$ may represent hydrogen. $R^a$ may represent $C_1$-$C_3$ alkyl. $R^a$ may represent methyl. The alkyl may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano. Preferably, $R^a$ is hydrogen.

When X is C($R^i$)($R^j$), $R^a$ may represent hydrogen, fluoro, an optionally substituted $C_1$-$C_3$ alkyl or an optionally substituted $C_1$-$C_3$ alkoxyl. $R^a$ may represent hydrogen. $R^a$ may represent fluoro. $R^a$ may represent $C_1$-$C_3$ alkyl. $R^a$ may represent methyl. $R^a$ may represent $C_1$-$C_3$ alkoxyl. $R^a$ may represent methoxy. The alkyl or alkoxyl may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano. Preferably, when X is C($R^i$)($R^j$), $R^a$ is hydrogen or fluoro.

When $R^a$ represents fluoro or an optionally substituted $C_1$-$C_3$ alkyl, $R^b$, $R^c$, $R^d$, $R^e$, $R^f$ and $R^g$, and $R^h$ or $R^i$ and $R^j$ if present, may each represent hydrogen. The alkyl may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano.

Alternatively, when X is C($R^i$)($R^j$), $R^a$ may be linked to $R^b$ or $R^j$ to form an optionally substituted $C_3$-$C_4$ cycloalkyl ring. The cycloalkyl ring may be unsubstituted or substituted. In particular, the cycloalkyl may be unsubstituted or substituted with a substituent selected from halo, cyano, oxo, nitro, amino, amido, hydroxyl, $C_1$-$C_6$ alkyl or $C_1$-$C_3$ alkyl, $C_1$-$C_6$ alkoxy or $C_1$-$C_3$ alkoxy, wherein the alkyl and alkoxy may be optionally substituted with halo.

$R^b$, $R^c$, $R^d$ and $R^e$ may each independently represent hydrogen or an optionally substituted $C_1$-$C_3$ alkyl. $R^b$ may be hydrogen or $C_1$-$C_3$ alkyl and $R^c$ may be hydrogen. $R^d$ may be hydrogen or $C_1$-$C_3$ alkyl and $R^e$ may be hydrogen. The alkyl may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano.

$R^b$ may represent hydrogen. $R^b$ may represent $C_1$-$C_3$ alkyl. $R^b$ may represent methyl. When $R^b$ represents $C_1$-$C_3$ alkyl, $R^a$, $R^c$, $R^d$, $R^e$, $R^f$ and $R^g$, $R^h$ if present, and $R^i$ and $R^j$ if present, may each represent hydrogen. The alkyl may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano.

$R^c$ may represent hydrogen. $R^c$ may represent $C_1$-$C_3$ alkyl. $R^c$ may represent methyl. When $R^c$ represents $C_1$-$C_3$ alkyl, $R^a$, $R^b$, $R^d$, $R^e$, $R^f$ and $R^g$, $R^h$ if present, and $R^i$ and $R^j$ if present, may each represent hydrogen. The alkyl may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano.

In one embodiment, when $R^c$ is other than hydrogen, $R^b$ is hydrogen. When $R^b$ is other than hydrogen, $R^c$ is hydrogen, such that one of $R^b$ and $R^c$ is hydrogen.

$R^d$ may represent hydrogen. $R^d$ may represent $C_1$-$C_3$ alkyl. $R^d$ may represent methyl. When $R^d$ represents $C_1$-$C_3$ alkyl, $R^a$, $R^b$, $R^c$, $R^e$, $R^f$ and $R^g$, $R^h$ if present, and $R^i$ and $R^j$ if present, may each represent hydrogen. The alkyl may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano.

$R^e$ may represent hydrogen. $R^e$ may represent $C_1$-$C_3$ alkyl. $R^e$ may represent methyl. When $R^e$ represents $C_1$-$C_3$ alkyl, $R^a$, $R^b$, $R^c$, $R^d$, $R^f$ and $R^g$, $R^h$ if present, and $R^i$ and $R^j$ if present, may each represent hydrogen. The alkyl may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano.

In one embodiment, when $R^e$ is other than hydrogen, $R^d$ is hydrogen. When $R^d$ is other than hydrogen, $R^e$ is hydrogen, such that one of $R^d$ and $R^e$ is hydrogen.

When X is O or N($R^h$), $R^f$ and $R^g$ may represent hydrogen, cyano or optionally substituted $C_1$-$C_3$ alkyl. The alkyl may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano.

When X is O or N($R^h$), $R^f$ may represent hydrogen. $R^f$ may represent cyano. $R^f$ may represent $C_1$-$C_3$ alkyl. $R^f$ may represent methyl. When $R^f$ represents cyano or $C_1$-$C_3$ alkyl, $R^a$, $R^b$, $R^c$, $R^d$, $R^e$ and $R^g$, $R^h$ if present, and $R^i$ and $R^j$ if present, may each represent hydrogen. The alkyl may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano.

When X is O or N($R^h$), $R^g$ may represent hydrogen. $R^g$ may represent cyano. $R^g$ may represent $C_1$-$C_3$ alkyl. $R^g$ may represent methyl. When $R^g$ represents cyano or $C_1$-$C_3$ alkyl, $R^a$, $R^b$, $R^c$, $R^d$, $R^e$ and $R^f$, $R^h$ if present, and $R^i$ and $R^j$ if present, may each represent hydrogen. The alkyl may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano.

When X is C($R^i$)($R^j$), $R^f$ and $R^g$ each independently represent hydrogen, fluoro, cyano, an optionally substituted $C_1$-$C_3$ alkyl or an optionally substituted $C_1$-$C_3$ alkoxy. The alkyl or alkoxy may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano.

When X is C($R^i$)($R^j$), $R^f$ may represent hydrogen. $R^f$ may represent fluoro. $R^f$ may represent cyano. $R^f$ may represent $C_1$-$C_3$ alkyl. $R^f$ may represent methyl. $R^f$ may represent $C_1$-$C_3$ alkoxy. $R^f$ may represent methoxy. When $R^f$ represents fluoro, cyano, an optionally substituted $C_1$-$C_3$ alkyl or an optionally substituted $C_1$-$C_3$ alkoxy, $R^a$, $R^b$, $R^c$, $R^d$, $R^e$, $R^g$, $R^h$ and $R^i$ and $R^j$ if present, may each represent hydrogen. The alkyl or alkoxy may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano.

When X is C($R^i$)($R^j$), $R^g$ may represent hydrogen. $R^g$ may represent fluoro. $R^g$ may represent cyano. $R^g$ may represent $C_1$-$C_3$ alkyl. $R^g$ may represent methyl. $R^g$ may represent $C_1$-$C_3$ alkoxy. $R^g$ may represent methoxy. When $R^g$ represents fluoro, cyano, an optionally substituted $C_1$-$C_3$ alkyl or an optionally substituted $C_1$-$C_3$ alkoxy, $R^a$, $R^b$, $R^c$, $R^d$, $R^e$, $R^f$, $R^h$ and $R^i$ and $R^j$ if present, may each represent hydrogen. The alkyl or alkoxy may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano.

When X is C($R^i$)($R^j$), in particular examples, $R^f$ and $R^g$ are independently selected from hydrogen and fluoro. $R^f$ and $R^g$ may each represent hydrogen. $R^f$ and $R^g$ may each represent fluoro. When $R^f$ is hydrogen, $R^g$ may represent fluoro. When $R^f$ is fluoro, $R^g$ may represent hydrogen.

In one embodiment, when $R^g$ is other than hydrogen, $R^f$ is hydrogen. When $R^f$ is other than hydrogen, $R^g$ is hydrogen, such that one of $R^f$ and $R^g$ is hydrogen.

Alternatively, $R^b$, $R^c$, $R^d$, $R^e$, $R^f$, $R^g$, $R^i$ and $R^j$ may each independently represent one or more spirocyclic groups. $R^b$ may be linked to $R^c$ to form a spirocyclic ring. In addition, or alternatively, $R^d$ may be linked to $R^e$ to form a spirocyclic ring. In addition, or alternatively, $R^f$ may be linked to $R^g$ to form a spirocyclic ring. In addition, or alternatively, $R^i$ may be linked to $R^j$ to form a spirocyclic ring. The spirocyclic ring can contain 3, 4, 5 or 6 atoms, in particular 3 or 4 atoms. When $R^b$ and $R^c$ together form a spirocyclic ring, $R^a$, $R^d$, $R^e$, $R^f$ and $R^g$, and $R^h$ or $R^i$ and $R^j$ if present, may be hydrogen. When $R^d$ and $R^e$ together form a spirocyclic ring, $R^a$, $R^b$, $R^c$, $R^f$ and $R^g$, and $R^h$ or $R^i$ and $R^j$ if present, may be hydrogen. When $R^f$ and $R^g$ together form a spirocyclic ring, $R^a$, $R^b$, $R^c$, $R^d$ and $R^e$, and $R^h$ or $R^i$ and $R^j$ if present, may be hydrogen. When $R^i$ and $R^j$ together form a spirocyclic ring, $R^a$, $R^b$, $R^c$, $R^d$, $R^e$ and $R^f$ may be hydrogen The spirocyclic ring shares one ring atom with the 6-membered cyano core. The spirocyclic ring may be substituted or unsubstituted. In particular, the spirocyclic ring may be unsubstituted or substituted with a substituent selected from halo, cyano, oxo, nitro, amino, amido, hydroxyl, $C_1$-$C_6$ alkyl or $C_1$-$C_3$ alkyl, $C_1$-$C_6$ alkoxy or $C_1$-$C_3$ alkoxy, wherein the alkyl and alkoxy may be optionally substituted with halo.

Neighbouring R groups attached to the carbon ring atoms of the cyanopyrrolidine core may together form an optionally substituted $C_3$-$C_4$ cycloalkyl ring. For example, $R^a$ together with $R^b$ or $R^j$, $R^e$ together with $R^f$, and $R^g$ together with $R^j$. In such instances, preferably one cycloalkyl group is present whilst the remaining R groups each represent hydrogen. The $C_3$-$C_4$ cycloalkyl ring may be unsubstituted or substituted with a substituent selected from halo, cyano, oxo, nitro, amino, amido, hydroxyl, $C_1$-$C_6$ alkyl or $C_1$-$C_3$ alkyl, $C_1$-$C_3$ alkoxy or $C_1$-$C_3$ alkoxy, wherein the alkyl and alkoxy may be optionally substituted with halo.

One of $R^a$, $R^b$, $R^c$, $R^d$, $R^e$, $R^f$ or $R^g$, and $R^h$ or $R^i$ and $R^j$ if present, may be other than hydrogen, and the remaining are each hydrogen.

Two of $R^a$, $R^b$, $R^c$, $R^d$, $R^e$, $R^f$ or $R^g$, and $R^h$ or $R^i$ and $R^j$ if present, may be other than hydrogen, and the remaining are each hydrogen.

Three of $R^a$, $R^b$, $R^c$, $R^d$, $R^e$, $R^f$ or $R^g$, and $R^h$ or $R^i$ and $R^j$ if present, may be other than hydrogen, and the remaining are each hydrogen.

Four of $R^a$, $R^b$, $R^c$, $R^d$, $R^e$, $R^f$ or $R^g$, and $R^h$ or $R^i$ and $R^j$ if present, may be other than hydrogen, and the remaining are each hydrogen.

Five of $R^a$, $R^b$, $R^c$, $R^d$, $R^e$, $R^f$ or $R^g$, and $R^h$ or $R^i$ and $R^j$ if present, may be other than hydrogen, and the remaining are each hydrogen.

Six of $R^a$, $R^b$, $R^c$, $R^d$, $R^e$, $R^f$ or $R^g$, and $R^h$ or $R^i$ and $R^j$ if present, may be other than hydrogen, and the remaining is hydrogen.

When one, two, three, four, five or six of $R^a$, $R^b$, $R^c$, $R^d$, $R^e$, $R^f$, $R^g$, and $R^h$ or $R^i$ and $R^j$ if present, are other than hydrogen, the other R groups represent a group in accordance with the definitions above. In particular, one, two, three or four of $R^a$, $R^b$, $R^c$, $R^d$, $R^e$, $R^f$ or $R^g$, and $R^h$ or $R^i$ and $R^j$ if present, are other than hydrogen and the remaining each represent hydrogen. More particularly, one or two of $R^a$, $R^b$, $R^c$, $R^d$, $R^e$, $R^f$ or $R^g$, and $R^h$ or $R^i$ and $R^j$ if present, are other than hydrogen and the remaining each represent hydrogen.

In particular, $R^a$, $R^b$, $R^c$, $R^d$, $R^e$, $R^f$ and $R^g$, and $R^h$ or $R^i$ and $R^j$ if present, may each represent hydrogen.

In formula (I) defined herein, $R^1$ may represent hydrogen or an optionally substituted $C_1$-$C_3$ alkyl. $R^1$ may represent hydrogen. $R^1$ may represent an optionally substituted $C_1$-$C_3$ alkyl. $R^1$ may represent an optionally substituted methyl or ethyl. The alkyl may be unsubstituted or substituted with one or more substituents selected from $C_1$-$C_6$ alkoxy, halo, hydroxyl, thiol, cyano, amino and nitro, in particular halo (preferably fluoro or chloro), hydroxyl and cyano.

In formula (I) defined herein, $R^2$ may represent a 5 to 10 membered monocyclic or bicyclic heteroaryl or aryl ring. The heteroaryl or aryl ring may be substituted or unsubstituted.

When the $R^2$ ring is a bicyclic heteroaryl or aryl ring, the second ring (i.e. the ring not attached to the nitrogen of the amide linked to the 6-membered cyano core) may be aromatic or partly saturated and thus whilst not every atom in the 5 to 10 membered heteroaryl or aryl ring need be in an aromatic system, there must be at least one aryl or heteroaryl ring within the 5 to 10 atoms, and this aryl or heteroaryl ring must be directly attached to the amide nitrogen.

Alternatively, $R^2$ may represent a 3 to 10 membered monocyclic or bicyclic heterocyclyl or cycloalkyl ring. When $R^2$ represents a hyeterocyclyl or cycloalkyl ring, the ring must be substituted.

$R^1$ and $R^2$ may together form a 5 to 10 membered monocyclic or bicyclic heteroaryl ring. The heteroaryl ring may be substituted or unsubstituted.

Alternatively, $R^1$ and $R^2$ may together form a 4 to 10 membered monocyclic or bicyclic heterocyclyl ring. When $R^1$ and $R^2$ together form a heterocyclyl ring, the ring must be substituted.

When $R^1$ and $R^2$ together form a heteroaryl ring, the ring containing the amide nitrogen is aromatic and may be fused to a further aromatic ring or a partially saturated ring, and thus whilst not every atom in the heteroaryl ring need be in an aromatic system, there must be at least one aromatic ring within the 5 to 10 atoms.

When $R^1$ and $R^2$ together form a heterocyclyl ring, the ring containing the amide nitrogen may be partially saturated and may be fused to a further partially saturated ring or an aromatic ring. Alternatively, when $R^1$ and $R^2$ together form a heterocyclyl ring, the ring containing the amide nitrogen may be saturated and may be fused to a further saturated or partially saturated ring.

$R^2$ may represent a 5 to 10 membered monocyclic or bicyclic optionally substituted heteroaryl or aryl ring, or a 3 to 10 membered monocyclic or bicyclic substituted heterocyclyl or cycloalkyl ring, or $R^1$ and $R^2$ may together form a 5 to 10 membered monocyclic or bicyclic optionally substituted heteroaryl ring, or a 4 to 10 membered monocyclic or bicyclic substituted heterocyclyl ring, and when substituted, may be substituted with one or more (e.g. one, two, three or four) of -$Q^1(R^3)^n$, in particular one or two of -$Q^1(R^3)_n$.

$R^2$ may represent a 5 to 10 membered monocyclic or bicyclic optionally substituted aryl or heteroaryl ring, and when substituted, may be substituted with one or more (e.g. one, two, three or four) of -Q$^1$(R$^3$)$_n$, in particular one or two of -Q$^1$(R$^3$)$_n$.

In particular, R$^2$ may represent a 5 or 6 membered aryl or heteroaryl ring which is optionally substituted with one or more (e.g. one, two, three or four) of -Q$^1$(R$^3$)$_n$, or R$^2$ may represent a 5 or 6 membered heterocyclyl or cycloalkyl ring which is substituted with one or more (e.g. one, two, three or four) of -Q$^1$(R$^3$)$_n$.

Alternatively, R$^2$ may represent a 9 or 10 membered bicyclic aryl or heteroaryl ring which may be optionally substituted with one or more (e.g. one, two, three or four) of -Q$^1$(R$^3$)$_n$, or R$^2$ may represent a 9 or 10 membered bicyclic heterocyclyl or cycloalkyl ring which is substituted with one or more (e.g. one, two, three or four) of -Q$^1$(R$^3$)$_n$.

R$^1$ and R$^2$ may represent a 4 membered heterocyclyl ring which is optionally substituted with one or more (e.g. one, two or three) of -Q$^1$(R$^3$)$_n$.

Alternatively, R$^1$ and R$^2$ may represent a 5 to 8 membered monocyclic heteroaryl ring which is optionally substituted with one or more (e.g. one, two, three or four) of -Q$^1$(R$^3$)$_n$. Alternatively, R$^1$ and R$^2$ may represent a 5 or 6 membered monocyclic heteroaryl ring which is optionally substituted with one or more (e.g. one, two, three or four) of -Q$^1$(R$^3$)$_n$.

Alternatively, R$^1$ and R$^2$ may represent a 5 to 8 membered monocyclic heterocyclyl ring which is substituted with one or more (e.g. one, two, three or four) of -Q$^1$(R$^3$)$_n$. Alternatively, R$^1$ and R$^2$ may represent a 5 or 6 membered monocyclic heterocyclyl ring which is substituted with one or more (e.g. one, two, three or four) of -Q$^1$(R$^3$)$_n$.

Alternatively, R$^1$ and R$^2$ may represent a 9 or 10 membered bicyclic heteroaryl ring which may be optionally substituted with one or more (e.g. one, two, three or four) of -Q$^1$(R$^3$)$_n$. Alternatively, R$^1$ and R$^2$ may represent a 9 to 10 membered bicyclic heterocyclyl ring which is substituted with one or more (e.g. one, two, three or four) of -Q$^1$(R$^3$)$_n$.

When R$^2$, or the ring formed by R$^1$ together with R$^2$, is a heteroaryl or heterocyclyl ring, the ring may comprise one or more (e.g. 1, 2 or 3) heteroatoms independently selected from nitrogen, oxygen and sulfur. In particular, the heteroaryl or heterocyclyl ring contains at least one nitrogen atom, for example, 1, 2 or 3 nitrogen atoms, preferably 1 or 2 nitrogen heteroatoms.

R$^2$ may be selected from the group consisting of pyridinyl, pyrazinyl, pyrimidinyl, pyridazinyl, furanyl, pyrrolyl, oxazolyl, thiazolyl, thiadiazolyl, pyrazolyl, triazolyl, tetrazolyl, indolyl, indolinyl, indolizinyl, isoindolyl, isoindolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, quinoxalinyl, dihydrobenzoxazinyl, pyrrolopyridinyl, tetrahydropyridopyrazinyl, phenyl, naphthyl, naphthalenyl, dihydropyrrolopyridinyl, cyclopropyl, cyclobutyl, cyclopentyl, cyclohexyl, cycloheptyl, cyclooctyl, decahydronaphthalenyl, bicycloheptane, bicyclooctane, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl and tetrahydroisoquinolinyl.

In particular, R$^2$ may be selected from pyridinyl, thiazolyl, thiadiazolyl, isoquinolinyl, phenyl, isoxazolyl, benzothiazolyl, pyrimidinyl, imidazolyl, pyrazolyl, pyridazinyl and pyrrolidinyl.

The ring formed by R$^1$ together with R$^2$ may be selected from the group consisting of pyridinyl, pyrazinyl, pyrimidinyl, pyridazinyl, pyrrolyl, oxazolyl, thiazolyl, thiadiazolyl, pyrazolyl, triazolyl, tetrazolyl, indolyl, indolinyl, indolizinyl, isoindolyl, isoindolinyl, purinyl, furazanyl, imidazolyl, indazolyl, isothiazolyl, isoxazolyl, oxadiazolyl, tetrazolyl, thiadiazolyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, quinoxalinyl, dihydrobenzoxazinyl, pyrrolopyridinyl, dihydropyrrolopyridinyl, tetrahydropyridopyrazinyl, azetidinyl, pyrrolidinyl, piperidinyl, azepanyl, diazepanyl, morpholinyl, oxazolidinyl, oxazinanyl, piperazinyl, thiomorpholinyl, homopiperazinyl, hexahydropyrimidinyl, pyrazolinyl, pyrazolidinyl, 4H-quinolizinyl, quinuclidinyl, tetrahydropyridinyl, tetrahydropyrimidinyl, thiazolidinyl, tetrahydroquinolinyl and tetrahydroisoquinolinyl.

In particular, the ring formed by R$^1$ together with R$^2$ may be dihydropyrrolopyridinyl.

Examples of R$^2$ include those shown below:

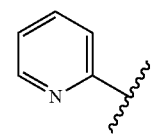

A

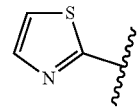

B

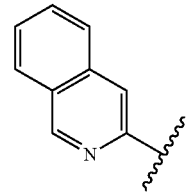

C

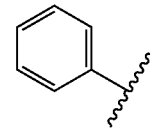

D

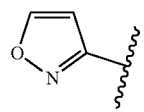

E

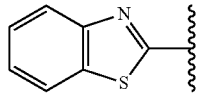

F

G 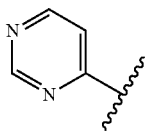

H 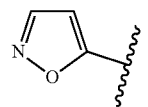

I 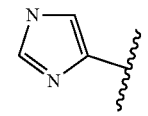

J 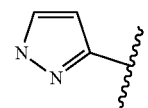

K 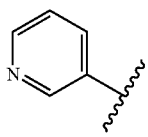

L 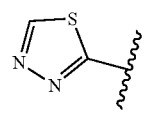

M 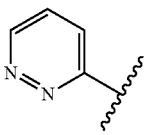

N 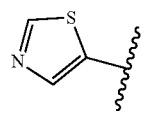

O 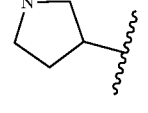

wherein

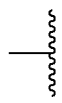

represents the point of attachment to the remainder of the molecule, i.e. to the nitrogen of the amide linked to the 6-membered cyano core, and wherein rings A to N are optionally substituted as described herein, and ring O is substituted as described herein. Hydrogen atoms attached to ring nitrogen atoms have not been shown. It will be understood by the skilled person which ring nitrogen atoms are suitable for substitution and where not substituted the nitrogen may be bound to a hydrogen atom to complete its valency, where appropriate.

An example of a ring formed by $R^1$ and $R^2$ together includes the ring shown below:

P 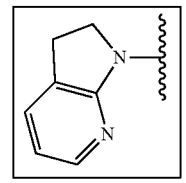

wherein

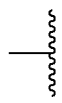

represents the point of attachment to the remainder of the molecule, i.e. to the carbonyl linked to the 6-membered cyano core, and wherein the ring is optionally substituted as described herein.

When substituted, $R^2$, or the ring formed by $R^1$ together with $R^2$, may be substituted with one or more $-Q^1(R^3)_n$, in particular one or two $-Q^1(R^3)_n$, wherein each occurrence $-Q^1(R^3)_n$ is the same or different, and wherein:

n is 0 or 1;

when n is 0, $Q^1$ represents $Q^{1a}$; and when n is 1, $Q^1$ represents $Q^{1b}$.

n may be 0. Alternatively, n may be 1.

$Q^{1a}$ may be selected from halo, cyano, nitro, hydroxyl, —$SR^4$, —$NR^4R^5$, —$CONR^4R^5$, —$C_0$-$C_3$-alkylene-$NR^4COR^5$, —$NR^4CONR^5R^6$, —$COR^4$, —$C(O)OR^4$, —$SO_2R^4$, —$SO_2NR^4R^5$, —$NR^4SO_2R^5$, —$NR^4SO_2NR^5R^6$, —$NR^4C(O)OR^5$, optionally substituted —$C_1$-$C_6$ alkyl, optionally substituted $C_1$-$C_6$ alkoxy, optionally substituted —$C_2$-$C_6$ alkenyl. The alkyl, alkoxy or alkenyl may be unsubstituted or substituted with a group selected from $C_1$-$C_6$ alkoxy, halo, hydroxyl, thiol, cyano, amino and nitro.

In particular, $Q^{1a}$ may be selected from halo, cyano, optionally substituted $C_1$-$C_3$ alkyl and optionally substituted $C_1$-$C_3$ alkoxy. $Q^{1a}$ may be selected from halo, cyano, methyl, ethyl, propyl, methoxy, ethoxy and propoxy. $Q^{1a}$ may be an optionally substituted $C_1$-$C_3$ alkoxy. In particular examples, $Q^{1a}$ is propoxy. The alkyl or alkoxy may be unsubstituted or substituted with a group selected from $C_1$-$C_6$ alkoxy, halo, hydroxyl, thiol, cyano, amino and nitro.

$Q^{1b}$ is selected from a covalent bond, an oxygen atom, a sulfur atom, —$OR^7$—, —$SO$—, —$SO_2$—, —$CO$—, —$C(O)O$—, —$C_0$-$C_3$-alkylene-$C(O)NR^4$—$C_0$-$C_3$ alkylene, —$C_0$-$C_3$-alkylene-$NR^4$—$C_0$-$C_3$ alkylene, —$C_0$-$C_3$-alkylene-$NR^4C(O)$—$C_0$-$C_3$ alkylene, —$NR^4CONR^5$—, —$SO_2NR^4$—, $NR^4SO_2$—, —$NR^4SO_2NR^5$—, —$NR^4C(O)O$—, —$NR^4C(O)OR^7$—, optionally substituted $C_1$-$C_6$ alkylene, or optionally substituted —$C_2$-$C_6$ alkenylene. In particular examples, $Q^{1b}$ is a covalent bond. The alkylene or alkenylene may be unsubstituted or substituted with a group selected from $C_1$-$C_6$ alkoxy, halo, hydroxyl, thiol, cyano, amino and nitro.

$R^4$, $R^5$ and $R^6$ each independently represent hydrogen or an optionally substituted $C_1$-$C_6$ alkyl. The alkyl may be unsubstituted or substituted with a group selected from $C_1$-$C_6$ alkoxy, halo, hydroxyl, thiol, cyano, amino and nitro.

$R^7$ represents an optionally substituted $C_1$-$C_6$ alkylene. The alkylene may be unsubstituted or substituted with a group selected from $C_1$-$C_6$ alkoxy, halo, hydroxyl, thiol, cyano, amino and nitro.

In particular examples, $R^2$, or the ring formed by $R^1$ together with $R^2$ is substituted with a further ring, i.e., $R^2$, or the ring formed by $R^1$ together with $R^2$ is substituted with at least one $-Q^1$-$(R^3)_n$ wherein n is 1.

When n is 1, $R^3$ represents an optionally substituted 3 to 10 membered monocyclic or bicyclic heterocyclyl, heteroaryl, cycloalkyl or aryl ring (when n is 0, $Q^1$ is present as $Q^{1a}$ and $R^3$ is absent). The heterocyclyl, heteroaryl, cycloalkyl or aryl ring may be unsubstituted or substituted.

$R^3$ may be selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrrolidinyl, pyrazinyl, pyrimidinyl, pyridazinyl, furanyl, pyrrolyl, oxazolyl, thiazolyl, thiadiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydropyridinyl, quinoxalinyl, dihydrobenzoxazinyl, pyrrolopyridinyl, dihydropyrrolopyridinyl, tetrahydropyridopyrazinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl and tetrahydroisoquinolinyl.

$R^3$ may represent an optionally substituted 3 or 4 membered heterocyclyl or cycloalkyl ring.

Alternatively, $R^3$ may represent an optionally substituted 5 or 6 membered heterocyclyl, heteroaryl, aryl or cycloalkyl ring.

Alternatively, $R^3$ may represent an optionally substituted 9 or 10 membered bicyclic heterocyclyl, heteroaryl, aryl or cycloalkyl ring.

In particular, $R^3$ is selected from substituted or unsubstituted phenyl, pyrazolyl, pyridinyl and indazolyl.

More particularly, $R^3$ is a substituted or unsubstituted phenyl.

In all cases described herein, $R^3$ may be optionally substituted with one or more substituents independently selected from halo, cyano, oxo, nitro, hydroxyl, —$SR^8$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^{2a}$-$R^{11}$, -$Q^{2a}$-O-$Q^{2b}$-$R^{11}$, -$Q^{2a}$-S-$Q^{2b}$-$R^{11}$, -$Q^{2a}$-SO-$Q^{2b}$-$R^{11}$, -$Q^{2a}$-$NR^8CONR^9R^{10}$, -$Q^{2a}$-$NR^8CONR^9$-$Q^{2a}$-$R^{11}$, -$Q^{2a}$-$NR^8R^9$, -$Q^{2a}$-$NR^8$-$Q^{2b}$-$R^{11}$, -$Q^{2a}$-$COR^8$, -$Q^{2a}$-CO-$Q^{2b}$-$R^{11}$, -$Q^{2a}$-$NR^8COR^9$, -$Q^{2a}$-$NR^8CO$-$Q^{2b}$-$R^{11}$, -$Q^{2a}$-$NR^8C(O)OR^9$, -$Q^{2a}$-$NR^8C(O)O$-$Q^{2b}$-$R^{11}$, -$Q^{2a}$-$SO_2R^8$, -$Q^{2a}$-$SO_2$-$Q^{2b}$-$R^{11}$, -$Q^{2a}$-$CONR^8R^9$, -$Q^{2a}$-$CONR^8$-$Q^{2b}$-$R^{11}$, -$Q^{2a}$-$CO_2R^8$, -$Q^{2a}$-$CO_2$-$Q^{2b}$-$R^{11}$, -$Q^{2a}$-$SO_2NR^8R^9$, -$Q^{2a}$-$SO_2NR^8$-$Q^{2b}$-$R^{11}$, -$Q^{2a}$-$NR^8SO_2R^9$, -$Q^{2a}$-$NR^8SO_2$-$Q^{2b}$-$R^{11}$, -$Q^{2a}$-$NR^8SO_2NR^9R^{10}$, and -$Q^{2a}$-$NR^8SO_2NR^9$-$Q^{2b}$-$R^{11}$, wherein the alkyl, alkoxy, alkenyl or alkynyl are optionally substituted with one or more substituents selected from $C_1$-$C_6$ alkoxy, halo, hydroxyl, thiol, cyano, amino and nitro.

$Q^{2a}$ and $Q^{2b}$ each independently represent a covalent bond, optionally substituted $C_1$-$C_6$ alkylene or optionally substituted $C_2$-$C_6$ alkenylene. In particular, $Q^{2a}$ represents a covalent bond. In particular, $Q^{2b}$ represents a covalent bond. The alkylene or alkenylene may be unsubstituted or substituted with a group selected from $C_1$-$C_6$ alkoxy, halo, hydroxyl, thiol, cyano, amino and nitro.

$R^8$, $R^9$ and $R^{10}$ each independently represent hydrogen or optionally substituted $C_1$-$C_6$ alkyl. In particular, $R^8$, $R^9$ and $R^{10}$ each represent hydrogen. The alkyl may be unsubstituted or substituted with a group selected from $C_1$-$C_6$ alkoxy, halo, hydroxyl, thiol, cyano, amino and nitro.

$R^{11}$ represents an optionally substituted 3 to 10 membered heterocyclyl, heteroaryl, aryl or cycloalkyl ring. The heterocyclyl, heteroaryl, aryl or cycloalkyl may be unsubstituted or substituted. In particular, $R^{11}$ represents a $C_3$-$C_4$ cycloalkyl ring or a 5 or 6 membered aryl or heteroaryl ring. More particularly $R^{11}$ represents a 5 or 6 membered heteroaryl ring. More particularly, $R^{11}$ represents pyrazolyl. $R^{11}$ may be unsubstituted or substituted with a substituent selected from halo, cyano, oxo, nitro, amino, amido, hydroxyl, $C_1$-$C_6$ alkyl or $C_1$-$C_3$ alkyl, $C_1$-$C_6$ alkoxy or $C_1$-$C_3$ alkoxy, wherein the alkyl and alkoxy may be optionally substituted with halo.

In particular, $R^3$ may be optionally substituted with one or more substituents independently selected from halo, cyano, oxo, nitro, hydroxyl, —$SR^8$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^{2a}$-$NR^8CONR^9R^{10}$, -$Q^{2a}$-$NR^8R^9$, -$Q^{2a}$-$COR^8$, -$Q^{2a}$-$NR^8COR^9$, -$Q^{2a}$-$NR^8C(O)OR^9$, -$Q^{2a}$-$SO_2R^8$, -$Q^{2a}$-$CONR^8R^9$, -$Q^{2a}$-$CO_2R^8$, -$Q^{2a}$-$SO_2NR^8R^9$, -$Q^{2a}$-$NR^8SO_2R^9$ and -$Q^{2a}$-$NR^8SO_2NR^9R^{10}$, wherein the alkyl, alkoxy, alkenyl or alkynyl are optionally substituted with one or more substituents selected from $C_1$-$C_6$ alkoxy, halo, hydroxyl, thiol, cyano, amino and nitro;

$Q^{2a}$ and $Q^{2b}$ each independently represent a covalent bond, optionally substituted $C_1$-$C_6$ alkylene or optionally substituted $C_2$-$C_6$ alkenylene, wherein the alkylene or alkenylene may be unsubstituted or substituted with a group selected from $C_1$-$C_6$ alkoxy, halo, hydroxyl, thiol, cyano, amino and nitro; and $R^8$, $R^9$ and $R^{10}$ each independently represent hydrogen or optionally substituted $C_1$-$C_6$ alkyl, wherein the alkyl may be unsubstituted or substituted with a group selected from $C_1$-$C_6$ alkoxy, halo, hydroxyl, thiol, cyano, amino and nitro.

$R^3$ may be substituted with one or more (e.g. one, two, three or four), in particular one or two, substituents independently selected from halo, cyano, oxo, nitro, hydroxyl, —$SR^8$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^{2a}$-$R^{11}$, -$Q^{2a}$-O-$Q^{2b}$-$R^{11}$, -$Q^{2a}$-S-$Q^{2b}$-$R^{11}$, -$Q^{2a}$-SO-$Q^{2b}$-$R^{11}$, -$Q^{2a}$-$NR^8CONR^9R^{10}$, -$Q^{2a}$-$NR^8CONR^9$-$Q^{2a}$-$R^{11}$, -$Q^{2a}$-$NR^8R^9$, -$Q^{2a}$-$NR^8$-$Q^{2b}$-$R^{11}$, -$Q^{2a}$-$COR^8$, -$Q^{2a}$-CO-$Q^{2b}$-$R^{11}$, -$Q^{2a}$-$NR^8COR^9$, -$Q^{2a}$-$NR^8CO$-$Q^{2b}$-$R^{11}$, -$Q^{2a}$-$NR^8C(O)OR^9$, -$Q^{2a}$-$NR^8C(O)O$-$Q^{2b}$-$R^{11}$, -$Q^{2a}$-$SO_2R^8$, -$Q^{2a}$-$SO_2$-$Q^{2b}$-$R^{11}$, -$Q^{2a}$-$CONR^8R^9$, -$Q^{2a}$-$CONR^8$-$Q^{2b}$-$R^{11}$, -$Q^{2a}$-$CO_2R^8$, -$Q^{2a}$-$CO_2$-$Q^{2b}$-$R^{11}$, -$Q^{2a}$-$SO_2NR^8R^9$, -$Q^{2a}$-$SO_2NR^8$-$Q^{2b}$-$R^{11}$, -$Q^{2a}$-$NR^8SO_2R^9$, -$Q^{2a}$-$NR^8SO_2$-$Q^{2b}$-$R^{11}$, -$Q^{2a}$-$NR^8SO_2NR^9R^{10}$ and -$Q^{2a}$-$NR^8SO_2NR^9$-$Q^{2b}$-$R^{11}$, wherein $Q^{2a}$ and $Q^{2b}$ each independently represent a covalent bond, optionally substituted $C_1$-$C_6$ alkylene or optionally substituted $C_2$-$C_6$ alkenylene, wherein $R^8$, $R^9$ and $R^{10}$ each independently represent hydrogen or optionally substituted $C_1$-$C_6$ alkyl, and wherein $R^{11}$ represents an optionally substituted 3 to 10 membered heterocyclyl, heteroaryl, aryl or cycloalkyl, wherein any alkyl, alkoxy, alkenyl, alkynyl, alkylene or alkenylene is optionally substituted with one or more (e.g. one, two, three or four) substituents selected from $C_1$-$C_6$ alkoxy, halo, hydroxyl, thiol, cyano, amino and nitro, and any heterocyclyl, heteroaryl, aryl or cycloalkyl may be unsubstituted or substituted.

In particular, $R^3$ may be substituted with one or more substituents selected from halo (for example, fluoro or chloro), cyano, $C_1$-$C_2$ alkyl (e.g. methyl), —$C_1$-$C_3$ alkoxy (e.g. methoxy or isopropoxy), -$Q^{2a}$-C(O)$NR^8R^9$ wherein $Q^{2a}$ is a covalent bond and $R^8$ and $R^9$ are both hydrogen, wherein the alkyl and alkoxy may be optionally substituted with one or more fluoro.

More particularly, $R^3$ may be substituted with one or more substituents selected from fluoro, chloro, cyano, methyl, $CF_3$, methoxy, isopropoxy and —C(O)$NH_2$.

In particular examples, $R^3$ is substituted with cyano.

$R^3$ may be unsubstituted, mono-substituted or di-substituted.

In certain instances, $R^3$ represents a 3 to 10 membered heterocyclyl, heteroaryl, aryl or cycloalkyl ring selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furanyl, pyrrolyl, oxazolyl, thiazolyl, thiadiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydropyridinyl, quinoxalinyl, dihydrobenzoxazinyl, pyrrolopyridinyl, dihydropyrrolopyridinyl, tetrahydropyridopyrazinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl and tetrahydroisoquinolinyl, which is either unsubstituted or substituted with one or more (e.g. one, two or three) substituents selected from halo, cyano, oxo, nitro, hydroxyl, —$SR^8$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^{2a}$-$R^{11}$, -$Q^{2a}$-O-$Q^{2b}$-$R^{11}$, -$Q^{2a}$-S-$Q^{2b}$-$R^{11}$, -$Q^{2a}$-SO-$Q^{2b}$-$R^{11}$, -$Q^{2a}$-$NR^8CONR^9R^{10}$, -$Q^{2a}$-$NR^8CONR^9$-$Q^{2a}$-$R^{11}$, -$Q^{2a}$-$NR^8R^9$, -$Q^{2a}$-$NR^8$-$Q^{2b}$-$R^{11}$, -$Q^{2a}$-$COR^8$, -$Q^{2a}$-CO-$Q^{2b}$-$R^{11}$, -$Q^{2a}$-$NR^8COR^9$, -$Q^{2a}$-$NR^8CO$-$Q^{2b}$-$R^{11}$, -$Q^{2a}$-$NR^8C(O)OR^9$, -$Q^{2a}$-$NR^8C(O)O$-$Q^{2b}$-$R^{11}$, -$Q^{2a}$-$SO_2R^8$, -$Q^{2a}$-$SO_2$-$Q^{2b}$-$R^{11}$, $Q^{2a}$-$CONR^8R^9$, -$Q^{2a}$-$CONR^8$-$Q^{2b}$-$R^{11}$, -$Q^{2a}$-$CO_2R^8$, -$Q^{2a}$-$CO_2$-$Q^{2b}$-$R^{11}$, -$Q^{2a}$-$SO_2NR^8R^9$, -$Q^{2a}$-$SO_2NR^8$-$Q^{2b}$-$R^{11}$, -$Q^{2a}$-$NR^8SO_2R^9$, -$Q^{2a}$-$NR^8SO_2$-$Q^{2b}$-$R^{11}$, -$Q^{2a}$-$NR^8SO_2NR^9R^{10}$ and -$Q^{2a}$-$NR^8SO_2NR^9$-$Q^{2b}$-$R^{11}$, wherein $Q^{2a}$ and $Q^{2b}$ each independently represent a covalent bond, optionally substituted $C_1$-$C_6$ alkylene or optionally substituted $C_2$-$C_6$ alkenylene, wherein $R^8$, $R^9$ and $R^{10}$ each independently represent hydrogen or optionally substituted $C_1$-$C_6$ alkyl, and wherein $R^{11}$ represents an optionally substituted 3 to 10 membered heterocyclyl, heteroaryl, aryl or cycloalkyl, wherein any alkyl, alkoxy, alkenyl, alkynyl, alkylene or alkenylene is optionally substituted with one or more (e.g. one, two, three or four) substituents selected from $C_1$-$C_6$ alkoxy, halo, hydroxyl, thiol, cyano, amino and nitro, and any heterocyclyl, heteroaryl, aryl or cycloalkyl may be unsubstituted or substituted.

$R^3$ may represent a ring selected from phenyl, pyrazolyl, pyridinyl and indazolyl, wherein the ring is unsubstituted or substituted with one or more, in particular one or two, substituents selected from halo, cyano, oxo, nitro, hydroxyl, —$SR^8$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^{2a}$-$R^{11}$, -$Q^{2a}$-O-$Q^{2b}$-$R^{11}$, -$Q^{2a}$-S-$Q^{2b}$-$R^{11}$, -$Q^{2a}$-SO-$Q^{2b}$-$R^{11}$, -$Q^{2a}$-$NR^8CONR^9R^{10}$, -$Q^{2a}$-$NR^8CONR^9$-$Q^{2a}$-$R^{11}$, -$Q^{2a}$-$NR^8R^9$, -$Q^{2a}$-$NR^8$-$Q^{2b}$-$R^{11}$, -$Q^{2a}$-$COR^8$, -$Q^{2a}$-CO-$Q^{2b}$-$R^{11}$, -$Q^{2a}$-$NR^8COR^9$, -$Q^{2a}$-$NR^8CO$-$Q^{2b}$-$R^{11}$, -$Q^{2a}$-$NR^8C(O)OR^9$, -$Q^{2a}$-$NR^8C(O)O$-$Q^{2b}$-$R^{11}$, -$Q^{2a}$-$SO_2R^8$, -$Q^{2a}$-$SO_2$-$Q^{2b}$-$R^{11}$, -$Q^{2a}$-$CONR^8R^9$, -$Q^{2a}$-$CONR^8$-$Q^{2b}$-$R^{11}$, -$Q^{2a}$-$CO_2R^8$, -$Q^{2a}$-$CO_2$-$Q^{2b}$-$R^{11}$, -$Q^{2a}$-$SO_2NR^8R^9$, -$Q^{2a}$-$SO_2NR^8$-$Q^{2b}$-$R^{11}$, -$Q^{2a}$-$NR^8SO_2R^9$, -$Q^{2a}$-$NR^8SO_2$-$Q^{2b}$-$R^{11}$, -$Q^{2a}$-$NR^8SO_2NR^9R^{10}$ and -$Q^{2a}$-$NR^8SO_2NR^9$-$Q^{2b}$-$R^{11}$, wherein $Q^{2a}$ and $Q^{2b}$ each independently represent a covalent bond, optionally substituted $C_1$-$C_6$ alkylene or optionally substituted $C_2$-$C_6$ alkenylene, wherein $R^8$, $R^9$ and $R^{10}$ each independently represent hydrogen or optionally substituted $C_1$-$C_6$ alkyl, and wherein $R^{11}$ represents an optionally substituted 3 to 10 membered heterocyclyl, heteroaryl, aryl or cycloalkyl, wherein any alkyl, alkoxy, alkenyl, alkynyl, alkylene or alkenylene is optionally substituted with one or more (e.g. one, two, three or four) substituents selected from $C_1$-$C_6$ alkoxy, halo, hydroxyl, thiol, cyano, amino and nitro, and any heterocyclyl, heteroaryl, aryl or cycloalkyl may be unsubstituted or substituted.

$R^3$ may represent a ring selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furanyl, pyrrolyl, oxazolyl, thiazolyl, thiadiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydropyridinyl, quinoxalinyl, dihydrobenzoxazinyl, pyrrolopyridinyl, dihydropyrrolopyridinyl, tetrahydropyridopyrazinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl and tetrahydroisoquinolinyl, wherein the ring is unsubstituted or substituted with one or more (e.g. one, two or three) substituents selected from halo (for example, fluoro or chloro), cyano, $C_1$-$C_2$ alkyl (e.g. methyl), —$C_1$-$C_3$ alkoxy (e.g. methoxy or isopropoxy) and -$Q^{2a}$-C(O)$NR^8R^9$ wherein $Q^{2a}$ is a covalent bond and $R^8$ and $R^9$ are both hydrogen, wherein the alkyl may be optionally substituted with one or more fluoro.

In particular, $R^3$ may be selected from phenyl, pyrazolyl, pyridinyl and indazolyl, wherein the ring is unsubstituted or substituted with one or more (e.g. one, two or three) substituents selected from halo (for example, fluoro or chloro), cyano, $C_1$-$C_2$ alkyl (e.g. methyl), —$C_1$-$C_3$ alkoxy (e.g. methoxy or isopropoxy) and -$Q^{2a}$-C(O)$NR^8R^9$ wherein $Q^{2a}$ is a covalent bond and $R^8$ and $R^9$ are both hydrogen, wherein the alkyl may be optionally substituted with one or more fluoro.

The present invention further relates to compounds of formula (I), a tautomer thereof, or a pharmaceutically acceptable salt of said compound or tautomer, wherein:
X represents O, N($R^h$) or $CH_2$;
$R^a$ represents hydrogen or fluoro;
$R^b$, $R^c$, $R^d$ and $R^e$ are each hydrogen;
$R^f$ and $R^g$ each independently represent hydrogen or fluoro;
when X is O or N($R^h$), neither of $R^a$, $R^f$ or $R^g$ represent fluoro;
$R^h$ represents methyl, C(O)Me, S(O)$_2$Me or phenyl;
$R^1$ represents hydrogen or optionally substituted $C_1$-$C_3$ alkyl;
$R^2$ represents a 5 to 10 membered monocyclic or bicyclic optionally substituted heteroaryl or aryl ring, or a 3 to 10 membered monocyclic or bicyclic substituted heterocyclyl or cycloalkyl ring; or
$R^1$ and $R^2$ together form a 5 to 10 membered monocyclic or bicyclic optionally substituted heteroaryl ring, or a 4 to 10 membered monocyclic or bicyclic substituted heterocyclyl ring;
and when substituted, the heterocyclyl, cycloalkyl, aryl or heteroaryl ring, may be substituted with one, two or three of -$Q^1$($R^3$)$_n$, wherein each -$Q^1$-($R^3$)$_n$ is the same or different;
n is 0 or 1;
$Q^1$ and $R^3$ are as defined herein.

In particular, $Q^1$ represents $Q^{1a}$ or $Q^{1b}$. $Q^{1a}$ substituents are independently selected from halo, cyano, nitro, hydroxyl, —$SR^4$, —$NR^4R^5$, —$CONR^4R^5$, —$C_0$-$C_3$-alkylene-$NR^4COR^5$, —$NR^4CONR^5R^6$, —$COR^4$, —C(O)$OR^4$, —$SO_2R^4$, —$SO_2NR^4R^5$, —$NR^4SO_2R^5$, —$NR^4SO_2NR^5R^6$, —$NR^4C(O)OR^5$, optionally substituted —$C_1$-$C_6$ alkyl, optionally substituted $C_1$-$C_6$ alkoxy, and optionally substituted —$C_2$-$C_6$ alkenyl, and $Q^{1b}$ substituents are independently selected from a covalent bond, an oxygen atom, a sulfur atom, —$OR^7$—, —SO—, —$SO_2$—, —CO—, —C(O)O—, —$C_0$-$C_3$-alkylene-C(O)$NR^4$—$C_0$-$C_3$ alkylene, —$C_0$-$C_3$-alkylene-$NR^4$—$C_0$-$C_3$ alkylene, —$C_0$-$C_3$-alkylene-$NR^4$C(O)—$C_0$-$C_3$ alkylene, —$NR^4CONR^5$—, —$SO_2NR^4$—, $NR^4SO_2$—, —$NR^4SO_2NR^5$—, —$NR^4C(O)$ O—, —$NR^4C(O)OR^7$—, optionally substituted $C_1$-$C_6$ alkylene, and optionally substituted —$C_2$-$C_6$ alkenylene.

The alkyl, alkoxy, alkenyl, alkylene or alkenylene may be unsubstituted or substituted with one or more substituents selected from $C_1$-$C_6$ alkoxy, halo, hydroxyl, thiol, cyano, amino and nitro, and wherein $R^4$, $R^5$, $R^6$ and $R^7$ are as defined herein; and $R^3$ is a 5 or 6 membered heteroaryl, heterocyclyl, cycloalkyl or aryl ring optionally substituted with one or two substituents independently selected from halo, cyano, oxo, nitro, hydroxyl, —$SR^8$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl, -$Q^{2a}$-$R^{11}$, -$Q^{2a}$O-$Q^{2b}$-$R^{11}$, -$Q^{2a}$-S-$Q^{2b}$-$R^{11}$, -$Q^{2a}$-SO-$Q^{2b}$-$R^{11}$, -$Q^{2a}$-$NR^8CONR^9R^{10}$, -$Q^{2a}$-$NR^8CONR^9$-$Q^{2a}$-$R^{11}$, -$Q^{2a}$-$NR^8R^9$, -$Q^{2a}$-$NR^8$-$Q^{2b}$-$R^{11}$, -$Q^{2a}$-$COR^8$, -$Q^{2a}$-CO-$Q^{2b}$-$R^{11}$, -$Q^{2a}$-$NR^8COR^9$, -$Q^{2a}NR^8CO$-$Q^{2b}$-$R^{11}$, -$Q^{2a}$-$NR^8C(O)OR^9$, -$Q^{2a}$-$NR^8C(O)$ O-$Q^{2b}$-$R^{11}$, -$Q^{2a}$-$SO_2R^8$, -$Q^{2a}$-$SO_2$-$Q^{2b}$-$R^{11}$, -$Q^{2a}$-$CONR^8R^9$, -$Q^{2a}$-$CONR^8$-$Q^{2b}$-$R^{11}$, -$Q^{2a}$-$CO_2R^8$, -$Q^{2a}$-$CO_2$-$Q^{2b}$-$R^{11}$, -$Q^{2a}$-$SO_2NR^8R^9$, -$Q^{2a}$-$SO_2NR^8$-$Q^{2b}$-$R^{11}$, -$Q^{2a}$—$NR^8SO_2R^9$, -$Q^{2a}$-$NR^8SO_2$-$Q^{2b}$-$R^{11}$, -$Q^{2a}$-$NR^8SO_2NR^9R^{10}$ and -$Q^{2a}$-$NR^8SO_2NR^9$-$Q^{2b}$-$R^{11}$, wherein $Q^{2a}$ and $Q^{2b}$ each independently represent a covalent bond, optionally substituted $C_1$-$C_6$ alkylene or optionally substituted $C_2$-$C_6$ alkenylene, wherein $R^8$, $R^9$ and $R^{10}$ each independently represent hydrogen or optionally substituted $C_1$-$C_6$ alkyl, and wherein $R^{11}$ represents an optionally substituted $C_3$-$C_4$ heterocyclyl, wherein any alkyl, alkoxy, alkenyl, alkynyl, alkylene or alkenylene is optionally substituted with one or more (e.g. one, two, three or four) substituents selected from $C_1$-$C_6$ alkoxy, halo, hydroxyl, thiol, cyano, amino and nitro, and the $C_3$-$C_4$ heterocyclyl may be unsubstituted or substituted with a substituent selected from $C_1$-$C_3$ alkyl, $C_1$-$C_3$ alkoxy, halo, cyano, oxo, nitro, amino, amido, hydroxyl, nitro, $C_1$-$C_6$ alkyl or $C_1$-$C_3$ alkyl, $C_1$-$C_6$ alkoxy or $C_1$-$C_3$ alkoxy, wherein the alkyl and alkoxy may be optionally substituted with halo.

The present invention further relates to compounds of formula (I), a tautomer thereof, or a pharmaceutically acceptable salt of said compound or tautomer, wherein:
X represents O, N($R^h$) or $CH_2$;
$R^a$, $R^f$ and $R^g$ each independently represent hydrogen or fluoro;
$R^b$, $R^c$, $R^d$ and $R^e$ are each hydrogen;
when X is O or N($R^h$), neither of $R^a$, $R^f$ or $R^g$ represent fluoro;
$R^h$ represents methyl, C(O)Me, S(O)$_2$Me or phenyl;
$R^1$ represents hydrogen or optionally substituted $C_1$-$C_3$ alkyl;
$R^2$ represents a 5 to 10 membered monocyclic or bicyclic optionally substituted heteroaryl or aryl ring, or a 3 to 10 membered monocyclic or bicyclic substituted heterocyclyl or cycloalkyl ring; or
$R^1$ and $R^2$ together form a 5 to 10 membered monocyclic or bicyclic optionally substituted heteroaryl ring, or a 4 to 10 membered monocyclic or bicyclic substituted heterocyclyl ring, and when substituted, may be substituted with one, two or three of $Q^1$($R^3$)$_n$, wherein each -$Q^1$-($R^3$)$_n$ is the same or different;
n is 0 or 1;
$Q^1$ represents $Q^{1a}$ or $Q^{1b}$;
$Q^{1a}$ is an optionally substituted $C_1$-$C_3$ alkoxy;
$Q^{1b}$ is a covalent bond;
$R^3$ represents substituted or unsubstituted phenyl, pyrazolyl, pyridinyl or indazolyl.

In a preferred embodiment of the invention there is provided a compound of formula (I), a tautomer thereof, or a pharmaceutically acceptable salt of said compound or tautomer, wherein:
X is selected from O, N($R^h$), and C($R^i$)($R^j$);
$R^a$ is selected from hydrogen, fluoro, $C_1$-$C_3$ alkyl, and $C_1$-$C_3$ alkoxy; or $R^a$ is linked to $R^b$ or $R^j$ to form an $C_3$-$C_4$ cycloalkyl ring;
$R^b$, $R^c$, $R^d$, and $R^e$, are each independently selected from hydrogen, $C_1$-$C_3$ alkyl, and one or more spirocyclic groups where $R^b$ is linked to $R^c$ or $R^d$ is linked to $R^e$ to form a $C_3$-$C_4$ cycloalkyl, or $R^b$ is linked to $R^a$ or $R^e$ is linked to $R^f$ to form an optionally substituted $C_3$-$C_4$ cycloalkyl;
$R^f$ and $R^g$ are each independently selected from hydrogen, fluoro, cyano, $C_1$-$C_3$ alkyl, $C_1$-$C_3$ alkoxy, and one or more spirocyclic groups where $R^f$ is linked to $R^g$ to form a $C_3$-$C_4$ cycloalkyl ring, or $R^f$ is linked to $R^e$ or $R^g$ is linked to $R^j$ to form an optionally substituted $C_3$-$C_4$ cycloalkyl;
when X is O or N($R^h$), neither of $R^a$, $R^f$ or $R^g$, is fluoro or optionally substituted $C_1$-$C_3$ alkoxy;

$R^h$ is selected from hydrogen, $C_1$-$C_3$ alkyl, C(O)R', S(O)$_2$R', and a 3 to 6 membered heterocyclyl, heteroaryl, cycloalkyl or aryl ring via a $C_0$-$C_3$ alkylene linker;

R' is selected from $C_1$-$C_3$ alkyl, and a 3 to 6 membered heterocyclyl, heteroaryl, cycloalkyl or aryl ring;

$R^i$ and $R^j$ are each independently selected from hydrogen, fluoro, cyano, $C_1$-$C_3$ alkyl, $C_1$-$C_3$ alkoxy, a 3 to 6 membered heterocyclyl, heteroaryl, cycloalkyl or aryl ring, and a spirocyclic group where $R^i$ is linked to $R^j$ or $R^j$ is linked to $R^g$ or $R^a$ to form an optionally substituted $C_3$-$C_4$ cycloalkyl;

$R^1$ is selected from hydrogen and $C_1$-$C_3$ alkyl;

$R^2$ is selected from a 5 to 10 membered, monocyclic or bicyclic, optionally substituted heteroaryl or aryl ring, and a 3 to 10 membered, monocyclic or bicyclic, substituted heterocyclyl or cycloalkyl ring; or $R^1$ and $R^2$ together form a 5 to 10 membered, monocyclic or bicyclic, optionally substituted heteroaryl ring, or a 4 to 10 membered, monocyclic or bicyclic, substituted heterocyclyl ring;

wherein $R^2$, or the ring formed by $R^1$ together with $R^2$, when substituted, is substituted with one or more -Q$^1$(R$^3$), which may be the same or different, wherein:

n is 0 or 1;

$Q^1$ represents $Q^{1a}$ or $Q^{1b}$; wherein $Q^{1a}$ is selected from halo, cyano, nitro, hydroxyl, —SR$^4$, —NR$^4$R$^5$, —CONR$^4$R$^5$, —$C_0$-$C_3$-alkylene-NR$^4$COR$^5$, —NR$^4$CONR$^5$R$^6$, —COR$^4$, —C(O)OR$^4$, —SO$_2$R$^4$, —SO$_2$NR$^4$R$^5$, —NR$^4$SO$_2$R$^5$, —NR$^4$SO$_2$NR$^5$R$^6$, —NR$^4$C(O)OR$^5$, —$C_1$-$C_6$ alkyl, $C_1$-$C_6$ alkoxy, and —$C_2$-$C_6$ alkenyl;

$Q^{1b}$ is selected from a covalent bond, an oxygen atom, a sulfur atom, —OR$^7$—, —SO—, —SO$_2$—, —CO—, —C(O)O—, —$C_0$-$C_3$-alkylene-C(O)NR$^4$—$C_0$-$C_3$ alkylene, —$C_0$-$C_3$-alkylene-NR$^4$—$C_0$-$C_3$ alkylene, —$C_0$-$C_3$-alkylene-NR$^4$C(O)—$C_0$-$C_3$ alkylene, —NR$^4$CONR$^5$—, —SO$_2$NR$^4$—, NR$^4$SO$_2$—, —NR$^4$SO$_2$NR$^5$—, —NR$^4$C(O)O—, —NR$^4$C(O)OR$^7$—, $C_1$-$C_6$ alkylene, and —$C_2$-$C_6$ alkenylene;

$R^3$ is a 3 to 10 membered monocyclic or bicyclic heterocyclyl, heteroaryl, cycloalkyl or aryl ring;

$R^4$, $R^5$ and $R^6$ are each independently selected from hydrogen and $C_1$-$C_6$ alkyl;

$R^7$ is $C_1$-$C_6$ alkylene;

wherein $R^3$ is optionally substituted with one or more substituents independently selected from halo, cyano, oxo, nitro, hydroxyl, —SR$^8$, —$C_1$-$C_6$ alkyl, —$C_1$-$C_6$ alkoxy, —$C_2$-$C_6$ alkenyl, —$C_2$-$C_6$ alkynyl, -Q$^{2a}$-R$^{11}$, -Q$^{2a}$-O-Q$^{2b}$-R$^{11}$, -Q$^{2a}$-S-Q$^{2b}$-R$^{11}$, -Q$^{2a}$-SO-Q$^{2b}$-R$^{11}$, -Q$^{2a}$-NR$^8$CONR$^9$R$^{10}$, -Q$^{2a}$-NR$^8$CONR$^9$-Q$^{2b}$-R$^{11}$, -Q$^{2a}$-NR$^8$R$^9$, -Q$^{2a}$-NR$^8$-Q$^{2b}$-R$^{11}$, -Q$^{2a}$-COR$^8$, -Q$^{2a}$-CO-Q$^{2b}$-R$^{11}$, -Q$^{2a}$-NR$^8$COR$^9$, -Q$^{2a}$-NR$^8$CO-Q$^{2b}$-R$^{11}$, -Q$^{2a}$-NR$^8$C(O)OR$^9$, -Q$^{2a}$-NR$^8$C(O)O-Q$^{2b}$-R$^{11}$, -Q$^{2a}$-SO$_2$R$^8$, -Q$^{2a}$-SO$_2$-Q$^{2b}$-R$^{11}$, $Q^{2a}$-CONR$^8$R$^9$, -Q$^{2a}$-CONR$^8$-Q$^{2b}$-R$^{11}$, -Q$^{2a}$-CO$_2$R$^8$, -Q$^{2a}$-CO$_2$-Q$^{2b}$-R$^{11}$, -Q$^{2a}$-SO$_2$NR$^8$R$^9$, -Q$^{2a}$-SO$_2$NR$^8$-Q$^{2b}$-R$^{11}$, -Q$^{2a}$-NR$^8$SO$_2$R$^9$, -Q$^{2a}$-NR$^8$SO$_2$-Q$^{2b}$-R$^{11}$, -Q$^{2a}$-NR$^8$SO$_2$NR$^9$R$^{10}$ and -Q$^{2a}$-NR$^8$SO$_2$NR$^9$-Q$^{2b}$-R$^{11}$;

wherein $Q^{2a}$ and $Q^{2b}$ each independently represent a covalent bond, $C_1$-$C_6$ alkylene or $C_2$-$C_6$ alkenylene;

$R^8$, $R^9$ and $R^{19}$ are each independently selected from hydrogen and $C_1$-$C_6$ alkyl;

$R^{11}$ is a 3 to 10 membered heterocyclyl, heteroaryl, aryl or cycloalkyl; and each heteroaryl or heterocyclyl ring comprises one to five, preferably one to three, heteroatoms independently selected from nitrogen, oxygen and sulfur.

Preferably, $R^a$ is selected from hydrogen, fluoro, $C_1$-$C_3$ alkyl, and $C_1$-$C_3$ alkoxy.

Preferably, $R^b$, $R^c$, $R^d$, and $R^e$, are each independently selected from hydrogen and $C_1$-$C_3$ alkyl.

Preferably, $R^f$ and $R^g$ are each independently selected from hydrogen, fluoro, cyano, $C_1$-$C_3$ alkyl, and $C_1$-$C_3$ alkoxy.

Preferably, $R^h$ is selected from hydrogen, $C_1$-$C_3$ alkyl, C(O)R', S(O)$_2$R', and phenyl.

Preferably, R' is $C_1$-$C_3$ alkyl.

Preferably, $R^i$ and $R^j$ are each independently selected from hydrogen, fluoro, cyano, $C_1$-$C_3$ alkyl, $C_1$-$C_3$ alkoxy, and phenyl.

In a preferred embodiment of a preferred aspect of the invention where X represents oxygen, the present invention provides a compound of formula (I), which is a compound of formula (IA):

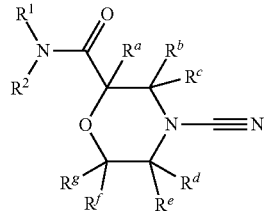

(IA)

a tautomer thereof, or a pharmaceutically acceptable salt of said compound or tautomer, wherein:

$R^a$, $R^b$, $R^c$, $R^d$, $R^e$, $R^f$ and $R^g$, are each independently selected from hydrogen and $C_1$-$C_3$ alkyl; and preferably, are each independently selected from hydrogen and methyl;

$R^1$ is selected from hydrogen and $C_1$-$C_3$ alkyl;

$R^2$ is selected from a 5 to 10 membered, monocyclic or bicyclic, optionally substituted heteroaryl or aryl ring, and a 3 to 10 membered, monocyclic or bicyclic, substituted heterocyclyl or cycloalkyl ring; or $R^1$ and $R^2$ together form a 5 to 10 membered, monocyclic or bicyclic, optionally substituted heteroaryl ring, or a 4 to 10 membered, monocyclic or bicyclic, substituted heterocyclyl ring;

each heteroaryl or heterocyclyl ring comprises one to three heteroatoms independently selected from nitrogen, oxygen and sulfur;

wherein $R^2$, or the ring formed by $R^1$ together with $R^2$, when substituted, is substituted with one or more -Q$^1$(R$^3$)$_n$ which may be the same or different; and $Q^1$, $R^3$, and n are as herein defined.

In a preferred embodiment of a preferred aspect of the invention where X represents N(R$^h$), the present invention provides a compound of formula (I), which is a compound of formula (IB):

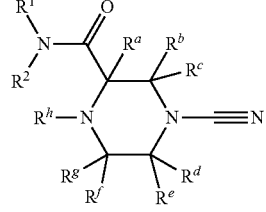

(IB)

a tautomer thereof, or a pharmaceutically acceptable salt of said compound or tautomer, wherein:

$R^a$, $R^b$, $R^c$, $R^d$, $R^e$, $R^f$ and $R^g$, are each independently selected from hydrogen and $C_1$-$C_3$ alkyl; and preferably, are each independently selected from hydrogen and methyl;

$R^h$ is selected from hydrogen, $C_1$-$C_3$ alkyl, $C(O)(C_1$-$C_3)$ alkyl, $S(O)_2(C_1$-$C_3)$alkyl, and phenyl;

$R^1$ is selected from hydrogen and $C_1$-$C_3$ alkyl;

$R^2$ is selected from a 5 to 10 membered, monocyclic or bicyclic, optionally substituted heteroaryl or aryl ring, and a 3 to 10 membered, monocyclic or bicyclic, substituted heterocyclyl or cycloalkyl ring; or $R^1$ and $R^2$ together form a 5 to 10 membered, monocyclic or bicyclic, optionally substituted heteroaryl ring, or a 4 to 10 membered, monocyclic or bicyclic, substituted heterocyclyl ring; and each heteroaryl or heterocyclyl ring comprises one to three heteroatoms independently selected from nitrogen, oxygen and sulfur;

wherein $R^2$, or the ring formed by $R^1$ together with $R^2$, when substituted, is substituted with one or more -$Q^1(R^3)_n$ which may be the same or different; and $Q^1$, $R^3$, and n are as herein defined.

In a preferred embodiment of a preferred aspect of the invention where X represents $C(R^i)(R^j)$, the present invention provides a compound of formula (I), which is a compound of formula (IC):

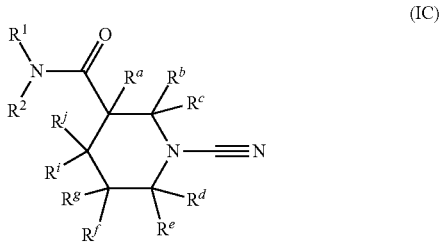

(IC)

a tautomer thereof, or a pharmaceutically acceptable salt of said compound or tautomer, wherein:

$R^a$ is selected from hydrogen, fluoro, $C_1$-$C_3$ alkyl, and $C_1$-$C_3$ alkoxy;

$R^b$, $R^c$, $R^d$, and $R^e$, are each independently selected from hydrogen and $C_1$-$C_3$ alkyl;

and preferably, are each independently selected from hydrogen and methyl;

$R^f$, $R^g$, $R^i$, and $R^j$, are each independently selected from hydrogen, fluoro, cyano, $C_1$-$C_3$ alkyl, $C_1$-$C_3$ alkoxy, and phenyl;

$R^1$ is selected from hydrogen and $C_1$-$C_3$ alkyl;

$R^2$ is selected from a 5 to 10 membered, monocyclic or bicyclic, optionally substituted heteroaryl or aryl ring, and a 3 to 10 membered, monocyclic or bicyclic, substituted heterocyclyl or cycloalkyl ring; or $R^1$ and $R^2$ together form a 5 to 10 membered, monocyclic or bicyclic, optionally substituted heteroaryl ring, or a 4 to 10 membered, monocyclic or bicyclic, substituted heterocyclyl ring; and each heteroaryl or heterocyclyl ring comprises one to three heteroatoms independently selected from nitrogen, oxygen and sulfur;

wherein $R^2$, or the ring formed by $R^1$ together with $R^2$, when substituted, is substituted with one or more -$Q^1(R^3)_n$ which may be the same or different; and $Q^1$, $R^3$, and n are as herein defined.

Preferred embodiments of the compound of formula (I) as defined herein in respect of the first aspect of the invention, preferred aspects thereof, including the compounds of formulae (IA), (IB), and (IC), and preferred embodiments thereof in respect of the substituents X, $R^a$, $R^b$, $R^c$, $R^d$, $R^e$, $R^f$ and $R^g$, may, additionally, preferentially comprise $R^1$ and $R^2$ as defined above.

In a preferred aspect of the compounds of formula (I) of the present invention, in particular, (IA), (IB) and (IC):

$R^1$ is selected from hydrogen and $C_1$-$C_3$ alkyl; and $R^2$ is selected from a 5 to 10 membered, monocyclic or bicyclic, heteroaryl or aryl ring; or $R^1$ and $R^2$ together form a 5 to 10 membered, monocyclic or bicyclic, heteroaryl ring;

wherein each heteroaryl ring comprises one to three heteroatoms independently selected from nitrogen, oxygen and sulfur;

wherein $R^2$, or the ring formed by $R^1$ together with $R^2$, is optionally substituted with one to four, preferably one or two, $Q^{1a}$ groups, each independently selected from halo, cyano, $C_1$-$C_3$ alkyl and $C_1$-$C_3$ alkoxy. More preferably $Q^{1a}$ is selected from halo, cyano, methyl, ethyl, propyl, methoxy, ethoxy and propoxy. Most preferably $Q^{1a}$ is n-propoxy.

In another preferred aspect of the compounds of formula (I), in particular, (IA), (IB) and (IC):

$R^1$ is selected from hydrogen and $C_1$-$C_3$ alkyl; and $R^2$ is selected from a 5 to 10 membered, monocyclic or bicyclic, heteroaryl or aryl ring, and a 3 to 10 membered, monocyclic or bicyclic, heterocyclyl or cycloalkyl ring; or $R^1$ and $R^2$ together form a 5 to 10 membered, monocyclic or bicyclic, heteroaryl ring;

wherein $R^2$, or the ring formed by $R^1$ together with $R^2$, is substituted with one to four, preferably one or two, $R^3$ groups, each independently selected;

$R^3$ is as defined herein;

each heteroaryl or heterocyclyl ring comprises one to three heteroatoms independently selected from nitrogen, oxygen and sulfur;

wherein $R^2$, or the ring formed by $R^1$ together with $R^2$, is optionally further substituted with one to four, preferably one or two, $Q^{1a}$ groups, each independently selected from halo, cyano, $C_1$-$C_3$ alkyl and $C_1$-$C_3$ alkoxy. More preferably $Q^{1a}$ is selected from halo, cyano, methyl, ethyl, propyl, methoxy, ethoxy and propoxy. Most preferably $Q^{1a}$ is n-propoxy.

Preferred embodiments of the compound of formula (I) as defined herein in respect of the above-mentioned aspects of the invention, in particular, the preferred aspects of (IA), (IB) and (IC) may, additionally, comprise the preferred embodiments of $R^2$ and $R^3$ as defined below.

Preferably, the heteroaryl ring of $R^2$ is a 5 or 6-membered monocyclic heteroaryl, or a 9 or 10-membered bicyclic heteroaryl ring, each comprising one to five, preferably one to three, heteroatoms independently selected from nitrogen, oxygen and sulfur. For example, the ring may comprise 1 oxygen atom. Alternatively, the ring may comprise 1 sulfur atom. Alternatively, the ring may comprise 1, 2, 3 or 4 nitrogen atoms. Alternatively, the ring may comprise 1 or 2 nitrogen atoms and an oxygen atom. Alternatively, the ring may comprise 1 or 2 nitrogen atoms and a sulfur atom.

Preferably, the heterocyclyl ring of $R^2$ is a 4 to 8-membered monocyclic heterocyclyl, or an 8 to 10-membered bicyclic heterocyclyl ring, each comprising one to five, preferably one to three, heteroatoms independently selected from nitrogen, oxygen and sulfur. More preferably, the heterocyclyl ring of $R^2$ is a 4, 5, 6 or 7-membered monocyclic heterocyclyl, or a 9 or 10-membered bicyclic heterocyclyl ring, each comprising one to three heteroatoms independently selected from nitrogen, oxygen and sulfur. For example, the ring may comprise 1 or 2 oxygen atoms. Alternatively, the ring may comprise 1 or 2 sulfur atoms. Alternatively, the ring may comprise 1 or 2 nitrogen atoms. Alternatively, the ring may comprise 1 nitrogen atom and an oxygen atom. Alternatively, the ring may comprise 1 nitrogen atom and a sulfur atom. Alternatively, the ring may comprise 1 oxygen atom and a sulfur atom.

Preferably, the aryl ring of $R^2$ is phenyl, or an 8 to 10-membered aryl. More preferably, the aryl ring of $R^2$ is selected from phenyl, indanyl, tetralinyl, and naphthyl. Most preferably, the aryl ring phenyl.

Preferably, the cycloalkyl ring of $R^2$ is a 4 to 7-membered monocyclic, or an 8 to 10-membered bicyclic cycloalkyl. More preferably, the cycloalkyl ring of $R^2$ is selected from cyclobutyl, cyclopentyl, cyclohexyl, and decalin.

More preferably, the heterocyclyl, heteroaryl, cycloalkyl and aryl ring of $R^2$ is selected from pyridinyl, pyrazinyl, pyrimidinyl, pyridazinyl, furanyl, pyrrolyl, oxazolyl, thiazolyl, thiadiazolyl, pyrazolyl, triazolyl, tetrazolyl, indolyl, indolinyl, indolizinyl, isoindolyl, isoindolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, quinoxalinyl, dihydrobenzoxazinyl, pyrrolopyridinyl, tetrahydropyridopyrazinyl, phenyl, naphthyl, naphthalenyl, dihydropyrrolopyridinyl, cyclopropyl, cyclobutyl, cyclopentyl, cyclohexyl, cycloheptyl, cyclooctyl, decahydronaphthalenyl, bicycloheptane, bicyclooctane, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, and tetrahydroisoquinolinyl.

More preferably, the heterocyclyl, heteroaryl, cycloalkyl and aryl ring of $R^2$ is selected from pyridinyl, thiazolyl, thiadiazolyl, isoquinolinyl, phenyl, isoxazolyl, benzothiazolyl, pyrimidinyl, imidazolyl, pyrazolyl, pyridazinyl, pyrrolidinyl, pyrazinyl, and oxazolyl.

Preferably, the heteroaryl ring formed by $R^1$ together with $R^2$ is a 5 or 6-membered monocyclic heteroaryl, or a 9 or 10-membered bicyclic heteroaryl ring, each comprising one to five, preferably one to three, heteroatoms independently selected from nitrogen, oxygen and sulfur, at least one of which is nitrogen. For example, the ring may comprise 1, 2, 3 or 4 nitrogen atoms. Alternatively, the ring may comprise 1 or 2 nitrogen atoms and an oxygen atom. Alternatively, the ring may comprise 1 or 2 nitrogen atoms and a sulfur atom.

Preferably, the heterocyclyl ring formed by $R^1$ together with $R^2$ is a 4 to 8-membered monocyclic heterocyclyl, or an 8 to 10-membered bicyclic heterocyclyl ring, each comprising one to five, preferably one to three, heteroatoms independently selected from nitrogen, oxygen and sulfur, at least one of which is nitrogen. More preferably, the heterocyclyl ring of $R^2$ is a 4, 5, 6 or 7-membered monocyclic heterocyclyl, or a 9 or 10-membered bicyclic heterocyclyl ring, each comprising one to three heteroatoms independently selected from nitrogen, oxygen and sulfur, at least one of which is nitrogen. For example, the ring may comprise 1 or 2 nitrogen atoms. Alternatively, the ring may comprise 1 nitrogen atom and an oxygen atom. Alternatively, the ring may comprise 1 nitrogen atom and a sulfur atom.

Preferably, the ring formed by $R^1$ together with $R^2$ is selected from the group consisting of pyridinyl, pyrazinyl, pyrimidinyl, pyridazinyl, pyrrolyl, oxazolyl, thiazolyl, thiadiazolyl, pyrazolyl, triazolyl, tetrazolyl, indolyl, indolinyl, indolizinyl, isoindolyl, isoindolinyl, purinyl, furazanyl, imidazolyl, indazolyl, isothiazolyl, isoxazolyl, oxadiazolyl, tetrazolyl, thiadiazolyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, quinoxalinyl, dihydrobenzoxazinyl, pyrrolopyridinyl, dihydropyrrolopyridinyl, tetrahydropyridopyrazinyl, azetidinyl, pyrrolidinyl, piperidinyl, azepanyl, diazepanyl, morpholinyl, oxazolidinyl, oxazinanyl, piperazinyl, thiomorpholinyl, homopiperazinyl, hexahydropyrimidinyl, pyrazolinyl, pyrazolidinyl, 4H-quinolizinyl, quinuclidinyl, tetrahydropyridinyl, tetrahydropyrimidinyl, thiazolidinyl, tetrahydroquinolinyl, and tetrahydroisoquinolinyl.

More preferably, the ring formed by $R^1$ together with $R^2$ is dihydropyrrolopyridinyl (e.g. 2,3-dihydro-1H-pyrrolo[2,3-b]pyridine).

Preferably, each $R^3$ is independently selected from a 3 to 10 membered monocyclic or bicyclic heterocyclyl, heteroaryl, cycloalkyl or aryl ring;
wherein each heteroaryl or heterocyclyl ring comprises one to three heteroatoms independently selected from nitrogen, oxygen and sulfur;
said ring is optionally substituted with one to four, preferably one or two groups, each independently selected from halo, cyano, oxo, nitro, hydroxyl, $C_1$-$C_6$ alkyl, $C_1$-$C_6$ alkoxy, and $CONR^8R^9$;
$R^8$ and $R^9$ are each independently selected from hydrogen and $C_1$-$C_3$ alkyl, and are preferably each hydrogen; and
said alkyl and alkoxy groups are optionally substituted by one or more halo groups, preferably one or more fluoro.

More preferably, each $R^3$ is independently selected from a 3 to 10 membered monocyclic or bicyclic heterocyclyl, heteroaryl, cycloalkyl or aryl ring;
wherein each heteroaryl or heterocyclyl ring comprises one to three heteroatoms independently selected from nitrogen, oxygen and sulfur; and
said ring is optionally substituted with one to four, preferably one or two groups, each independently selected from fluoro, chloro, cyano, methyl, methoxy, isopropoxy, trifluoromethyl, trifluoromethoxy, and $CONH_2$.

Preferably, the heteroaryl ring of $R^3$ is a 5 or 6-membered monocyclic heteroaryl, or a 9 or 10-membered bicyclic heteroaryl ring, each comprising one to five, preferably one to three, heteroatoms independently selected from nitrogen, oxygen and sulfur. For example, the ring may comprise 1 oxygen atom. Alternatively, the ring may comprise 1 sulfur atom. Alternatively, the ring may comprise 1, 2, 3 or 4 nitrogen atoms. Alternatively, the ring may comprise 1 or 2 nitrogen atoms and an oxygen atom. Alternatively, the ring may comprise 1 or 2 nitrogen atoms and a sulfur atom.

Preferably, the heterocyclyl ring of $R^3$ is a 4 to 8-membered monocyclic heterocyclyl, or an 8 to 10-membered bicyclic heterocyclyl ring, each comprising one to five, preferably one to three, heteroatoms independently selected from nitrogen, oxygen and sulfur. More preferably, the heterocyclyl ring of $R^3$ is a 4, 5, 6 or 7-membered monocyclic heterocyclyl, or a 9 or 10-membered bicyclic heterocyclyl ring, each comprising one to three heteroatoms independently selected from nitrogen, oxygen and sulfur. For example, the ring may comprise 1 or 2 oxygen atoms. Alternatively, the ring may comprise 1 or 2 sulfur atoms. Alternatively, the ring may comprise 1 or 2 nitrogen atoms. Alternatively, the ring may comprise 1 nitrogen atom and an oxygen atom. Alternatively, the ring may comprise 1 nitrogen atom and a sulfur atom. Alternatively, the ring may comprise 1 oxygen atom and a sulfur atom.

Preferably, the aryl ring of $R^3$ is phenyl, or an 8 to 10-membered aryl. For example, the aryl ring of $R^3$ is selected from phenyl, indanyl, tetralinyl, and naphthyl. Most preferably, the aryl ring phenyl.

Preferably, the cycloalkyl ring of $R^3$ is a 4 to 7-membered monocyclic, or an 8 to 10-membered bicyclic cycloalkyl. For example, the cycloalkyl ring of $R^3$ is selected from cyclobutyl, cyclopentyl, cyclohexyl, and decalin.

Preferably, each heterocyclyl, heteroaryl, cycloalkyl and aryl ring of $R^3$ is independently selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furanyl, pyrrolyl, oxazolyl, thiazolyl, thiadiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydropyridinyl, quinoxalinyl, dihydrobenzoxazinyl, pyrrolopyridinyl, dihydropyrrolopyridinyl, tetrahydropyridopyrazinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, and tetrahydroisoquinolinyl.

More preferably, each heterocyclyl, heteroaryl, cycloalkyl and aryl ring of $R^3$ is independently selected from phenyl, pyridinyl, pyrazinyl, pyrazolyl, indazolyl, and pyrazolopyridinyl (e.g. pyrazolo[3,4-c]pyridinyl and pyrazolo[4,3-d]pyridinyl).

In one particularly preferred aspect of the invention, where X represents oxygen, there is provided a compound of formula (IA):

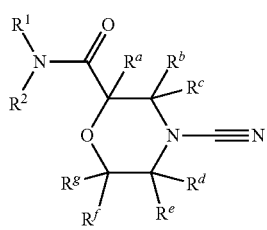

a tautomer thereof, or a pharmaceutically acceptable salt of said compound or tautomer, wherein:

$R^a$, $R^b$, $R^c$, $R^d$, $R^e$, $R^f$ and $R^g$, are each independently selected from hydrogen and methyl;
$R^1$ is selected from hydrogen and methyl;
$R^2$ is selected from a 5 to 10 membered, monocyclic or bicyclic, heteroaryl or aryl ring; or
$R^1$ and $R^2$ together form a 5 to 10 membered, monocyclic or bicyclic, heteroaryl ring; each heteroaryl ring comprises one to three heteroatoms independently selected from nitrogen, oxygen and sulfur;
wherein $R^2$, or the ring formed by $R^1$ together with $R^2$, is optionally substituted with one to four, preferably one or two, groups independently selected from halo, cyano, methyl, ethyl, propyl, methoxy, ethoxy and propoxy.

In another particularly preferred aspect of the invention, where X represents oxygen, there is provided a compound of formula (IA):

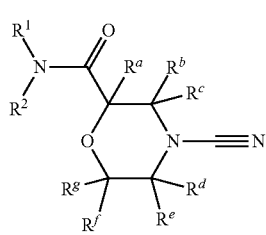

a tautomer thereof, or a pharmaceutically acceptable salt of said compound or tautomer, wherein:
$R^a$, $R^b$, $R^c$, $R^d$, $R^e$, $R^f$ and $R^g$, are each independently selected from hydrogen and methyl;
$R^1$ is selected from hydrogen and methyl;
$R^2$ is selected from a 5 to 10 membered, monocyclic or bicyclic, heteroaryl or aryl ring, and a 3 to 10 membered, monocyclic or bicyclic, heterocyclyl or cycloalkyl ring; or
$R^1$ and $R^2$ together form a 5 to 10 membered, monocyclic or bicyclic, heteroaryl ring;
wherein $R^2$, or the ring formed by $R^1$ together with $R^2$, is substituted with one to four, preferably one or two, $R^3$ groups;
wherein $R^2$, or the ring formed by $R^1$ together with $R^2$, is optionally further substituted with one to four, preferably one or two groups, each independently selected from fluoro, chloro, cyano, methyl, methoxy, isopropoxy, trifluoromethyl, trifluoromethoxy, and $CONH_2$;
each $R^3$ is independently selected from a 3 to 10 membered, monocyclic or bicyclic, heterocyclyl, heteroaryl, cycloalkyl or aryl ring; and
each heteroaryl or heterocyclyl ring of $R^1$, $R^2$, and $R^3$, comprises one to three heteroatoms independently selected from nitrogen, oxygen and sulfur.

In one particularly preferred aspect of the invention, where X represents $N(R^h)$, there is provided a compound of formula (IB):

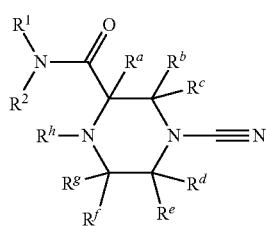

a tautomer thereof, or a pharmaceutically acceptable salt of said compound or tautomer, wherein:

$R^a$, $R^b$, $R^c$, $R^d$, $R^e$, $R^f$ and $R^g$, are each independently selected from hydrogen and methyl;

$R^1$ is selected from hydrogen and methyl;

$R^2$ is selected from a 5 to 10 membered, monocyclic or bicyclic, heteroaryl or aryl ring; or $R^1$ and $R^2$ together form a 5 to 10 membered, monocyclic or bicyclic, heteroaryl ring; each heteroaryl ring comprises one to three heteroatoms independently selected from nitrogen, oxygen and sulfur;

wherein $R^2$, or the ring formed by $R^1$ together with $R^2$, is optionally substituted with one to four, preferably one or two, groups independently selected from halo, cyano, methyl, ethyl, propyl, methoxy, ethoxy and propoxy.

In another particularly preferred aspect of the invention, where X represents $N(R^h)$, there is provided a compound of formula (IB):

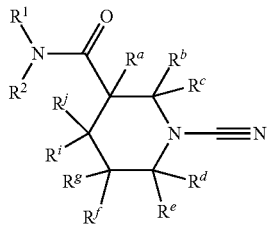

(IB)

a tautomer thereof, or a pharmaceutically acceptable salt of said compound or tautomer, wherein:

$R^a$, $R^b$, $R^c$, $R^d$, $R^e$, $R^f$ and $R^g$, are each independently selected from hydrogen and methyl;

$R^1$ is selected from hydrogen and methyl;

$R^2$ is selected from a 5 to 10 membered, monocyclic or bicyclic, heteroaryl or aryl ring, and a 3 to 10 membered, monocyclic or bicyclic, heterocyclyl or cycloalkyl ring; or $R^1$ and $R^2$ together form a 5 to 10 membered, monocyclic or bicyclic, heteroaryl ring; wherein $R^2$, or the ring formed by $R^1$ together with $R^2$, is substituted with one to four, preferably one or two, $R^3$ groups;

wherein $R^2$, or the ring formed by $R^1$ together with $R^2$, is optionally further substituted with one to four, preferably one or two groups, each independently selected from fluoro, chloro, cyano, methyl, methoxy, isopropoxy, trifluoromethyl, trifluoromethoxy, and $CONH_2$;

each $R^3$ is independently selected from a 3 to 10 membered, monocyclic or bicyclic, heterocyclyl, heteroaryl, cycloalkyl or aryl ring; and each heteroaryl or heterocyclyl ring of $R^1$, $R^2$, and $R^3$, comprises one to three heteroatoms independently selected from nitrogen, oxygen and sulfur.

In one particularly preferred aspect of the invention, where X represents $C(R^i)(R^j)$, there is provided a compound of formula (IC):

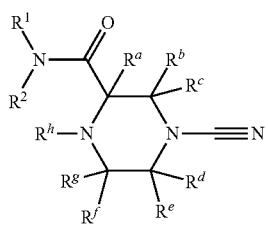

(IC)

a tautomer thereof, or a pharmaceutically acceptable salt of said compound or tautomer, wherein:

$R^a$ is selected from hydrogen, fluoro, and methyl;

$R^b$, $R^c$, $R^d$, and $R^e$, are each independently selected from hydrogen and methyl;

$R^f$, $R^g$, $R^i$, and $R^j$, are each independently selected from hydrogen, fluoro, and methyl;

$R^1$ is selected from hydrogen and methyl;

$R^2$ is selected from a 5 to 10 membered, monocyclic or bicyclic, heteroaryl or aryl ring; or $R^1$ and $R^2$ together form a 5 to 10 membered, monocyclic or bicyclic, heteroaryl ring;

each heteroaryl ring comprises one to three heteroatoms independently selected from nitrogen, oxygen and sulfur;

wherein $R^2$, or the ring formed by $R^1$ together with $R^2$, is optionally substituted with one to four, preferably one or two, groups independently selected from halo, cyano, methyl, ethyl, propyl, methoxy, ethoxy and propoxy.

In another particularly preferred aspect of the invention, where X represents $C(R^i)(R^j)$, there is provided a compound of formula (IC):

(IC)

a tautomer thereof, or a pharmaceutically acceptable salt of said compound or tautomer, wherein:

$R^a$ is selected from hydrogen, fluoro, and methyl;

$R^b$, $R^c$, $R^d$, and $R^e$, are each independently selected from hydrogen and methyl;

$R^f$, $R^g$, $R^i$, and $R^j$, are each independently selected from hydrogen, fluoro, and methyl;

$R^1$ is selected from hydrogen and methyl;

$R^2$ is selected from a 5 to 10 membered, monocyclic or bicyclic, heteroaryl or aryl ring, and a 3 to 10 membered, monocyclic or bicyclic, heterocyclyl or cycloalkyl ring; or $R^1$ and $R^2$ together form a 5 to 10 membered, monocyclic or bicyclic, heteroaryl ring;

wherein $R^2$, or the ring formed by $R^1$ together with $R^2$, is substituted with one to four, preferably one or two, $R^3$ groups;

wherein $R^2$, or the ring formed by $R^1$ together with $R^2$, is optionally further substituted with one to four, preferably one or two groups, each independently selected from fluoro, chloro, cyano, methyl, methoxy, isopropoxy, trifluoromethyl, trifluoromethoxy, and $CONH_2$;

each $R^3$ is independently selected from a 3 to 10 membered, monocyclic or bicyclic, heterocyclyl, heteroaryl, cycloalkyl or aryl ring; and each heteroaryl or heterocyclyl ring of $R^1$, $R^2$, and $R^3$, comprises one to three heteroatoms independently selected from nitrogen, oxygen and sulfur.

Preferred compounds of formula (I) for use in the present invention are selected from:

(R)-4-cyano-N-(4-phenylpyridin-2-yl)morpholine-2-carboxamide;
4-cyano-N-(5-(4-fluorophenyl)thiazol-2-yl)morpholine-2-carboxamide;
4-cyano-N-(3-propoxy-4-(1H-pyrazol-5-yl)phenyl)morpholine-2-carboxamide;
(R)-4-cyano-N-(6-(3-cyanophenyl)pyrimidin-4-yl)morpholine-2-carboxamide;
4-cyano-N-(4-(1-methyl-1H-pyrazol-4-yl)phenyl)morpholine-2-carboxamide;
(S)-2-(5-phenyl-2,3-dihydro-1H-pyrrolo[2,3-b]pyridine-1-carbonyl)morpholine-4-carbonitrile;
N-(6-(1H-pyrazol-4-yl)benzo[d]thiazol-2-yl)-4-cyanomorpholine-2-carboxamide;
4-cyano-N-(1-phenyl-1H-imidazol-4-yl)morpholine-2-carboxamide;
N-([1,1'-biphenyl]-4-yl)-4-cyanomorpholine-2-carboxamide;
4-cyano-N-(3-(3-methoxyphenyl)isoxazol-5-yl)morpholine-2-carboxamide;
4-cyano-N-(5-phenyl-1H-pyrazol-3-yl)morpholine-2-carboxamide;
4-cyano-N-(5-phenylpyridin-2-yl)morpholine-2-carboxamide;
4-cyano-N-(5-phenylisoxazol-3-yl)morpholine-2-carboxamide;
4-cyano-N-(4-cyano-[2,4'-bipyridin]-2'-yl)morpholine-2-carboxamide;
N-([1,1'-biphenyl]-3-yl)-4-cyanomorpholine-2-carboxamide;
4-cyano-N-(3-(1-methyl-1H-pyrazol-4-yl)phenyl)morpholine-2-carboxamide;
4-cyano-N-(6-phenylpyridin-3-yl)morpholine-2-carboxamide;
4-cyano-N-(2'-cyano-[4,4'-bipyridin]-2-yl)morpholine-2-carboxamide;
4-cyano-N-(3-(3-(trifluoromethyl)phenyl)isoxazol-5-yl)morpholine-2-carboxamide;
(R)-4-cyano-N-(5-phenylthiazol-2-yl)morpholine-2-carboxamide;
(R)—N-(6-(3-chlorophenyl)pyrimidin-4-yl)-4-cyanomorpholine-2-carboxamide;
(R)-4-cyano-N-(6-(3-methoxyphenyl)pyrimidin-4-yl)morpholine-2-carboxamide;
(R)-4-cyano-N-(6-(3-isopropoxyphenyl)pyrimidin-4-yl)morpholine-2-carboxamide;
(R)-4-cyano-N-(6-(3-cyano-5-fluorophenyl)pyrimidin-4-yl)morpholine-2-carboxamide;
(R)-4-cyano-N-(6-(4-cyanophenyl)pyrimidin-4-yl)morpholine-2-carboxamide;
(R)—N-(6-(4-chlorophenyl)pyrimidin-4-yl)-4-cyanomorpholine-2-carboxamide;
(R)—N-(6-(3-carbamoylphenyl)pyrimidin-4-yl)-4-cyanomorpholine-2-carboxamide;
(R)-4-cyano-N-(2-phenylthiazol-5-yl)morpholine-2-carboxamide;
(R)—N-(5-(1H-pyrazol-5-yl)pyridin-2-yl)-4-cyanomorpholine-2-carboxamide;
(R)—N-(6-(1H-indazol-4-yl)pyrimidin-4-yl)-4-cyanomorpholine-2-carboxamide;
(R)—N-(6-(1H-pyrazol-4-yl)isoquinolin-3-yl)-4-cyanomorpholine-2-carboxamide;
(R)-4-cyano-N-(5-phenyl-1,3,4-thiadiazol-2-yl)morpholine-2-carboxamide;
(S)-4-cyano-N-(5-phenylthiazol-2-yl)morpholine-2-carboxamide;
(S)-4-cyano-N-(isoquinolin-3-yl)morpholine-2-carboxamide;
(S)-4-cyano-N-(4-phenylpyridin-2-yl)morpholine-2-carboxamide;
1-cyano-N-(3-propoxy-4-(1H-pyrazol-5-yl)phenyl)piperidine-3-carboxamide;
1-cyano-N-(1-phenyl-1H-imidazol-4-yl)piperidine-3-carboxamide;
1-cyano-N-(5-phenyl-1H-pyrazol-3-yl)piperidine-3-carboxamide;
1-cyano-N-(5-phenylpyridin-2-yl)piperidine-3-carboxamide;
1-cyano-N-(4-phenylpyridin-2-yl)piperidine-3-carboxamide;
1-cyano-N-(3-phenylisoxazol-5-yl)piperidine-3-carboxamide;
1-cyano-3-fluoro-N-(5-phenylthiazol-2-yl)piperidine-3-carboxamide;
1-cyano-3-fluoro-N-(1-phenyl-1H-imidazol-4-yl)piperidine-3-carboxamide;
1-cyano-3-fluoro-N-(4-phenylpyridin-2-yl)piperidine-3-carboxamide;
1-cyano-3-fluoro-N-(5-phenylisoxazol-3-yl)piperidine-3-carboxamide;
1-cyano-N-(6-(3-cyanophenyl)pyrimidin-4-yl)-3-fluoropiperidine-3-carboxamide;
1-cyano-N-(4-(3-cyanophenyl)pyridin-2-yl)-3-fluoropiperidine-3-carboxamide;
1-cyano-3-fluoro-N-(5-phenyl-1,3,4-thiadiazol-2-yl)piperidine-3-carboxamide;
N-(5-(1H-pyrazol-5-yl)pyridin-2-yl)-1-cyano-3-fluoropiperidine-3-carboxamide;
N-(6-(1H-pyrazol-4-yl)benzo[d]thiazol-2-yl)-1-cyano-3-fluoropiperidine-3-carboxamide;
(R)-4-cyano-N-(3-(3-(trifluoromethyl)phenyl)isoxazol-5-yl)morpholine-2-carboxamide;
1-cyano-N-(4-(3-cyanophenyl)pyridin-2-yl)-3-fluoropiperidine-3-carboxamide;
(R)-4-cyano-N-(4-(3-cyanophenyl)pyridin-2-yl)morpholine-2-carboxamide;
(S)-4-cyano-N-(4-(3-cyanophenyl)pyridin-2-yl)morpholine-2-carboxamide;
(R)-1-cyano-N-(5-phenylthiazol-2-yl)piperidine-3-carboxamide;
(S)-1-cyano-N-(5-phenylthiazol-2-yl)piperidine-3-carboxamide;
(S)-1-cyano-N-(4-(3-cyanophenyl)pyridin-2-yl)piperidine-3-carboxamide;
1-cyano-5,5-difluoro-N-(1-phenyl-1H-imidazol-4-yl)piperidine-3-carboxamide;
N-(6-(1H-pyrazol-4-yl)benzo[d]thiazol-2-yl)-1-cyano-5,5-difluoropiperidine-3-carboxamide;
(2R,5*)-4-cyano-N-(6-(3-cyanophenyl)pyrimidin-4-yl)-5-methylmorpholine-2-carboxamide;
(R)—N-(6-(3-(1H-pyrazol-4-yl)phenyl)pyrimidin-4-yl)-4-cyanomorpholine-2-carboxamide;

(R)—N-(5-(3-chlorophenyl)pyridazin-3-yl)-4-cyanomorpholine-2-carboxamide;
(R)-4-cyano-N-(5-(3-cyanophenyl)pyridazin-3-yl)morpholine-2-carboxamide;
1-cyano-N-(5-(3-cyanophenyl)isoxazol-3-yl)-3-fluoropiperidine-3-carboxamide;
(R)-4-cyano-N-(6-cyanoisoquinolin-3-yl)morpholine-2-carboxamide;
(2R)-4-cyano-N-(1-(4-cyanopyridin-2-yl)pyrrolidin-3-yl) morpholine-2-carboxamide;
(S)-4-cyano-1-methyl-N-(5-phenylthiazol-2-yl)piperazine-2-carboxamide;
(R)-4-cyano-1-methyl-N-(5-phenylthiazol-2-yl)piperazine-2-carboxamide;
4-cyano-1-phenyl-N-(5-phenylthiazol-2-yl)piperazine-2-carboxamide;
1-acetyl-4-cyano-N-(5-phenylthiazol-2-yl)piperazine-2-carboxamide; and
4-cyano-1-(methylsulfonyl)-N-(5-phenylthiazol-2-yl)piperazine-2-carboxamide;
(R)—N-(5-(1H-pyrazol-5-yl)pyridin-2-yl)-1-cyano-3-fluoropiperidine-3-carboxamide;
1-cyano-N-(3-(3-cyanophenyl)isoxazol-5-yl)-3-fluoropiperidine-3-carboxamide;
(R)—N-(5-(3-chlorophenyl)isoxazol-3-yl)-1-cyano-3-fluoropiperidine-3-carboxamide;
(R)-1-cyano-3-fluoro-N-(5-(3-(trifluoromethyl)phenyl)isoxazol-3-yl)piperidine-3-carboxamide;
(R)—N-(3-(3-chlorophenyl)isoxazol-5-yl)-1-cyano-3-fluoropiperidine-3-carboxamide;
(R)—N-(5-(1H-pyrazol-1-yl)pyridin-2-yl)-1-cyano-3-fluoropiperidine-3-carboxamide;
(R)-1-cyano-N-(4-(3-cyanophenyl)oxazol-2-yl)-3-fluoropiperidine-3-carboxamide;
(R)-1-cyano-N-(1-(3-cyanophenyl)-1H-imidazol-4-yl)-3-fluoropiperidine-3-carboxamide;
1-cyano-3-fluoro-N-(1-(3-(trifluoromethyl)phenyl)-1H-imidazol-4-yl)piperidine-3-carboxamide;
1-cyano-3-fluoro-N-(1-(3-(trifluoromethoxy)phenyl)-1H-imidazol-4-yl)piperidine-3-carboxamide;
(R)-1-cyano-N-(1-(3-cyanophenyl)-1H-1,2,3-triazol-4-yl)-3-fluoropiperidine-3-carboxamide;
(R)-1-cyano-N-(1-(3-cyanophenyl)-1H-1,2,4-triazol-3-yl)-3-fluoropiperidine-3-carboxamide;
(R)—N-(5-(1H-indazol-7-yl)pyridin-2-yl)-1-cyano-3-fluoropiperidine-3-carboxamide;
(R)—N-(5-(1H-indazol-4-yl)pyridin-2-yl)-1-cyano-3-fluoropiperidine-3-carboxamide;
(R)—N-(5-(1H-indazol-7-yl)pyrazin-2-yl)-1-cyano-3-fluoropiperidine-3-carboxamide;
(R)—N-(5-(1H-indazol-4-yl)pyrazin-2-yl)-1-cyano-3-fluoropiperidine-3-carboxamide;
(R)—N-(6-(1H-indazol-7-yl)pyridazin-3-yl)-1-cyano-3-fluoropiperidine-3-carboxamide;
(R)—N-(5-(1H-pyrazolo[3,4-c]pyridin-7-yl)pyridin-2-yl)-1-cyano-3-fluoropiperidine-3-carboxamide;
(R)—N-(5-(1H-pyrazolo[4,3-b]pyridin-7-yl)pyridin-2-yl)-1-cyano-3-fluoropiperidine-3-carboxamide;
(R)—N-(6-(1H-indazol-4-yl)pyridazin-3-yl)-1-cyano-3-fluoropiperidine-3-carboxamide;
(R)—N-(5-(1H-indazol-7-yl)pyrimidin-2-yl)-1-cyano-3-fluoropiperidine-3-carboxamide;
a tautomer thereof, or a pharmaceutically acceptable salt of said compound or tautomer.

It should be noted that each of the chemical compounds listed above represents a particular and independent aspect of the invention.

Pharmaceutical acceptable salts of the compounds of formula (I) include the acid addition and base salts (including di-salts) thereof.

Suitable acid addition salts are formed from acids which form non-toxic salts.

Examples include the acetate, aspartate, benzoate, besylate, bicarbonate/carbonate, bisulfate, camsylate, citrate, edisylate, esylate, fumarate, gluceptate, gluconate, glucuronate, hibenzate, hydrochloride/chloride, hydrobromide/bromide, hydroiodide/iodide, hydrogen phosphate, isethionate, D- and L-lactate, malate, maleate, malonate, mesylate, methylsulfate, 2-napsylate, nicotinate, nitrate, orotate, palmate, phosphate, saccharate, stearate, succinate sulfate, D- and L-tartrate, and tosylate salts.

Suitable base salts are formed from bases which form non-toxic salts. Examples include the aluminium, ammonium, arginine, benzathine, calcium, choline, diethylamine, triethylamine, diolamine, glycine, lysine, magnesium, meglumine, olamine, potassium, sodium, tromethamine and zinc salts.

Suitable salts also include salts of amino acids, such as glycine, alanine, valine, leucine, isoleucine, cysteine, methionine and proline. Further pharmaceutically acceptable salts include quaternary ammonium salts of the compounds of the invention.

For a review on suitable salts, see Stahl and Wermuth, Handbook of Pharmaceutical Salts: Properties, Selection, and Use, Wiley-VCH, Weinheim, Germany (2002).

A pharmaceutical acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. Salts may also be prepared by exchanging a counter-ion of a compound in the form of a salt with another counter-ion, for example using a suitable ion exchange resin.

Pharmaceutical acceptable solvates in accordance with the invention include hydrates and solvates wherein the solvent of crystallization may be isotopically substituted, e. g. $D_2O$, acetone-$d_6$, DMSO-$d_6$.

Also within the scope of the invention are clathrates, drug-host inclusion complexes wherein, in contrast to the aforementioned solvates, the drug and host are present in non-stoichiometric amounts. For a review of such complexes, see J. Pharm Sci, 64 (8), 1269-1288 by Haleblian (August 1975).

Hereinafter all references to compounds of formula (I) include references to salts thereof and to solvates and clathrates of compounds of formula (I) and salts thereof.

The invention includes all polymorphs of the compounds of formula (I) as hereinbefore defined.

Also within the scope of the invention are so-called "prodrugs" of the compounds of formula (I). Thus, certain derivatives of compounds of formula (I) which have little or no pharmacological activity themselves can, when metabolised upon administration into or onto the body, give rise to compounds of formula (I) having the desired activity. Such derivatives are referred to as "prodrugs".

Prodrugs in accordance with the invention can, for example, be produced by replacing appropriate functionalities present in the compounds of formula (I) with certain moieties known to those skilled in the art as "pro-moieties" as described, for example, in "Design of Prodrugs" by H Bundgaard (Elsevier, 1985). Finally, certain compounds of formula (I) may themselves act as prodrugs of other compounds of formula (I).

Certain derivatives of compounds of formula (I) which contain a nitrogen atom may also form the corresponding N-oxide, and such compounds are also within the scope of the present invention.

Compounds of formula (I) containing one or more asymmetric carbon atoms can exist as two or more optical isomers. Where a compound of formula (I) contains an alkenyl or alkenylene group, geometric cis/trans (or Z/E) isomers are possible, and where the compound contains, for example, a keto or oxime group, tautomeric isomerism ('tautomerism') may occur. It follows that a single compound may exhibit more than one type of isomerism.

Included within the scope of the present invention are all optical isomers, geometric isomers and tautomeric forms of the compounds of formula, including compounds exhibiting more than one type of isomerism, and mixtures of one or more thereof. Cis/trans isomers may be separated by conventional techniques well known to those skilled in the art, for example, fractional crystallisation and chromatography.

Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. The present invention includes all crystal forms of the compounds of formula (I) including racemates and racemic mixtures (conglomerates) thereof. Stereoisomeric conglomerates may be separated by conventional techniques known to those skilled in the art—see, for example, "Stereochemistry of Organic Compounds" by E. L. Eliel and S. H. Wilen (Wiley, New York, 1994).

In particular, the compounds of formula (I) contain a chiral centre at the carbon atom of the ring that is substituted by $R^a$, and said stereocentre can thus exist in either the (R) or (S) configuration. The designation of the absolute configuration (R) and (S) for stereoisomers in accordance with IUPAC nomenclature is dependent on the nature of the substituents and application of the sequence-rule procedure. The compounds of formula (I) may thus exist in either of the following enantiomeric configurations:

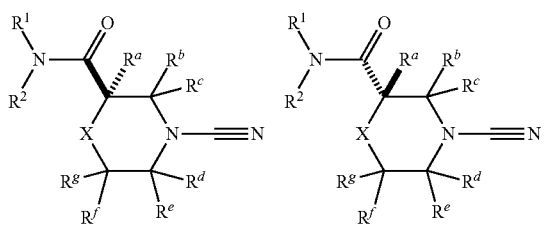

In a preferred aspect, the compounds of formula (I) possess the absolute stereochemical configuration:

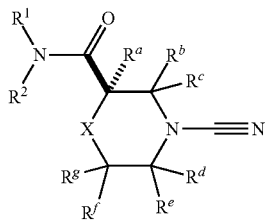

In another preferred aspect, the compounds of formula (I) possess the absolute stereochemical configuration:

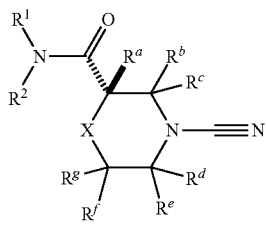

Included within the scope of the present invention are each of these (R) and (S) stereoisomers of the compounds of formula (I) in individual form, or mixtures thereof. When the compound of formula (I) is isolated as a single stereoisomer, the compound may exist with an enantiomeric excess of at least 80%, preferably at least 90%, more preferably at least 95%, for example 96%, 96%, 98%, 99%, or 100%.

The present invention also includes all pharmaceutically acceptable isotopic variations of a compound of formula (I). An isotopic variation is defined as one in which at least one atom is replaced by an atom having the same atomic number, but an atomic mass different from the atomic mass usually found in nature.

Examples of isotopes suitable for inclusion in the compounds of the invention include isotopes of hydrogen, such as $^2H$ and $^3H$, carbon, such as $^{13}C$ and $^{14}C$, nitrogen, such as $^{15}N$, oxygen, such as $^{17}O$ and $^{18}O$, phosphorus, such as $^{32}P$, sulfur, such as $^{35}S$, fluorine, such as $^{18}F$, and chlorine, such as $^{38}Cl$.

The isotopes may be radioactive or non-radioactive. In one embodiment, the compounds contain no radioactive isotopes. Such compounds are preferred for therapeutic use. In another embodiment, however, the compounds may contain one or more radioisotopes. Compounds containing such radioisotopes may be useful in a diagnostic context.

Certain isotopically labelled compounds of formula (I), for example, those incorporating a radioactive isotope, are useful in drug and/or substrate tissue distribution studies. The radioactive isotopes i.e. $^3H$ and $^{14}C$ are particularly useful for this purpose in view of their ease of incorporation and ready means of detectifon. Substitution with heavier isotopes i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, a can be useful in Positron Emission Topography (PET) studies for examining receptor occupancy. Isotopically labelled compounds of formula (I) can generally be prepared by conventional techniques known to those skilled in the art or by processes analogous to those described in the accompanying examples and preparations using an appropriate isotopically labelled reagent in place of the non-labelled reagent previously employed.

The compounds of formula (I) may exist in crystalline or amorphous form and some of the crystalline forms may exist as polymorphs, which are included within the scope of the present invention. Polymorphic forms of compounds of formula (I) may be characterised and differentiated using a number of conventional analytical techniques, including, but not limited to, infra-red spectra, Raman spectra, X-ray powder diffraction, differential scanning calorimetry, thermogravimetric analysis and solid state nuclear magnetic resonance.

Accordingly, in further embodiments, the invention provides a compound according to any described embodiments in a crystalline form. The compound may be from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline. The compound may alternatively be in an amorphous form.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

The invention relates to any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Compounds of the invention may be metabolised in vivo. Metabolites of compounds of formula (I) are also within the scope of the present invention. The term 'metabolites' refers to all molecules derived from any of the compounds according to the present invention in a cell or organism, preferably mammal. Preferably the term relates to molecules which differ from any molecule which is present in any such cell or organism under physiological conditions.

A treatment defined herein may be applied as a sole therapy of may involve, in addition to the compounds of the invention, conventional surgery or radiotherapy or chemotherapy. Furthermore, compounds of formula (I) can also be used in combination with existing therapeutic agents for the treatment of conditions associated with cancer, including small molecule therapeutics or antibody based therapeutics.

According to a further aspect, the present invention provides a pharmaceutical composition comprising a compound of formula (I) as defined herein, or a pharmaceutically acceptable salt of said compound or tautomer, together with a pharmaceutically acceptable diluent or carrier.

Pharmaceutical compositions of the invention comprise any of the compounds of the invention combined with any pharmaceutically acceptable carrier, adjuvant or vehicle. Examples of pharmaceutically acceptable carriers are known to those skilled in the art and include, but are not limited to, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compounds of formula (I) are inhibitors of the deubiquitylating enzyme USP30.

According to a further aspect, the present invention provides a compound of formula (I) as defined herein, a tautomer thereof, or a pharmaceutically acceptable salt of said compound or tautomer for use as a medicament.

According to a further aspect, the present invention provides a method of treatment of a disorder or condition where inhibition of USP30 is known, or can be shown, to produce a beneficial effect, in a mammal, comprising administering to said mammal a therapeutically effective amount of a compound of formula (I) as defined herein, a tautomer thereof, or a pharmaceutically acceptable salt of said compound or tautomer.

According to a further aspect, the present invention provides the use of a compound of formula (I) as defined herein, a tautomer thereof, or a pharmaceutically acceptable salt of said compound or tautomer, in the preparation of a medicament for the treatment of a disorder or condition where inhibition of USP30 is known, or can be shown, to produce a beneficial effect.

The term "treat" or "treating" or "treatment" includes prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

The dose of the compound is that amount effective to prevent occurrence of the symptoms of the disorder or to treat some symptoms of the disorder from which the patient suffers. By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reoccurrence of the symptoms of the disorder.

The disorder or condition benefiting from USP30 activity is selected from a condition involving mitochondrial dysfunction, and cancer.

In one preferred embodiment of all aspects of the invention, the disorder or condition benefiting from USP30 activity is a condition involving mitochondrial dysfunction.

Mitochondrial dysfunctions result from defects of the mitochondria, which are specialized compartments present in every cell of the body except red blood cells. When mitochondria fail, less and less energy is generated within the cell and cell injury or even cell death will follow. If this process is repeated throughout the body the life of the subject in whom this is happening is severely compromised. Diseases of the mitochondria appear most often in organs that are very energy demanding such as the brain, heart, liver, skeletal muscles, kidney and the endocrine and respiratory system.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS); mitochondrial myopathy; encephalopathy; lactic acidosis; stroke-like episodes (MELAS) syndrome; Leber's hereditary optic neuropathy (LHON); cancer (including, for example, breast, ovarian, prostate, lung, kidney, gastric, colon, testicular, head and neck, pancreas, brain, melanoma, bone or other cancers of tissue organs and cancers of the blood cells, such as lymphoma and leukaemia, multiple myeloma, colorectal cancer, and non-small cell lung carcinoma); neuropathy, ataxia, retinitis pigmentosa, maternally inherited Leigh syndrome (NARP-MILS); Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GMI-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; very long-chain acyl-CoA dehydrogenase (VL-CAD) deficiency; and age-dependent decline in cognitive function and muscle strength.

The condition involving mitochondrial dysfunction may be a CNS disorder, for example a neurodegenerative disease.

Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotemporal dementia.

In particular, the compounds of the invention may be useful in the treatment of Parkinson's disease, including, but not limited to, PD related to mutations in α-synuclein, parkin and PINK1, autosomal recessive juvenile Parkinson's disease (AR-JP) where parkin is mutated.

The compounds of the invention or pharmaceutical compositions thereof as described herein may be combined with one or more additional agents when used for the treatment of conditions involving mitochondrial dysfunction. The compounds may be combined with one or more additional agents selected from levodopa, a dopamine agonist, a monoamino oxygenase (MAO) B inhibitor, a catechol O-methyltransferase (COMT) inhibitor, an anticholinergic, riluzole, amantadine, a cholinesterase inhibitor, memantine, tetrabenazine, an antipsychotic, diazepam, clonazepam, an antidepressant, and an anti-convulsant.

In another preferred embodiment of all aspects of the invention, the disorder or condition benefiting from USP30 activity is cancer. The cancer may be linked to mitochondrial dysfunction. Preferred cancers include, for example, breast, ovarian, prostate, lung, kidney, gastric, colon, testicular, head and neck, pancreas, brain, melanoma, bone or other cancers of tissue organs and cancers of the blood cells, such as lymphoma and leukaemia, multiple myeloma, colorectal cancer, and non-small cell lung carcinoma.

In particular, the compounds of the invention may be useful in the treatment of cancer where apoptotic pathways are dysregulated and more particularly where proteins of the BCL-2 family are mutated, or over or under expressed.

References to 'treatment' includes curative, palliative and prophylactic, and includes means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and other mammals.

The compounds of the invention or pharmaceutical compositions thereof, as described herein, may be used alone or combined with one or more additional pharmaceutical agents. The compounds may be combined with an additional anti-tumour therapeutic agent, for example, chemotherapeutic drugs or inhibitors of other regulatory proteins. In one embodiment, the additional anti-tumour therapeutic agent is a BH-3 mimetic. In a further embodiment BH-3 mimetics may be selected from but not limited to one or more of ABT-737, ABT-199, ABT-263, and Obatoclax. In a further embodiment, the additional anti-tumour agent is a chemotherapeutic agent. Chemotherapeutic agents may be selected from but not limited to, olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin.

The pharmaceutical compositions of the invention may be administered in any suitably effective manner, such as oral, parenteral, topical, inhaled, intranasal, rectal, intravaginal, ocular, and andial. Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

A typical tablet may be prepared using standard processes known to a formulation chemist, for example, by direct compression, granulation (dry, wet, or melt), melt congealing, or extrusion. The tablet formulation may comprise one or more layers and may be coated or uncoated.

Examples of excipients suitable for oral administration include carriers, for example, cellulose, calcium carbonate, dibasic calcium phosphate, mannitol and sodium citrate, granulation binders, for example, polyvinylpyrrolidine, hydroxypropylcellulose, hydroxypropylmethylcellulose and gelatin, disintegrants, for example, sodium starch glycolat and silicates, lubricating agents, for example, magnesium stearate and stearic acid, wetting agents, for example, sodium lauryl sulphate, preservatives, anti-oxidants, flavours and colourants.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are to be found in Verma et al, Pharmaceutical Technology On-line, 25 (2), 1-14 (2001). Other modified release formulations are described in U.S. Pat. No. 6,106,864.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by suitable processing, for example, the use of high energy spray-dried dispersions (see WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled dual-, targeted and programmed release.

Pharmaceutical compositions of the present invention also include compositions and methods known in the art for bypassing the blood brain barrier or can be injected directly into the brain. Suitable areas for injection include the cerebral cortex, cerebellum, midbrain, brainstem, hypothalamus, spinal cord and ventricular tissue, and areas of the PNS including the carotid body and the adrenal medulla.

Dosage

The magnitude of an effective dose of a compound will, of course, vary with the nature of the severity of the condition to be treated and the route of administration. The selection of appropriate dosages is within the remit of the physician. The daily dose range is about 10 µg to about 100 mg per kg body weight of a human and non-human animal and in general may be around 10 µg to 30 mg per kg body weight per dose. The above dose may be given from one to three times per day.

For example, oral administration may require a total daily dose of from 5 mg to 1000 mg, such as from 5 to 500 mg, while an intravenous dose may only require from 0.01 to 30 mg/kg body weight, such as from 0.1 to 10 mg/kg, more preferably from 0.1 to 1 mg/kg body weight. The total daily dose may be administered in single or divided doses.

The skilled person will also appreciate that, in the treatment of certain conditions, compounds of the invention may be taken as a single dose on an "as required" basis (i.e. as needed or desired).

Synthetic Methodologies

Compounds of formula (I) may be prepared using methods as described below in the general reaction schemes and the representative examples. Where appropriate, the individual transformations within a scheme may be completed in a different order.

According to a further aspect, the present invention provides a process for the preparation of a compound of formula (I), as defined herein, comprising reacting a compound of formula (IV), wherein $R^a$, $R^b$, $R^c$, $R^d$, $R^e$, $R^f$, $R^g$, and X are as defined herein, and PG is a protecting group, such as BOC or CBZ, with an amine of formula $NHR^1R^2$, wherein $R^1$ and $R^2$ are as defined herein, to give an amide of formula (III) (Scheme 1). The amide-coupling reaction can be performed using standard methodology, for example by reaction using a coupling reagent such as DCC, HATU, HBTU, EDC or via a mixed anhydride. Alternatively, the acid (II) can be converted into the acid chloride using $SOCl_2$, $PCl_3$, or $PCl_5$, which can then be reacted with the amine of formula $NHR^1R^2$, preferably in a suitable solvent in the presence of a suitable base.

Additionally, one compound of formula (III) may be converted into another compound of formula (III), for example via a Suzuki coupling of a bromo-aryl or bromo-heteroaryl group. The compound of formula (III) may be deprotected using standard methods to give amine (II), which may then be reacted with cyanogen bromide to give the compound of formula (I).

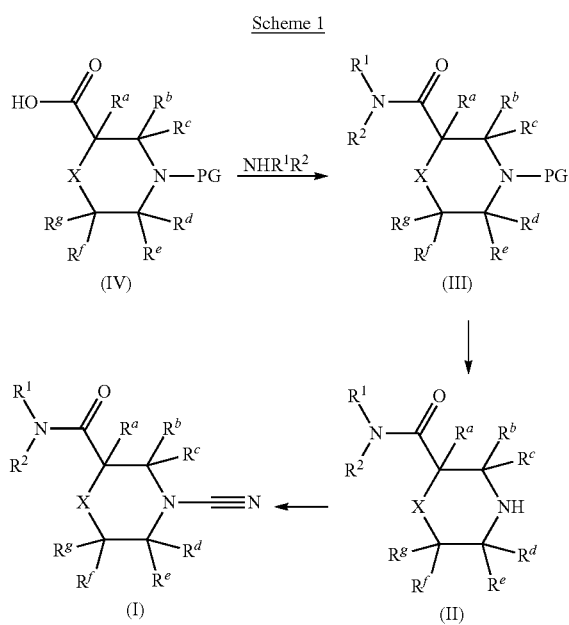

Scheme 1

In a further aspect, the present invention provides a compound, which is selected from formulae (II) and (III):

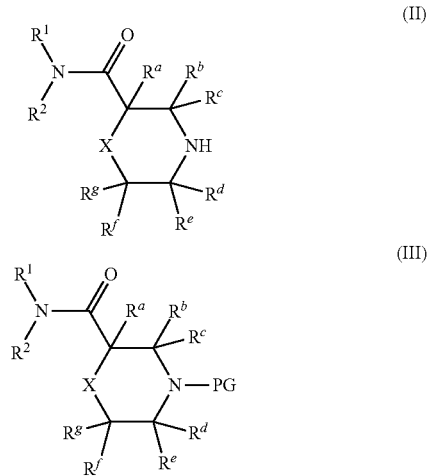

wherein PG is a protecting group, preferably BOC or CBZ, and $R^a$, $R^b$, $R^c$, $R^d$, $R^e$, $R^f$, $R^g$, X, $R^1$ and $R^2$ are as defined herein, a tautomer thereof, or a salt of said compound or tautomer.

In further preferred aspects, the present invention provides a compound, which is selected from formulae (II) and (III), as described herein, in the absolute stereochemical configuration corresponding to the compounds of formula (I), and preferred embodiments thereof.

Additional representative compounds and stereoisomers, racemic mixtures, diastereomers and enantiomers thereof may be prepared using the intermediates prepared in accordance to the general schemes and other materials, compounds and reagents known to those skilled in the art. Enantiomers may be separated using standard techniques, such as Chiral HPLC, for example, using column CHIRAL-ART SA 250×4.6 mm 5 μm.

The invention is illustrated by the following non-limiting examples in which the following abbreviations and definitions are used.

All the compounds were characterised by liquid chromatography-mass spectroscopy (LCMS) or $^1H$ NMR or both.

Synthetic Schemes

Abbreviations:

BOC Tert-butyloxycarbonyl
d Doublet (NMR signal)
dba Dibenzylideneacetone
DCM Dichloromethane
DEA Diethylamine
DIPEA Diisopropylethylamine
DMA Dimethylacetamide
DMF N,N-Dimethylformamide
DMSO Dimethylsulphoxide
dppf 1,1'-Bis(diphenylphosphino)ferrocene
ES Electrospray
EtOAc Ethyl acetate
EtOH Ethanol
h Hour(s)
HATU 1-[Bis(dimethylamino)methylene]-1H-1,2,3-triazolo[4,5-b]pyridinium 3-oxid hexafluorophosphate
HPLC High Performance Liquid Chromatography
IPA Isopropyl alcohol
m Multiplet (NMR signal)
MeCN Acetonitrile
MeOH Methanol
min Minute(s)
MTBE Methyl tert-butyl ether
NMP N-Methylpyrrolidine
rt Room temperature
RT Retention Time
s Singlet (NMR signal)
SFC Supercritical Fluid Chromatography
t Triplet (NMR signal)
T3P 2,4,6-Tripropyl-1,3,5,2,4,6-trioxatriphosphorinane-2,4,6-trioxide
TBTU N,N,N',N'-Tetramethyl-O-(benzotriazol-1-yl)uronium tetrafluoroborate
TEA Triethylamine
TEMPO 2,2,6,6-Tetramethylpiperidine-1-oxyl radical
TFA Trifluoroacetic acid
THF Tetrahydrofuran Analytical Methods:

Method A

| | | |
|---|---|---|
| Column | X-bridge C18, 50 × 4.6 mm, 3.5 μm or equivalent | |
| Mobile Phase | (A) 0.1% Ammonia in water | |
| | (B) 0.1% Ammonia in MeCN | |
| Flow Rate | 1.0 ml/min | |

| | Time | % B |
|---|---|---|
| Gradient | 0.01 | 5 |
| | 5.00 | 90 |
| | 5.80 | 95 |
| | 7.20 | 95 |

Method B

| | | |
|---|---|---|
| Column | BEH C18, 50 × 2.1 mm, 1.7 μm or equivalent | |
| Mobile Phase | (A) 5 mM Ammonium acetate + 0.1% formic acid in water | |
| | (B) 0.1% Formic acid in MeCN | |
| Flow Rate | 0.45 ml/min | |

| | Time | % B |
|---|---|---|
| Gradient | 0.01 | 2 |
| | 0.50 | 2 |
| | 5.00 | 90 |
| | 6.00 | 95 |
| | 7.00 | 95 |

Method C

| | | |
|---|---|---|
| Column | BEH C18, 50 × 2.1 mm, 1.7 μm or equivalent | |
| Mobile Phase | (A) 5 mM Ammonium acetate + 0.1% formic acid in water | |
| | (B) 0.1% Formic acid in MeCN | |
| Flow Rate | 0.55 ml/min | |

| | Time | % B |
|---|---|---|
| Gradient | 0.01 | 5 |
| | 0.40 | 5 |
| | 0.80 | 35 |
| | 1.20 | 55 |
| | 2.50 | 100 |
| | 3.30 | 100 |

Method D

| | | |
|---|---|---|
| Column | X-bridge C18, 250 × 4.6 mm, 5 μm or equivalent | |
| Mobile Phase | (A) 0.1% Ammonia in water | |
| | (B) 0.1% Ammonia in MeCN | |
| Flow Rate | 1.0 ml/min | |

| | Time | % B |
|---|---|---|
| Gradient | 0.01 | 5 |
| | 5.00 | 5 |
| | 10.00 | 30 |
| | 15.00 | 30 |
| | 25.00 | 60 |
| | 30.00 | 90 |
| | 35.00 | 90 |

Method E

| | | |
|---|---|---|
| Column | X-bridge C18, 250 × 4.6 mm, 5 μm or equivalent | |
| Mobile Phase | (A) 0.1% Formic acid in water | |
| | (B) MeCN | |
| Flow Rate | 1.0 ml/min | |

| | Time | % B |
|---|---|---|
| Gradient | 0.01 | 0 |
| | 25.00 | 40 |
| | 28.00 | 100 |
| | 30.00 | 100 |

Method F

| | | |
|---|---|---|
| Column | Zorbax RRHD, 50 × 2.1 mm, 1.8 μm or equivalent | |
| Mobile Phase | (A) 0.1% Formic acid in water | |
| | (B) 0.1% Formic acid in MeCN | |
| Flow Rate | 0.4 ml/min | |

| | Time | % B |
|---|---|---|
| Gradient | 0.01 | 0 |
| | 4.00 | 0 |
| | 8.00 | 7 |
| | 18.00 | 7 |
| | 22.00 | 10 |
| | 23.00 | 90 |
| | 24.00 | 90 |

Analytical chiral SFC methods were run on a Waters SFC investigator and PDA detector.

Chiral SFC Method X

| | | |
|---|---|---|
| Column | Chiralpak AD-H, 250 × 4.6 mm, 5 μm | |
| Mobile Phase | (A) Liquid carbon dioxide; (B) IPA | |
| Flow Rate | 4.00 ml/min | |

| | Time | % B |
|---|---|---|
| Gradient | 0.01 | 40 |
| | 8.00 | 40 |

Chiral SFC Method Y

| | | |
|---|---|---|
| Column | Chiralcel OJ-H, 250 × 4.6 mm, 5 μm | |
| Mobile Phase | (A) Liquid carbon dioxide; (B) IPA | |
| Flow Rate | 3.00 ml/min | |

| | Time | % B |
|---|---|---|
| Gradient | 0.01 | 10 |
| | 15.00 | 10 |

| Chiral SFC Method Z | |
|---|---|
| Column | Chiralpak AD-H, 250 × 4.6 mm, 5 μm |
| Mobile Phase | (A) Liquid carbon dioxide; (B) IPA:MeCN (50:50) |
| Flow Rate | 3.00 ml/min |
| | Time | % B |
| Gradient | 0.01 | 20 |
| | 10.00 | 20 |

General method A

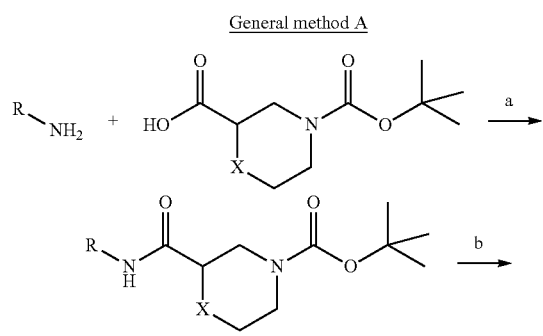

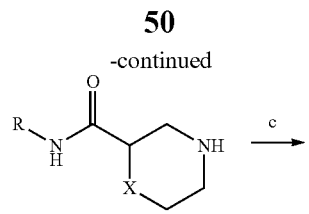

In a typical synthetic procedure, an amine is reacted with a BOC protected cyclic amine substituted with a carboxylic acid to form an amide. Amide coupling reagents can be used such as HATU, TBTU, T3P, or the acid can be converted to the corresponding acyl chloride using reagents such as POCl3 and subsequent reaction with an amine. In a second step the BOC protecting group is removed, typically by treatment with a strong acid such as HCl or TFA. In a final step, the amine is reacted with cyanogen bromide under basic conditions to provide the desired product.

General method B

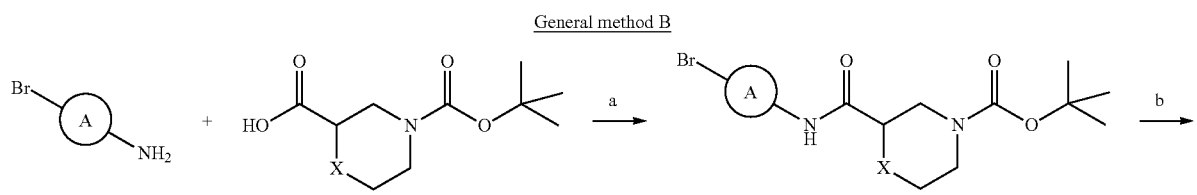

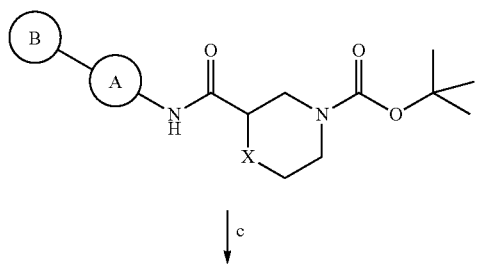

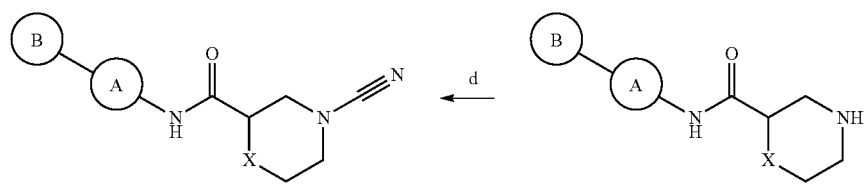

In a further typical synthetic procedure, an amine is attached to an aromatic ring substituted with a halogen, typically Cl, Br or I. Following the amide coupling reaction, a metal catalysed C—C bond forming reaction is conducted, typically a Sukuki reaction, to introduce a second aromatic ring. The final two steps are conducted as described in General method A.

base such as lithium diisopropylamide (LDA) or lithium bis(trimethylsilyl)amide (LiHMDS), followed by reaction with an electrophilic fluorine reagent such as N-fluoro-o-benzenedisulfonimide (NFOBS), N-fluorobenzenesulfonimide (NFSI) or Selectfluor. In a second step, the ester can be hydrolysed by treatment with LiOH or NaOH in the presence of water in a solvent such as THF or MeOH.

General method C

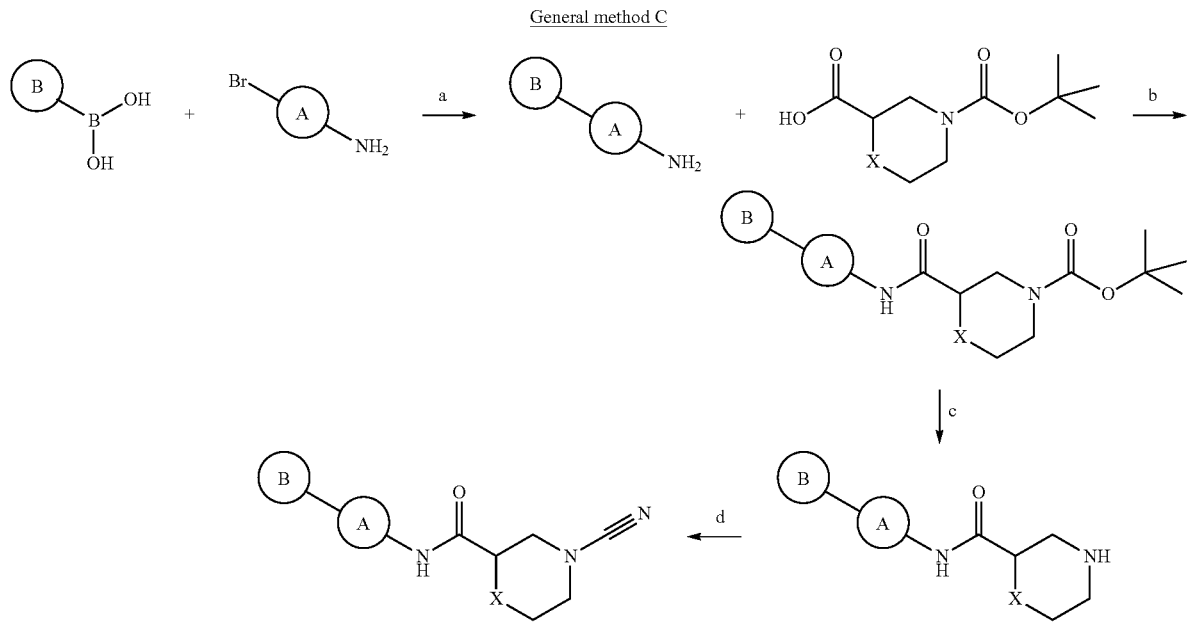

In a further typical synthetic procedure, an amine is attached to an aromatic ring substituted with a halogen, typically Cl, Br or I. Before the amide coupling reaction, a metal catalysed C—C bond forming reaction is conducted, typically a Sukuki reaction, to introduce a second aromatic ring. The final three steps are conducted as described in General method A.

Intermediate A (2R)-4-(Tert-butoxycarbonyl)-5-methylmorpholine-2-carboxylic acid General method D

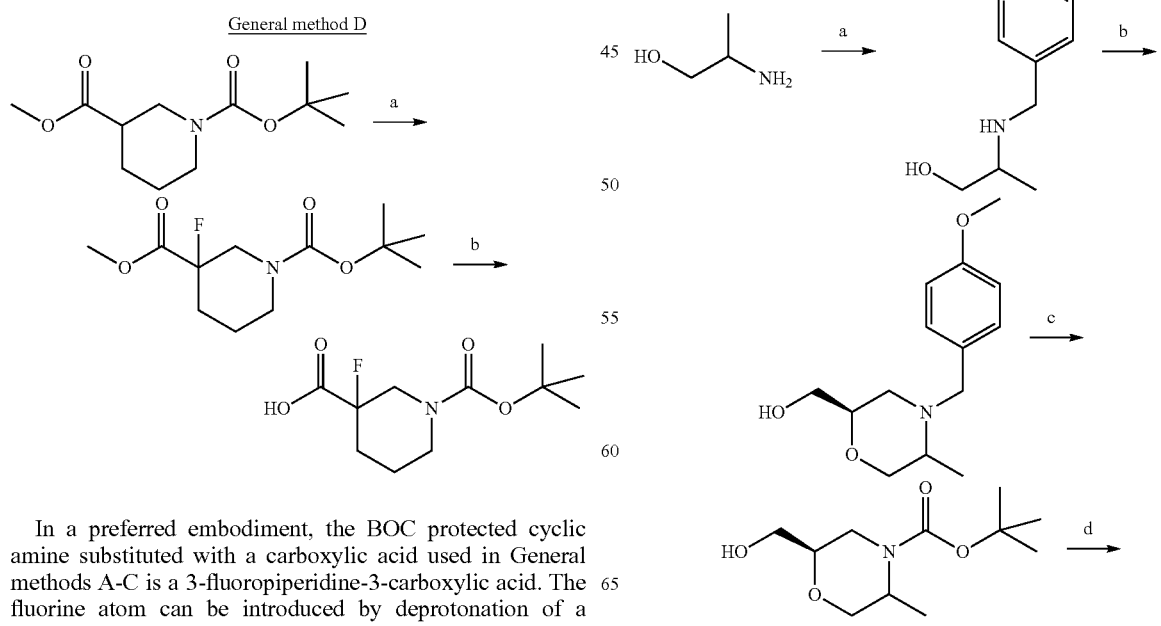

In a preferred embodiment, the BOC protected cyclic amine substituted with a carboxylic acid used in General methods A-C is a 3-fluoropiperidine-3-carboxylic acid. The fluorine atom can be introduced by deprotonation of a piperidine substituted with a carboxylate ester using a strong

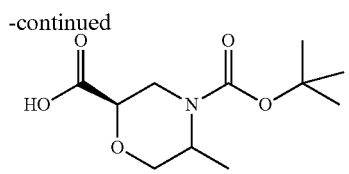

Step a. To a solution of 2-aminopropan-1-ol (CAS Number 6168-72-5; 3.030 g, 40.4 mmol) and 4-methoxybenzaldehyde (5.000 g, 36.7 mmol) in MeOH (30 ml) was added NaHCO₃ (6.170 g, 73.4 mmol) at rt. The reaction mixture was heated at 80° C. for 16 h. The reaction was cooled to rt and stirred for 1 h. The resulting mixture was then cooled to 0° C. and treated portion-wise with NaBH₄ (1.380 g, 36.7 mmol). The reaction mixture was stirred at rt for 1 h. The resulting mixture was concentrated under reduced pressure and poured into 2M HCl (250 ml). The mixture was neutralized by portion-wise addition of NaHCO₃ (20 g) and then extracted with EtOAc (3×300 ml) followed by 10% IPA: chloroform mixture (6×100 ml). The combined organic layer was dried over Na₂SO₄, filtered and concentrated under reduced pressure to yield 2-((4-methoxybenzyl) amino)propan-1-ol (7.40 g, 37.9 mmol). This material was used for next step without further purification. LCMS: Method C, 1.285 min, MS: ES+ 196.33.

Step b. To a solution of 2-((4-methoxybenzyl) amino) propan-1-ol (7.40 g, 37.9 mmol) and (S)-2-(chloromethyl) oxirane (CAS Number 67843-74-7; 3.510 g, 37.9 mmol) in toluene (30 ml) was added lithium perchlorate (4.84 g, 45.5 mmol) at 0° C. The reaction mixture was stirred at rt for 48 h. Sodium methoxide (30% solution in MeOH; 37 ml) was added to the reaction mixture at 0° C. The reaction mixture was warmed to rt and stirred for 3 days. The reaction mixture was concentrated under reduced pressure and poured into NH₄Cl solution (150 ml) and extracted with EtOAc (5×150 ml). The combined organic layer was dried over Na₂SO₄, filtered and concentrated under reduced pressure. The residue was purified by column chromatography (35% EtOAc in hexane) yielding ((2R)-4-(4-methoxybenzyl)-5-methylmorpholin-2-yl)methanol (4.95 g, 19.71 mmol). LCMS: Method C, 1.285 min, MS: ES+ 196.33.

Step c. To a solution of ((2R)-4-(4-methoxybenzyl)-5-methylmorpholin-2-yl)methanol (3.720 g, 14.8 mmol) in EtOH (40 ml) was added poly(methylhydroxysiloxane) (3.72 g, w/w) at 0° C. The reaction mixture was stirred for 15 min before addition of Pd(OH)₂ (20%, 50% moisture; 1.86 g, 50% w/w). The reaction mixture was stirred for a further 15 min at 0° C. and then treated with a solution of di-tert-butyl dicarbonate (6.450 g, 29.6 mmol) in EtOH (10 ml). The reaction mixture was warmed to rt and stirred for 2 h. The resulting mixture was filtered through hyflow and washed with MeOH (30 ml). The combined filtrate was concentrated under reduced pressure. The residue was purified by column chromatography (3.5% MeOH in DCM) yielding tert-butyl (2R)-2-(hydroxymethyl)-5-methyl-morpholine-4-carboxylate (2.60 g, 11.25 mmol). LCMS: Method A, 3.166, 3.623 min, MS: ES+ 232.1, 232.1.

Step d. To a solution of tert-butyl (2R)-2-(hydroxymethyl)-5-methylmorpholine-4-carboxylate (2.60 g, 11.25 mmol) in DCM (50 ml) was added TEMPO (0.351 g, 2.249 mmol) at 0° C. Iodobenzene diacetate (7.246 g, 22.5 mmol) was added and the reaction mixture was stirred at rt for 48 h. The resulting mixture was quenched with MeOH (5 ml) and stirred at rt for 15 min. The resulting mixture was concentrated under reduced pressure. The residue was basified with saturated NaHCO₃ solution (50 ml) and extracted with EtOAc (2×50 ml). The aqueous layer was separated and acidified with 0.1M HCl (30 ml). The resulting mixture was extracted with EtOAc (4×100 ml). The combined organic layer was dried over Na₂SO₄, filtered and concentrated under reduced pressure to yield (2R)-4-(tert-butoxycarbonyl)-5-methylmorpholine-2-carboxylic acid (2.200 g, 8.97 mmol). This material was used for next step without further purification. LCMS: Method E, 25.864, 26.170 min, MS: ES− 244.1, 244.1.

Intermediate B Tert-butyl 4-(3-(4,4,5,5-tetramethyl-1,3,2-dioxaborolan-2-yl)phenyl)-1H-pyrazole-1-carboxylate

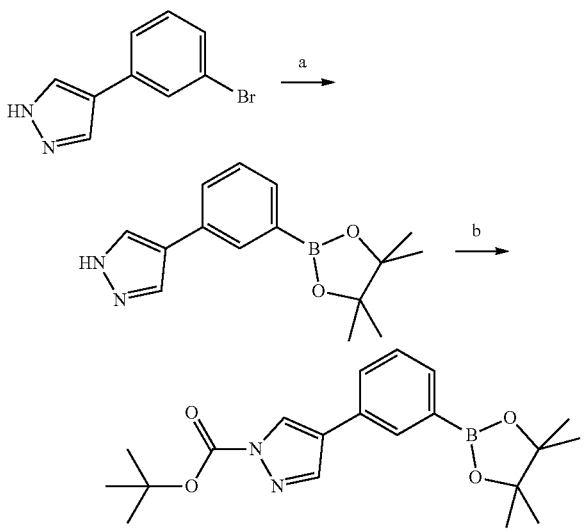

Step a. To a stirred solution of 4-(3-bromophenyl)-1H-pyrazole (CAS Number 916792-28-4; 0.400 g, 1.79 mmol) in 1,4-dioxane (15 ml) was added bis(pinacolato)diboron (0.680 g, 2.69 mmol) and potassium acetate (0.439 g, 4.48 mmol) at rt. The reaction mixture was degassed for 5 min before addition of Pd(dppf)Cl₂ (0.131 g, 0.179 mmol). The reaction mixture was heated at 100° C. for 3 h. The reaction was cooled to rt, diluted with water (200 ml) and extracted with EtOAc (3×100 ml). The combined organic phase was dried over anhydrous Na₂SO₄, filtered and concentrated under reduced pressure. The residue was purified by column chromatography (10% EtOAc in hexane) yielding 4-(3-(4,4,5,5-tetramethyl-1,3,2-dioxaborolan-2-yl)phenyl)-1H-pyrazole (0.420 g, 1.555 mmol). LCMS: Method C, 2.036 min, MS: ES+ 271.50.

Step b. To a solution of 4-(3-(4,4,5,5-tetramethyl-1,3,2-dioxaborolan-2-yl)phenyl)-1H-pyrazole (0.420 g, 1.55 mmol) in THF (12 ml) was added TEA (0.650 ml, 4.66 mmol) and di-tert-butyl dicarbonate (0.406 g, 1.86 mmol) at rt. The reaction mixture was stirred at rt for 16 h. The resulting mixture was diluted with water (150 ml) and extracted with EtOAc (3×100 ml). The combined organic phase was washed with brine solution (50 ml), dried over anhydrous Na₂SO₄, filtered and concentrated under reduced pressure. The residue was purified by column chromatography (5% EtOAc in hexane) yielding tert-butyl 4-(3-(4,4,5,5-tetramethyl-1,3,2-dioxaborolan-2-yl)phenyl)-1H-pyrazole-1-carboxylate (0.500 g, 1.35 mmol). LCMS: Method C, 2.669 min, MS: ES+ 315.40 [M-56].

Intermediate C 5-Chloropyridazin-3-amine

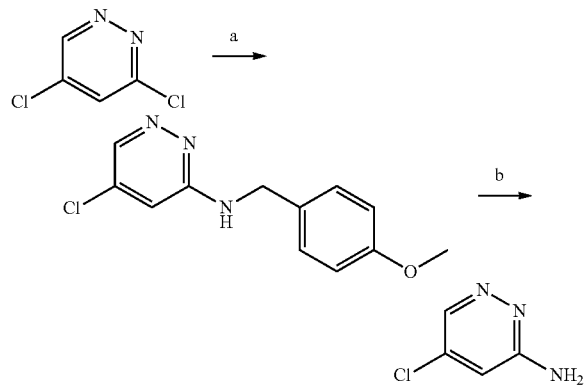

Step a. To a stirred solution of 3,5-dichloropyridazine (CAS Number 1837-55-4; 1.500 g, 10.1 mmol) and (4-methoxyphenyl)methanamine (CAS Number 2393-23-9; 1.650 g, 12.1 mmol) in DMF (10 ml) was added $K_2CO_3$ (2.780 g, 20.1 mmol) and KI (3.340 g, 20.13 mmol) at rt. The reaction mixture was heated at 120° C. for 16 h. The resulting mixture was cooled to rt, diluted with ice cold water (100 ml) and extracted with EtOAc (4×25 ml). The combined organic phase was washed with brine solution (50 ml), dried over anhydrous $Na_2SO_4$, filtered and concentrated under reduced pressure. The residue was purified by column chromatography (53% EtOAc in hexane) yielding 5-chloro-N-(4-methoxy-benzyl)pyridazin-3-amine (3.100 g, quantitative). LCMS: Method C, 1.646 min, MS: ES+ 250.38.

Step b. A solution of 5-chloro-N-(4-methoxybenzyl) pyridazin-3-amine (2.000 g, 8.00 mmol) in TFA (20 ml) was heated at 80° C. for 16 h. The resulting reaction mixture was concentrated under reduced pressure. The obtained residue was triturated using MTBE (20 ml) and dried under vacuum yielding 5-chloropyridazin-3-amine (1.800 g, quantitative). MS: ES+ 130.18.

Intermediate D (R)-1-(Tert-butoxycarbonyl)-3-fluoropiperidine-3-carboxylic acid

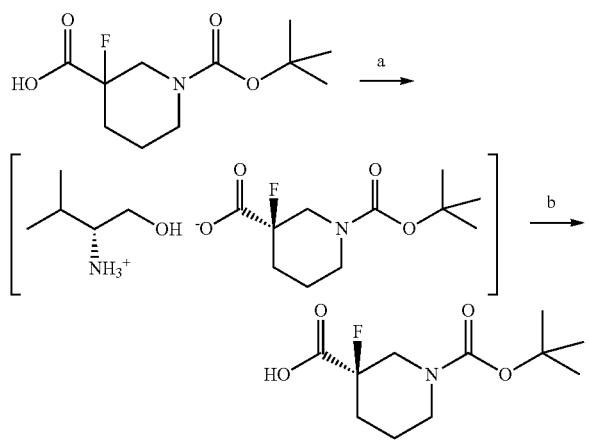

Step a. To a solution of 1-(tert-butoxycarbonyl)-3-fluoropiperidine-3-carboxylic acid (CAS Number 934342-39-9; 285.3 g, 1.15 mol) in MeCN (1.4 L containing 1.5% of water) was added a solution of D-valinol (107.1 g, 1.04 mol) in MeCN (1.4 L containing 1.5% of water). A solid precipitated and the mixture was stirred at reflux until complete dissolution of the solids and then stirring continued at rt for 16 h. The solids obtained were filtered off and washed with MeCN (500 ml). The absolute stereochemistry of a sample of the crystalline material was determined as the (R)-2-amino-3-methylbutan-1-ol (D-valinol) salt of (R)-1-(tert-butoxycarbonyl)-3-fluoropiperidine-3-carboxylic acid by single crystal X-ray diffraction.

Step b. The collected solids were suspended in DCM and treated with a 0.5 M solution of hydrochloric acid. The organic phase was washed two times with a 0.5 M solution of hydrochloric acid, dried over magnesium sulfate, filtered and concentrated under vacuum to give 110 g of the title product (37% yield) in 98% ee (the enantiomeric excess of this material was checked by derivatization of a sample with aniline). $^1$H NMR (300 MHz, $CD_3OD$) δ ppm: 4.14 (bs, 1H), 3.98-4.02 (d, 1H), 3.30-3.50 (m, 1H), 2.91 (bs, 1H), 1.95-2.08 (m, 2H), 1.59-1.80 (m, 2H), 1.45 (s, 9H).

Example 1 (R)-4-cyano-N-(4-phenylpyridin-2-yl) morpholine-2-carboxamide (Prepared According to General Method A)

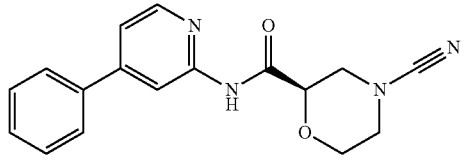 [SMILES: N#CN1CCO[C@@H](C(=O)Nc2cc(-c3ccccc3)ccn2)C1]

Step a. To a solution of (R)-4-BOC-2-morpholinecarboxylic acid (CAS Number 884512-77-0; 0.250 g, 1.08 mmol) in DMF (15 ml) was added HATU (0.617 g, 1.62 mmol) at rt. The reaction mixture was stirred at rt for 30 min. 4-Phenylpyridin-2-ylamine (CAS Number 60781-83-1; 0.184 g, 1.08 mmol) and TEA (0.46 ml, 3.246 mmol) were added and the reaction mixture was stirred at rt for 72 h. The resulting reaction mixture was poured into water (25 ml) and extracted with EtOAc (3×25 ml). The combined organic layer was dried over $Na_2SO_4$, filtered and concentrated under reduced pressure. The resulting residue was purified by flash chromatography (4% MeOH in DCM) yielding tert-butyl (R)-2-((4-phenylpyridin-2-yl)carbamoyl)morpholine-4-carboxylate (0.115 g, 0.300 mmol). LCMS: Method C, 2.423, MS: ES+ 384.38; $^1$H NMR (400 MHz, DMSO-d6) δ ppm: 9.86 (s, 1H), 8.41 (d, J=5.2 Hz, 1H), 8.36 (s, 1H), 7.74 (d, J=6.8 Hz, 2H), 7.48-7.57 (m, 4H), 4.17-4.20 (m, 1H), 4.01-4.03 (m, 2H), 3.71-3.74 (m, 1H), 3.53-3.58 (m, 1H), 2.89-3.01 (m, 2H), 1.42 (s, 9H).

Step b. To a solution of tert-butyl (R)-2-((4-phenylpyridin-2-yl)carbamoyl)morpholine-4-carboxylate (0.110 g, 0.287 mmol) in DCM (5 ml) was added TFA (0.5 ml) at rt. The reaction mixture was stirred at rt for 2 h. The resulting reaction mixture was evaporated under reduced pressure yielding (R)—N-(4-phenylpyridin-2-yl)morpholine-2-carboxamide TFA salt (0.105 g, quantitative). This material was used directly for the next step without further purification. LCMS: Method C, 1.592 min, MS: ES+ 284.28.

Step c. To a solution of (R)—N-(4-phenylpyridin-2-yl) morpholine-2-carboxamide TFA salt (0.100 g, 0.251 mmol) in THF (10 ml) was added $K_2CO_3$ (0.173 g, 1.259 mmol) at rt. The reaction mixture was stirred at rt for 15 min. Cyanogen bromide (0.040 g, 0.377 mmol) was added and the reaction mixture was stirred at rt for 30 min. The resulting reaction mixture was filtered through celite bed, washed with DCM (2×5 ml), and the combined filtrate was washed with water (2×2 ml). The resulting mixture was poured into water (30 ml) and extracted with EtOAc (3×30 ml). The combined organic layer was dried over $Na_2SO_4$, filtered and concentrated under reduced pressure. The residue was purified by chromatography (100% DCM) yielding the title compound (0.053 g, 0.17 mmol). LCMS: Method C, 2.136, MS: ES+ 309.03; $^1$H NMR (400 MHz, DMSO-d6) δ ppm: 10.13 (s, 1H), 8.41 (d, J=5.2 Hz, 1H), 8.34 (s, 1H), 7.74 (d, J=6.8 Hz, 2H), 7.48-7.57 (m, 4H), 4.38-4.41 (m, 1H), 3.97-4.01 (m, 1H), 3.68-3.74 (m, 1H), 3.57-3.60 (m, 1H), 3.23-3.32 (m, 3H).

Example 2 4-Cyano-N-(5-(4-fluorophenyl)thiazol-2-yl)morpholine-2-carboxamide (Prepared According to General Method B)

Step a. To a solution of 5-bromothiazol-2-amine hydrobromide (CAS Number 61296-22-8; 0.500 g, 1.92 mmol) in THF (10 ml) was added N—BOC-2-morpholinecarboxylic acid (CAS Number 189321-66-2; 0.533 g, 2.30 mmol) at 0° C. T3P (50% in EtOAc) (1.80 ml, 2.88 mmol) and DIPEA (1.00 ml, 5.76 mmol) were added to the reaction mixture. The reaction mixture was stirred at rt for 1 h. The resulting reaction mixture was diluted with water (50 ml) and extracted with EtOAc (3×50 ml). The combined organic phase was washed with brine solution (100 ml), dried over $Na_2SO_4$, filtered and concentrated under reduced pressure. The resulting residue was purified by column chromatography (1% MeOH in DCM) to yield tert-butyl 2-((5-bromothiazol-2-yl)carbamoyl)morpholine-4-carboxylate (0.260 g, 0.66 mmol). LCMS: Method C, 2.318 min, MS: ES+ 336.10, 338.1 [M-56].

Step b. To a solution of tert-butyl 2-((5-bromothiazol-2-yl)carbamoyl)morpholine-4-carboxylate (0.400 g, 1.02 mmol) in 1,4-dioxane:water (9:1, 10 ml) was added $K_2CO_3$ (0.704 g, 5.10 mmol) and (4-fluorophenyl)boronic acid (CAS Number 1765-93-1; 0.280 g, 2.04 mmol) at rt. The reaction mixture was degassed for 15 min before addition of Pd(PPh$_3$)$_4$ (0.058 g, 0.051 mmol). The reaction mixture was heated at 80° C. for 8 h then cooled to rt, diluted with water (50 ml and extracted with EtOAc (3×50 ml). The combined organic phase was washed with brine solution (100 ml), dried over $Na_2SO_4$, filtered and concentrated under reduced pressure. The residue was purified by column chromatography (35% EtOAc in hexane) to yield tert-butyl 2-((5-(4-fluorophenyl)thiazol-2-yl)-carbamoyl)morpholine-4-carboxylate (0.346 g, 0.85 mmol). LCMS: Method C, 2.497 min, MS: ES+ 408.35

Steps c, d. The title compound was synthesised from the intermediate above using a procedure similar to that described for Example 1, steps b, c. LCMS: Method B, 3.868 min, MS: ES+ 333.23; $^1$H NMR (400 MHz, DMSO-d$_6$) δ ppm: 12.37 (s, 1H), 7.89 (s, 1H), 7.60-7.67 (m, 2H), 7.25-7.29 (m, 2H), 4.42-4.45 (m, 1H), 3.93-3.96 (m, 1H), 3.68-3.71 (m, 1H), 3.50-3.68 (m, 1H), 3.23-3.32 (m, 3H).

Example 3 4-Cyano-N-(3-propoxy-4-(1H-pyrazol-5-yl)phenyl)morpholine-2-carboxamide (Prepared According to General Method B)

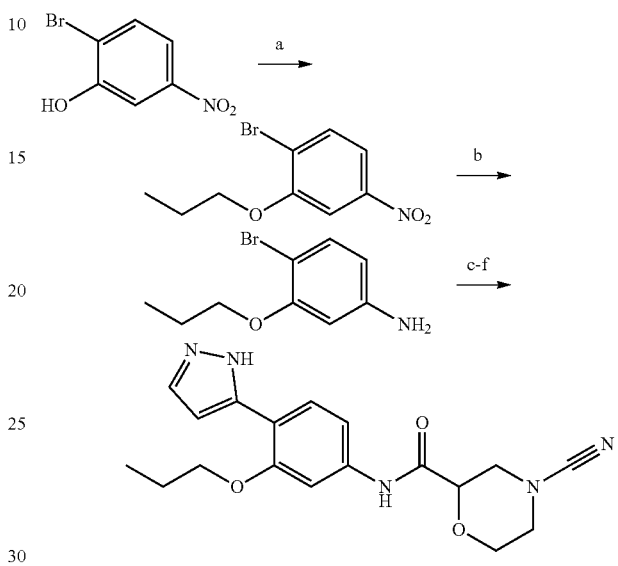

Step a. To a solution of 2-bromo-5-nitrophenol (CAS Number 52427-05-1; 0.8 g, 3.67 mmol) in DMF (10 ml) was added 60% NaH in mineral oil (0.220 g, 9.17 mmol) portion-wise at 0° C. The reaction mixture stirred for 15 min at 0° C. and then treated drop wise with n-propyl iodide (1.56 g, 9.17 mmol). The reaction mixture was warmed to rt and stirred for 2 h. The reaction was quenched with ice cold water (60 ml) and extracted with EtOAc (3×100 ml). The combined organic phase was washed with brine (50 ml), dried over $Na_2SO_4$, filtered and concentrated under reduced pressure to give 1-bromo-4-nitro-2-propoxybenzene (0.77 g, 2.960 mmol). $^1$H NMR (400 MHz, DMSO-d6) δ ppm: 7.90 (d, J=8.8 Hz, 1H), 7.81 (d, J=2.4 Hz, 1H), 7.75 (dd, J=8.8, 2.8 Hz, 1H), 4.17 (t, J=6.4 Hz, 2H), 1.75-1.83 (m, 2H), 1.28 (t, J=7.2 Hz, 3H).

Step b. To a stirred solution of 1-bromo-4-nitro-2-propoxybenzene (0.750 g, 2.88 mmol) in THF:water (1:1, 10 ml) was added iron powder (0.805 g, 14.4 mmol) followed by NH$_4$Cl (0.771 g, 14.4 mmol) at rt. The resulting reaction mixture was heated at 60° C. for 18 h. The reaction was cooled to rt and filtered through celite hyflow. The celite bed was washed with EtOAc (50 ml) and water (20 ml). The filtrate was extracted with EtOAc (3×100 ml). The combined organic phase was washed with brine solution (50 ml), dried over $Na_2SO_4$, filtered and concentrated under reduced pressure to give 4-bromo-3-propoxyaniline (0.61 g, 2.65 mmol). LCMS: Method C, 1.185 min, MS: ES+ 230.30.

Step c. To a solution of N—BOC-morpholine-2-carboxylic acid (CAS Number 189321-66-2; 0.451 g, 1.96 mmol) in THF (5 ml) were added DIPEA (0.70 ml, 3.91 mmol) and HATU (0.991 g, 2.61 mmol) at 0° C. The reaction mixture was stirred at 0° C. for 30 min. A solution of 4-bromo-3-propoxyaniline (0.300 g, 1.30 mmol) in THF (1 ml) was added dropwise to the reaction mixture at 0° C. The reaction mixture was stirred at rt for 30 min. The reaction was poured into water (50 ml) and extracted with EtOAc (2×50 ml). The combined organic phases were dried over Na₂SO₄ and evaporated under reduced pressure. The residue was purified by column chromatography (40% EtOAc in hexane) to yield (tert-butyl 2-((4-bromo-3-propoxyphenyl)carbamoyl)morpholine-4-carboxylate) (0.450 g, 1.01 mmol). LCMS: Method C, 2.527 min, MS: ES+ 443.54, 445.00.

Step d. To a solution of (tert-butyl 2-((4-bromo-3-propoxyphenyl)carbamoyl) morpholine-4-carboxylate) (0.400 g, 0.902 mmol) and 1H-pyrazole-3-boronic acid (CAS Number 376584-63-3; 0.151 g, 1.35 mmol) in DMF:water (8:2, 5 ml) was added Na₂CO₃ (0.287 g, 2.71 mmol) at rt. The reaction mixture was degassed for 15 min before addition of PdCl₂(dppf) (0.066 g, 0.090 mmol). The reaction mixture was heated at 130° C. under microwave irradiation for 1 h. The resulting reaction mixture was cool to rt and filtered over celite. The filtrate was diluted with water (50 ml) and extracted with EtOAc (2×40 ml). The combined organic phases were dried over Na₂SO₄ and evaporated under reduced pressure. The residue was purified by column chromatography (50% EtOAc in hexane) to yield (tert-butyl 2-((3-propoxy-4-(1H-pyrazol-5-yl)phenyl)carbamoyl)-morpholine-4-carboxylate (0.317 g, 0.735 mmol). LCMS: Method C, 2.104 min, MS: ES+ 431.00.

Steps e, f. The title compound was synthesised from the intermediate above using a procedure similar to that described for Example 1, steps b, c. LCMS: Method A, 3.765 min, MS: ES+ 356.16; ¹H NMR (400 MHz, DMSO-d6) δ ppm: 12.59 (s, 1H), 9.65 (s, 1H), 7.66-7.78 (m, 2H), 7.50 (s, 1H), 7.32 (d, J=7.6 Hz, 1H), 6.68 (s, 1H), 4.28-4.31 (m, 1H), 3.98-4.07 (m, 3H), 3.74-3.80 (m, 1H), 3.45-3.58 (m, 1H), 3.23-3.35 (m, 3H), 1.79-1.87 (m, 2H), 1.00-1.10 (m, 3H).

Example 4 (R)-4-Cyano-N-(6-(3-cyanophenyl)pyrimidin-4-yl)morpholine-2-carboxamide (Prepared According to General Method B)

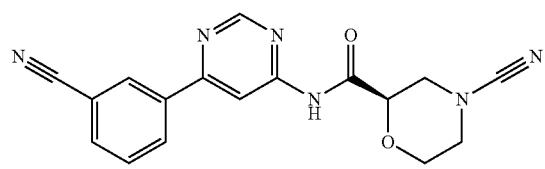 [SMILES: N#Cc1cccc(-c2cc(NC(=O)[C@H]3CN(C#N)CCO3)ncn2)c1]

Step a. To a solution of 4-amino-6-chloropyrimidine (CAS Number 5305-59-9; 0.145 g, 1.12 mmol) in pyridine (4.06 ml) was added (R)—N—BOC-morpholine-2-carboxylic acid (CAS Number 884512-77-0; 0.310 g, 1.34 mmol) at 0° C. POCl₃ (0.514 g, 3.36 mmol) was added drop wise to reaction mixture at 0° C. The reaction mixture was stirred at 0° C. for 10 min. The reaction was diluted with water (40 ml) extracted with EtOAc (2×30 ml). The combined organic phase was washed with saturated citric acid solution (50 ml), dried over Na₂SO₄, filtered and concentrated under reduced pressure. The residue was purified by column chromatography (32% EtOAc in hexane) to yield tert-butyl (R)-2-((6-chloropyrimidin-4-yl)carbamoyl)morpholine-4-carboxylate (0.340 g, 0.99 mmol). LCMS: Method C, 1.992 min, MS: ES+ 287.35 (M-56).

Steps b-d. The title compound was synthesised from the intermediate above using a procedure similar to that described for Example 3, steps d-f. LCMS: Method B, 3.616 min, MS: ES+ 335.48; ¹H NMR (400 MHz, DMSO-d₆) δ ppm: 10.85 (s, 1H), 9.05 (s, 1H), 8.56 (s, 1H), 8.49 (s, 1H), 8.39 (d, J=8.0 Hz, 1H), 8.04 (d, J=7.6 Hz, 1H), 7.78 (t, J=8.0 Hz, 1H), 4.42-4.45 (m, 1H), 3.96-3.99 (m, 1H), 3.67-3.74 (m, 1H), 3.58-3.62 (m, 1H), 3.23-3.30 (m, 3H).

Example 5 4-Cyano-N-(4-(1-methyl-1H-pyrazol-4-yl)phenyl)morpholine-2-carboxamide (Prepared According to General Method C)

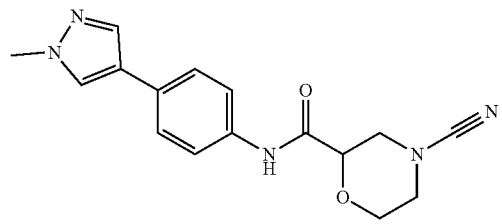 [SMILES: Cn1cc(-c2ccc(NC(=O)C3CN(C#N)CCO3)cc2)cn1]

Step a. To a solution of 4-bromoaniline (1.000 g, 5.81 mmol) and 1-methyl-4-(4,4,5,5-tetramethyl-1,3,2-dioxaborolan-2-yl)-1H-pyrazole (CAS Number 761446-44-0; 1.200 g, 5.81 mmol) in DMF:water (9:1, 10 ml) was added Na₂CO₃ (1.230 g, 11.6 mmol) at rt. The resulting reaction mixture was degassed for 15 min before addition of PdCl₂(dppf) (0.424 g, 0.581 mmol). The reaction mixture was heated at 110° C. for 1 h. The reaction was cooled to rt, diluted with water (150 ml) and extracted with EtOAc (2×150 ml). The combined organic phase was dried over Na₂SO₄, filtered and concentrated under reduced pressure. The residue was purified by column chromatography (50% EtOAc in hexane) to yield 4-(1-methyl-1H-pyrazol-4-yl)aniline (0.52 g, 3.005 mmol). LCMS: Method C, 0.859 min, MS: ES+ 174.05

Step b. To a solution of 4-(1-methyl-1H-pyrazol-4-yl)aniline (0.150 g, 0.867 mmol) in DCM (10 ml) were added 4-(tert-butoxycarbonyl)morpholine-2-carboxylic acid (CAS Number 189321-66-2; 0.200 g, 0.865 mmol) and pyridine (0.69 ml, 8.65 mmol) at 0° C. POCl₃ (0.88 ml, 9.51 mmol) was added drop wise to the reaction mixture at 0° C. The reaction mixture was stirred at rt for 30 min. The resulting mixture was poured into NaHCO₃ solution (100 ml) and extracted with EtOAc (2×150 ml). The combined organic phase was dried over Na₂SO₄, filtered and concentrated under reduced pressure to yield tert-butyl 2-((4-(1-methyl-1H-pyrazol-4-yl)phenyl)carbamoyl)morpholine-4-carboxylate (0.300 g, quantitative). LCMS: Method C, 2.041 min, MS: ES+ 387.40

Steps c, d. The title compound was synthesised from the intermediate above using a procedure similar to that described for Example 1, steps b, c. LCMS: Method A, 3.239 min, MS: ES+ 312.05; ¹H NMR (400 MHz, DMSO-d₆) δ ppm: 9.87 (s, 1H), 8.07 (s, 1H), 7.81 (s, 1H), 7.65 (d, J=8.4 Hz, 2H), 7.50 (d, J=8.4 Hz, 2H), 4.27-4.30 (m, 1H), 3.96-3.99 (m, 1H), 3.85 (s, 3H), 3.70-3.76 (m, 1H), 3.54-3.57 (m, 1H), 3.23-3.32 (m, 3H).

Example 6 (S)-2-(5-Phenyl-2,3-dihydro-1H-pyrrolo[2,3-b]pyridine-1-carbonyl)morpholine-4-carbonitrile (Prepared According to General Method C)

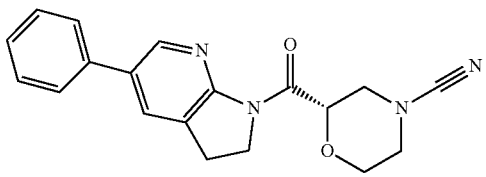 [SMILES: N#CN1CCO[C@H](C(=O)N2CCc3cc(-c4ccccc4)cnc32)C1]

Step a. To a solution of 5-bromo-2,3-dihydro-1H-pyrrolo(2,3-b)pyridine (CAS Number 115170-40-6; 0.300 g, 1.507 mmol) in 1,4-dioxane:water (1:1, 8 ml) were added phenylboronic acid (0.294 g, 2.412 mmol) and K$_2$CO$_3$ (0.624 g, 4.52 mmol) at rt. The reaction mixture was degassed for 30 min before addition of Pd(PPh$_3$)$_4$ (0.087 g, 0.075 mmol) then heated at 80° C. for 1 h. The reaction was cooled to rt, poured into water (100 ml) and extracted with EtOAc (3×50 ml). The combined organic phase was dried over Na$_2$SO$_4$, filtered and concentrated under reduced pressure yielding 5-phenyl-2,3-dihydro-1H-pyrrolo[2,3-b]pyridine (0.440 g, 2.24 mmol). MS: ES+ 197.1.

Step b. To a solution of (S)-4-(tert-butoxycarbonyl)morpholine-2-carboxylic acid (CAS Number 868689-63-8; 0.100 g, 0.432 mmol) in THF (6 ml) was added HATU (0.197 g, 0.518 mmol) and DIPEA (0.15 ml, 0.86 mmol) at rt. The reaction mixture was stirred at rt for 20 min before addition of 5-phenyl-2,3-dihydro-1H-pyrrolo[2,3-b]pyridine (0.067 g, 0.345 mmol). The reaction mixture was stirred at rt for 1 h then poured into saturated NaHCO$_3$ solution (100 ml) and extracted with EtOAc (2×50 ml). The combined organic phase was dried over Na$_2$SO$_4$, filtered and concentrated under reduced pressure yield tert-butyl (S)-2-(5-phenyl-2,3-dihydro-1H-pyrrolo[2,3-b]pyridine-1-carbonyl)-morpholine-4-carboxylate (0.080 g, 0.195 mmol). LCMS: Method C, 2.374 min, MS: ES+ 410.38.

Steps c, d. The title compound was synthesised from the intermediate above using a procedure similar to that described for Example 1, steps b, c. LCMS: Method A, 5.813 min, MS: ES+ 335.15; $^1$H NMR (400 MHz, DMSO-d$_6$) δ ppm: 8.46 (s, 1H), 8.00 (s, 1H), 7.69-7.71 (m, 2H), 7.47-7.50 (m, 2H), 7.38-7.41 (m, 1H), 5.80-5.86 (m, 1H), 3.92-4.07 (m, 3H), 3.72-3.77 (m, 1H), 3.58-3.61 (m, 1H), 3.22-3.30 (m, 3H), 3.12-3.15 (m, 2H).

Example 7 N-(6-(1H-Pyrazol-4-yl)benzo[d]thiazol-2-yl)-4-cyanomorpholine-2-carboxamide (Prepared According to General Method C)

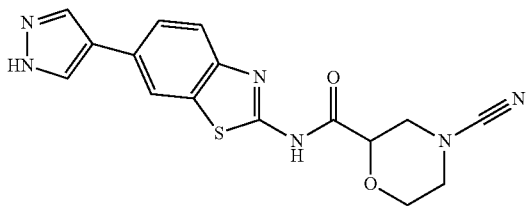 [SMILES: N#CN1CCOC(C(=O)Nc2nc3ccc(-c4cn[nH]c4)cc3s2)C1]

Step a. To a solution of 6-bromobenzo[d]thiazol-2-amine (CAS Number 15864-32-1; 0.300 g, 1.31 mmol) and 4-(4,5,5-tetramethyl-1,3,2-dioxaborolan-2-yl)-1H-pyrazole (CAS Number 269410-08-4; 0.635 g, 3.27 mmol) in DMF:water (9:1, 10 ml) was added CsF (0.636 g, 4.19 mmol) at rt. The reaction mixture was degassed for 15 min before addition of Pd(PPh$_3$)$_2$Cl$_2$ (0.138 g, 0.196 mmol). The reaction mixture was heated at 140° C. in microwave for 2 h then cooled to rt, diluted with water (50 ml) and extracted with EtOAc (3×50 ml). The combined organic phase was washed with brine solution (50 ml), dried over Na$_2$SO$_4$, filtered and concentrated under reduced pressure. The residue was purified by column chromatography (5% MeOH in DCM) to yield 6-(1H-pyrazol-4-yl)benzo[d]thiazol-2-amine (0.400 g, 1.851 mmol). LCMS: Method C, 1.388 min, MS: ES+ 217.14

Steps b-d. The title compound was synthesised from the intermediate above using a procedure similar to that described for Example 5. LCMS: Method A, 2.150 min, MS: ES+ 354.96; $^1$H NMR (400 MHz, DMSO-d6) δ ppm: 12.97 (s, 1H), 12.46 (s, 1H), 8.24 (s, 1H), 8.15-8.08 (m, 2H), 7.70-7.75 (m, 2H), 4.45-4.48 (m, 1H), 3.94-3.97 (m, 1H), 3.60-3.73 (m, 2H), 3.40-3.47 (m, 1H), 3.22-3.32 (m, 2H).

Example 8 4-Cyano-N-(1-phenyl-1H-imidazol-4-yl)morpholine-2-carboxamide (Prepared According to General Method A)

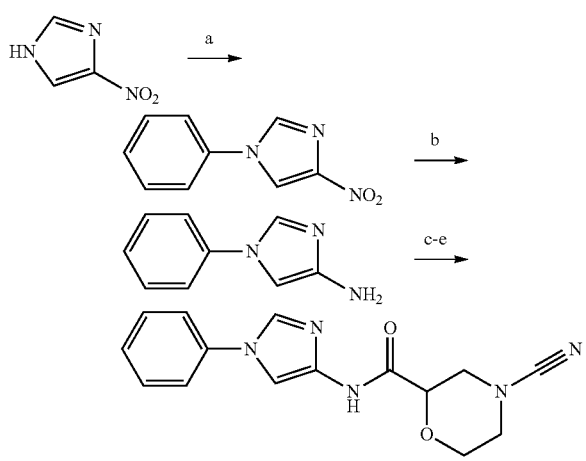

Step a. To a solution of 4-nitroimidazole (5.00 g, 44.2 mmol) in MeOH (40 ml) was added phenylboronic acid (8.77 g, 71.7 mmol), CuCl$_2$ (0.710 g, 5.30 mmol) and NaOH (1.760 g, 44.2 mmol) at rt. The reaction mixture was stirred at 80° C. for 16 h whilst slowly purging with O$_2$ gas throughout the reaction time. The resulting mixture was cooled to rt and concentrated under reduced pressure. The obtained crude material was poured into water (500 ml) and extracted with EtOAc (3×150 ml). The combined organic phase was wash with NaHCO$_3$ solution (200 ml) and dried over Na$_2$SO$_4$, filtered and concentrated under reduced pressure to yield 4-nitro-1-phenyl-1H-imidazole (1.500 g, 7.93 mmol). LCMS: Method C, 1.760 min, MS: ES+ 191.09.

Step b. To a solution of 4-nitro-1-phenyl-1H-imidazole (0.17 g, 0.89 mmol) in THF (5 ml) was added 10% Pd/C (0.1 g) at rt. The reaction mixture was purged with H$_2$ gas for 2 h at rt. The resulting mixture was carefully filtered through celite hyflow and concentrated under reduced pressure to yield 1-phenyl-1H-imidazol-4-amine. This material was directly used for the next step without further purification. LCMS: Method C, 2.858 min, MS: ES+ 159.93.

Steps c-e. The title compound was synthesised from the intermediate above using a procedure similar to that described for Example 1. LCMS: Method A, 3.433 min, MS: ES+ 297.98; $^1$H NMR (400 MHz, DMSO-d6) δ ppm: 10.28 (s, 1H), 8.15 (d, J=1.6 Hz, 1H), 7.71 (d, J=1.6 Hz, 1H), 7.63-7.65 (m, 2H), 7.50-7.53 (m, 2H), 7.35-7.38 (m, 1H), 4.29-4.32 (m, 1H), 3.93-3.96 (m, 1H), 3.65-3.71 (m, 1H), 3.51-3.55 (m, 1H), 3.21-3.30 (m, 3H).

Compounds in Table 1 were synthesised by the general methods A-C (Syn. Met.) as exemplified by Examples 1-8 using 4-(tert-butoxycarbonyl)morpholine-2-carboxylic acid (CAS Number 189321-66-2).

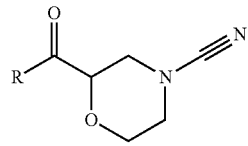

TABLE 1

| Ex | R | Name | Syn. Met. | $^1$H NMR: (400 MHz, DMSO-d$_6$) δ ppm | LCMS Met. | LCMS RT (min) | MS |
|---|---|---|---|---|---|---|---|
| 9 | | N-([1,1'-Biphenyl]-4-yl)-4-ycanomorpholine-2-carboxamide | A | 9.99 (s, 1 H), 7.77 (d, J = 8.4 Hz, 2 H), 7.63-7.66 (m, 4 H), 7.45 (t, J = 8.0 Hz, 2 H), 7.32-7.35 (m, 1 H), 4.30-4.34 (m, 1 H), 3.97-4.00 (m, 1 H), 3.72-3.78 (m, 1 H), 3.55-3.59 (m, 1 H), 3.23-3.32 (m, 3 H) | C | 2.136 | ES+ 308.32 |
| 10 | | 4-Cyano-N-(3-(3-methoxyphenyl)isoxazol-5-yl)morpholine-2-carboxamide | C | 11.84 (s, 1 H), 7.37-7.45 (m, 3 H), 7.05-7.09 (m, 1 H), 6.82 (s, 1 H), 4.39-4.42 (m, 1 H), 3.92-3.97 (m, 1 H), 3.82 (s, 3 H), 3.68-3.75 (m, 1 H), 3.56-3.60 (m, 1 H), 3.31-3.33 (m, 1 H), 3.22-3.28 (m, 2 H) | A | 2.987 | ES+ 329.09 |
| 11 | | 4-Cyano-N-(5-phenyl-1H-pyrazol-3-yl)morpholine-2-carboxamide | A | 12.95 (s, 1 H), 10.20 (s, 1 H), 7.71-7.73 (m, 2 H), 7.43-7.47 (m, 2 H), 7.33-7.37 (m, 1 H), 6.88 (s, 1 H), 4.28-4.31 (m, 1 H), 3.94-3.97 (m, 1 H), 3.66-3.72 (m, 1 H), 3.53-3.56 (m, 1 H), 3.22-3.30 (m, 3 H) | A | 3.417 | ES+ 297.98 |
| 12 | | 4-Cyano-N-(5-phenylpyridin-2-yl)morpholine-2-carboxamide | C | 10.18 (s, 1 H), 8.68 (d, J = 1.2 Hz, 1 H), 8.11-8.17 (m, 2 H), 7.71-7.74 (m, 2 H), 7.47-7.51 (m, 2 H), 7.38-7.42 (m, 1 H), 4.38-4.41 (m, 1 H), 3.96-4.00 (m, 1 H), 3.68-3.75 (m, 1 H), 3.57-3.61 (m, 1 H), 3.23-3.32 (m, 3 H) | B | 3.924 | ES+ 309.26 |
| 13 | | 4-Cyano-N-(5-phenylisoxazol-3-yl)morpholine-2-carboxamide | C | 11.11 (s, 1 H), 7.88-7.91 (m, 2 H), 7.52-7.57 (m, 3 H), 7.32 (s, 1 H), 4.35-4.38 (m, 1 H), 3.93-3.97 (m, 1 H), 3.66-3.73 (m, 1 H), 3.55-3.59 (m, 1 H), 3.22-3.32 (m, 3 H) | B | 3.667 | ES+ 299.22 |
| 14 | | 4-Cyano-N-(4-cyano-[2,4'-bipyridin]-2'-yl)morpholine-2-carboxamide | C | 10.19 (s, 1 H), 9.00 (d, J = 5.2 Hz, 1 H), 8.81 (s, 1 H), 8.59 (s, 1 H), 8.51 (d, J = 5.2 Hz, 1 H), 7.87-7.99 (m, 2 H), 4.39-4.42 (m, 1 H), 3.97-4.00 (m, 1 H), 3.69-3.75 (m, 1 H), 3.57-3.61 (m, 1 H), 3.22-3.32 (m, 3 H) | B | 3.429 | ES+ 335.38 |
| 15 | | N-([1,1'-Biphenyl]-3-yl)-4-cyanomorpholine-2-carboxamide | A | 9.97 (s, 1 H), 7.99 (s, 1 H), 7.61-7.69 (m, 3 H), 7.36-7.50 (m, 5 H), 4.31-4.34 (m, 1 H), 3.97-4.00 (m, 1 H), 3.72-3.78 (m, 1 H), 3.47-3.59 (m, 1 H), 3.17-3.31 (m, 3 H) | A | 4.599 | ES+ 308.04 |

TABLE 1-continued

| Ex | R | Name | Syn. Met. | $^1$H NMR: (400 MHz, DMSO-$d_6$) δ ppm | LCMS Met. | LCMS RT (min) | MS |
|---|---|---|---|---|---|---|---|
| 16 | | 4-Cyano-N-(3-(1-methyl-1H-pyrazol-4-yl)phenyl)morpholine-2-carboxamide | C | 9.83 (s, 1 H), 8.06 (s, 1 H), 7.83 (s, 1 H), 7.76 (s, 1 H), 7.49-7.50 (m, 1 H), 7.28-7.29 (m, 2 H), 4.29-4.32 (m, 1 H), 3.96-3.99 (m, 1 H), 3.87 (s, 3 H), 3.72-3.78 (m, 1 H), 3.54-3.58 (m, 1 H), 3.24-3.34 (m, 3 H) | A | 3.273 | ES+ 311.92 |
| 17 | | 4-Cyano-N-(6-phenylpyridin-3-yl)morpholine-2-carboxamide | A | 10.25 (s, 1 H), 8.91 (d, J = 2.0 Hz, 1 H), 8.20 (dd, J = 8.4, 2.4 Hz, 1 H), 8.03-8.05 (m, 2 H), 7.95 (d, J = 8.8 Hz, 1 H), 7.45-7.49 (m, 2 H), 7.38-7.42 (m, 1 H), 4.35-4.38 (m, 1 H), 3.98-4.01 (m, 1 H), 3.73-3.79 (m, 1 H), 3.56-3.60 (m, 1 H), 3.24-3.34 (m, 3 H) | A | 4.078 | ES+ 309.01 |
| 18 | | 4-Cyano-N-(2'-cyano-[4,4'-bipyridin]-2-yl)morpholine-2-carboxamide | C | 10.34 (s, 1 H), 8.90 (d, J = 5.2 Hz, 1 H), 8.54 (d, J = 5.2 Hz, 1 H), 8.47 (s, 1 H), 8.42 (s, 1 H), 8.09-8.10 (m, 1 H), 7.66-7.68 (m, 1 H), 4.40-4.43 (m, 1 H), 3.97-4.00 (m, 1 H), 3.69-3.75 (m, 1 H), 3.57-3.61 (m, 1 H), 3.22-3.30 (m, 3 H) | A | 3.439 | ES+ 335.01 |
| 19 | | 4-Cyano-N-(3-(3-(trifluoro-methyl)phenyl)isoxazol-5-yl)morpholine-2-carboxamide | A | 11.94 (s, 1 H), 8.20-8.21 (m, 2 H), 7.87-7.89 (m, 1 H), 7.73-7.77 (m, 1 H), 7.00 (s, 1 H), 4.40-4.44 (m, 1 H), 3.93-3.97 (m, 1 H), 3.69-3.75 (m, 1 H), 3.57-3.61 (m, 1 H), 3.24-3.34 (m, 3 H) | A | 4.504 | ES+ 366.90 |

Compounds in Table 2 were synthesised by the general methods A-C (Syn. Met.) as exemplified by Examples 1-8 using (R)-4-(tert-butoxycarbonyl)morpholine-2-carboxylic acid (CAS Number 884512-77-0).

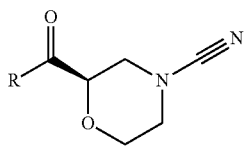

TABLE 2

| Ex | R | Name | Syn. Met. | $^1$H NMR: (400 MHz, DMSO-$d_6$) δ ppm | LCMS Met. | LCMS RT (min) | MS |
|---|---|---|---|---|---|---|---|
| 20 | | (R)-4-Cyano-N-(5-phenylthiazol-2-yl)morpholine-2-carboxamide | A | 12.32 (s, 1 H), 7.93 (s, 1 H), 7.62-7.64 (m, 2 H), 7.40-7.44 (m, 2 H), 7.30-7.33 (m, 1 H), 4.42-4.45 (m, 1 H), 3.92-3.97 (m, 1 H), 3.65-3.72 (m, 1 H), 3.58-3.61 (m, 1 H), 3.23-3.32 (m, 3 H) | A | 2.910 | ES+ 314.87 |
| 21 | | (R)-N-(6-(3-Chlorophenyl)-pyrimidin-4-yl)-4-cyanomorpholine-2-carboxamide | B | 10.85 (s, 1 H), 9.02 (s, 1 H), 8.51 (s, 1 H), 8.09 (s, 1 H), 8.02 (d, J = 7.6 Hz, 1 H), 7.58-7.66 (m, 2 H), 4.41-4.44 (m, 1 H), 3.96-3.99 (m, 1 H), 3.67-3.73 (m, 1 H), 3.58-3.62 (m, 1 H), 3.24-3.34 (m, 3 H) | A | 4.461 | ES+ 343.99 |

TABLE 2-continued

| Ex | R | Name | Syn. Met. | $^1$H NMR: (400 MHz, DMSO-$d_6$) δ ppm | LCMS Met. | LCMS RT (min) | MS |
|---|---|---|---|---|---|---|---|
| 22 | 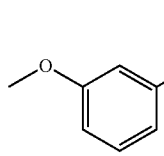 | (R)-4-Cyano-N-(6-(3-methoxy-phenyl)pyrimidin-4-yl)morpholine-2-carboxamide | B | 10.75 (s, 1 H), 9.00 (s, 1 H), 8.50 (s, 1 H), 7.62-7.63 (m, 2 H), 7.49 (t, J = 8.0 Hz, 1 H), 7.14-7.17 (m, 1 H), 4.41-4.44 (m, 1 H), 3.97-4.00 (m, 1 H), 3.85 (s, 3 H), 3.67-3.74 (m, 1 H), 3.58-3.62 (m, 1 H), 3.25-3.33 (m, 3 H) | A | 3.885 | ES+ 340.07 |
| 23 | 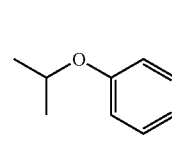 | (R)-4-Cyano-N-(6-(3-isopropoxy-phenyl)pyrimidin-4-yl)morpholine-2-carboxamide | B | 10.74 (s, 1 H), 8.99 (s, 1 H), 8.49 (s, 1 H), 7.58-7.60 (m, 2 H), 7.46 (t, J = 8.0 Hz, 1 H), 7.11-7.14 (m, 1 H), 4.69-4.72 (m, 1 H), 4.41-4.44 (m, 1 H), 3.97-3.99 (m, 1 H), 3.68-3.73 (m, 1 H), 3.58-3.62 (m, 1 H), 3.25-3.33 (m, 3 H), 1.31 (d, J = 6.0 Hz, 6 H) | A | 4.583 | ES+ 368.00 |
| 24 | 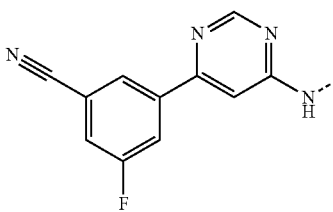 | (R)-4-Cyano-N-(6-(3-cyano-5-fluoro-phenyl)pyrimidin-4-yl)morpholine-2-carboxamide | B | 10.89 (s, 1 H), 9.05 (s, 1 H), 8.54 (s, 1 H), 8.36 (s, 1 H), 8.22 (d, J = 9.1 Hz, 1 H), 8.08 (d, J = 8.4 Hz, 1 H), 4.42-4.45 (m, 1 H), 3.96-4.05 (m, 1 H), 3.67-3.74 (m, 1 H), 3.58-3.62 (m, 1 H), 3.22-3.34 (m, 3 H) | A | 4.038 | ES+ 353.04 |
| 25 | 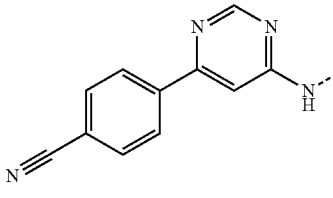 | (R)-4-Cyano-N-(6-(4-cyanophenyl)pyrimidin-4-yl)morpholine-2-carboxamide | B | 10.89 (s, 1 H), 9.07 (s, 1 H), 8.58 (s, 1 H), 8.26 (d, J = 8.8 Hz, 2 H), 8.05 (d, J = 8.4 Hz, 2 H), 4.42-4.45 (m, 1 H), 3.96-3.99 (m, 1 H), 3.67-3.74 (m, 1 H), 3.58-3.62 (m, 1 H), 3.22-3.34 (m, 3 H) | A | 3.592 | ES+ 334.94 |
| 26 | 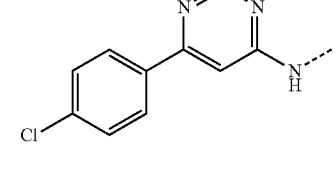 | (R)-N-(6-(4-Chlorophenyl)-pyrimidin-4-yl)-4-cyanomorpholine-2-carboxamide | B | 10.79 (s, 1 H), 9.01 (s, 1 H), 8.52 (s, 1 H), 8.11 (d, J = 8.8 Hz, 2 H), 7.64 (d, J = 8.8 Hz, 2 H), 4.41-4.44 (m, 1 H), 3.97-4.04 (m, 1 H), 3.67-3.74 (m, 1 H), 3.58-3.62 (m, 1 H), 3.22-3.32 (m, 3 H) | A | 4.321 | ES+ 343.99 |
| 27 | 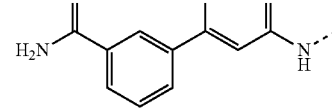 | (R)-N-(6-(3-Carbamoylphenyl)-pyrimidin-4-yl)-4-cyanomorpholine-2-carboxamide | B | 10.78 (s, 1 H), 9.03 (s, 1 H), 8.57 (s, 2 H), 8.23-8.24 (m, 2 H), 8.04-8.0 (m, 1 H), 7.65 (t, J = 8.0 Hz, 1 H), 7.53 (s, 1 H), 4.42-4.45 (m, 1 H), 3.87-4.00 (m, 1 H), 3.68-3.80 (m, 1 H), 3.42-3.62 (m, 2 H), 3.17-3.28 (m, 2 H) | C | 1.445 | ES+ 353.48 |
| 28 | 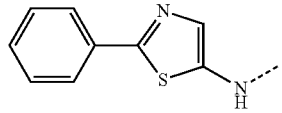 | (R)-4-Cyano-N-(2-phenylthiazol-5-yl)morpholine-2-carboxamide | A | 11.57 (s, 1 H), 7.86-7.88 (m, 2 H), 7.78 (s, 1 H), 7.42-7.48 (m, 3 H), 4.44-4.47 (m, 1 H), 3.96-3.99 (m, 1 H), 3.74-3.80 (m, 1 H), 3.56-3.60 (m, 1 H), 3.35-3.37 (m, 1 H), 3.23-3.29 (m, 2 H) | B | 3.631 | ES+ 315.26 |
| 29 | 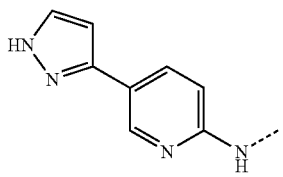 | (R)-N-(5-(1H-Pyrazol-5-yl)pyridin-2-yl)-4-cyanomorpholine-2-carboxamide | B | 13.00 (s, 1 H), 10.08 (s, 1 H), 8.78 (s, 1 H), 8.20-8.22 (m, 1 H), 8.06-8.08 (m, 1 H), 7.82 (s, 1 H), 6.78 (s, 1 H), 4.36-4.39 (m, 1 H), 3.96-3.99 (m, 1 H), 3.67-3.73 (m, 1 H), 3.55-3.59 (m, 1 H), 3.16-3.30 (m, 3 H) | A | 2.952 | ES+ 299.03 |

TABLE 2-continued

| Ex | R | Name | Syn. Met. | ¹H NMR: (400 MHz, DMSO-d₆) δ ppm | LCMS Met. | LCMS RT (min) | MS |
|---|---|---|---|---|---|---|---|
| 30 | | (R)-N-(6-(1H-indazol-4-yl)pyrimidin-4-yl)-4-cyanomorpholine-2-carboxamide | C | 13.41 (s, 1 H), 10.79 (s, 1 H), 9.08 (s, 1 H), 8.68 (s, 1 H), 8.59 (s, 1 H), 7.76-7.82 (m, 2 H), 7.52-7.56 (m, 1 H), 4.43-4.46 (m, 1 H), 3.97-4.02 (m, 1 H), 3.60-3.71 (m, 2 H), 3.35-3.39 (m, 1 H), 3.26-3.30 (m, 2 H) | A | 3.082 | ES+ 350.04 |
| 31 | | (R)-N-(6-(1H-Pyrazol-4-yl)isoquinolin-3-yl)-4-cyanomorpholine-2-carboxamide | B | 13.12 (s, 1 H), 10.03 (s, 1 H), 9.07 (s, 1 H), 8.41 (s, 1 H), 8.45 (s, 1 H), 8.17 (s, 2 H), 8.04 (d, J = 8.8 Hz, 1 H), 7.87 (d, J = 7.2 Hz, 1 H), 4.41-4.44 (m, 1 H), 4.00-4.01 (m, 1 H), 3.74-3.77 (m, 1 H), 3.59-3.62 (m, 1 H), 3.24-3.32 (m, 3 H) | B | 3.219 | ES+ 349.53 |
| 32 | | (R)-4-Cyano-N-(5-phenyl-1,3,4-thiadiazol-2-yl)morpholine-2-carboxamide | A | 12.84 (s, 1 H), 7.94-7.97 (m, 2 H), 7.53-7.55 (m, 3 H), 4.48-4.51 (m, 1 H), 3.94-3.97 (m, 1 H), 3.67-3.73 (m, 1 H), 3.59-3.63 (m, 1 H), 3.23-3.32 (m, 3 H). | B | 3.564 | ES+ 316.26 |

Compounds in Table 3 were synthesised by the general methods A-C (syn. Met.) as exemplified by Examples 1-8 using (S)-4-(tert-butoxycarbonyl)morpholine-2-carboxylic acid (CAS Number 884512-77-0).

Compounds in Table 4 were synthesised by the general methods A-C (Syn. Met.) as exemplified by Examples 1-8 using 1-(tert-butoxycarbonyl)piperidine-3-carboxylic acid (CAS Number 84358-12-3).

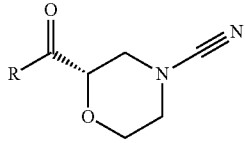

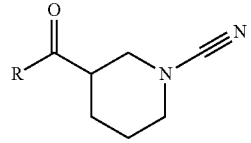

TABLE 3

| Ex | R | Name | Syn. Met. | ¹H NMR: (400 MHz, DMSO-d₆) δ ppm | LCMS Met. | LCMS RT (min) | MS |
|---|---|---|---|---|---|---|---|
| 33 | | (S)-4-Cyano-N-(5-phenylthiazol-2-yl)morpholine-2-carboxamide | A | 12.32 (s, 1 H), 7.93 (s, 1 H), 7.62-7.64 (m, 2 H), 7.40-7.44 (m, 2 H), 7.30-7.33 (m, 1 H), 4.42-4.45 (m, 1 H), 3.92-3.97 (m, 1 H), 3.65-3.72 (m, 1 H), 3.58-3.61 (m, 1 H), 3.23-3.32 (m, 3 H). | B | 3.828 | ES+ 315.23 |
| 34 | | (S)-4-Cyano-N-(isoquinolin-3-yl)morpholine-2-carboxamide | A | 10.09 (s, 1 H), 9.17 (s, 1 H), 8.44 (s, 1 H), 8.08 (d, J = 8.4 Hz, 1 H), 7.94 (d, J = 8.0 Hz, 1 H), 7.72-7.76 (m, 1 H), 7.57-7.59 (m, 1 H), 4.41-4.44 (m, 1 H), 3.99-4.02 (m, 1 H), 3.70-3.77 (m, 1 H), 3.59-3.63 (m, 1 H), 3.23-3.32 (m, 3 H) | B | 3.526 | ES+ 283.28 |
| 35 | | (S)-4-Cyano-N-(4-phenylpyridin-2-yl)morpholine-2-carboxamide | A | 10.12 (s, 1 H), 8.41 (d, J = 5.2 Hz, 1 H), 8.34 (s, 1 H), 7.72-7.74 (m, 2 H), 7.48-7.57 (m, 4 H), 4.38-4.41 (m, 1 H), 3.97-4.00 (m, 1 H), 3.69-3.75 (m, 1 H), 3.57-3.60 (m, 1 H), 3.22-3.30 (m, 3 H) | B | 3.815 | ES+ 309.38 |

TABLE 4

| Ex | R | Name | Syn. Met. | ¹H NMR: (400 MHz, DMSO-d₆) δ ppm | LCMS Met. | LCMS RT (min) | MS |
|---|---|---|---|---|---|---|---|
| 36 | | 1-Cyano-N-(3-propoxy-4-(1H-pyrazol-5-yl)phenyl)piperidine-3-carboxamide | B | 12.78-12.83 (m, 1 H), 10.09-10.16 (m, 1 H), 7.61-7.84 (m, 2 H), 7.49 (s, 1 H), 7.13-7.16 (m, 1 H), 6.64-6.72 (m, 1 H), 3.95-3.99 (m, 2 H), 3.52-3.54 (m, 1 H), 3.30-3.33 (m, 1 H), 3.00-3.14 (m, 2 H), 2.67-2.71 (m, 1 H), 1.93-1.95 (m, 1 H), 1.80-1.85 (m, 2 H), 1.70-1.74 (m, 1 H), 1.55-1.63 (m, 2 H), 1.02-1.04 (m, 3 H) | A | 3.946 | ES+ 354.03 |
| 37 | | 1-Cyano-N-(1-phenyl-1H-imidazol-4-yl)piperidine-3-carboxamide | A | 10.62 (s, 1 H), 8.12 (d, J = 1.6 Hz, 1 H), 7.68 (d, J = 1.6 Hz, 1 H), 7.61-7.63 (m, 2 H), 7.49-7.53 (m, 2 H), 7.33-7.37 (m, 1 H), 3.46-3.50 (m, 1 H), 3.30-3.33 (m, 1 H), 3.09-3.15 (m, 1 H), 2.99-3.05 (m, 1 H), 2.73-2.78 (m, 1 H), 1.89-1.91 (m, 1 H), 1.70-1.72 (m, 1 H), 1.53-1.58 (m, 2 H) | A | 3.575 | ES+ 296.01 |
| 38 | | 1-Cyano-N-(5-phenyl-1H-pyrazol-3-yl)piperidine-3-carboxamide | A | 12.86 (s, 1 H), 10.59 (s, 1 H), 7.70-7.72 (m, 2 H), 7.42-7.46 (m, 2 H), 7.32-7.36 (m, 1 H), 6.88 (s, 1 H), 3.48-3.51 (m, 1 H), 3.30-3.33 (m, 1 H), 3.12-3.17 (m, 1 H), 3.00-3.05 (m, 1 H), 2.70-2.76 (m, 1 H), 1.89-1.91 (m, 1 H), 1.71-1.73 (m, 1 H), 1.56-1.62 (m, 2 H) | A | 3.633 | ES+ 295.95 |
| 39 | | 1-Cyano-N-(5-phenylpyridin-2-yl)piperidine-3-carboxamide | A | 10.73 (s, 1 H), 8.66-8.67 (m, 1 H), 8.09-8.16 (m, 2 H), 7.70-7.72 (m, 2 H), 7.46-7.50 (m, 2 H), 7.37-7.40 (m, 1 H), 3.51-3.55 (m, 1 H), 3.30-3.32 (m, 1 H), 3.11-3.17 (m, 1 H), 3.01-3.07 (m, 1 H), 2.83-2.88 (m, 1 H), 1.96-1.99 (m, 1 H), 1.72-1.74 (m, 1 H), 1.54-1.59 (m, 2 H) | B | 3.924 | ES+ 307.23 |
| 40 | | 1-Cyano-N-(4-phenylpyridin-2-yl)piperidine-3-carboxamide | A | 10.72 (s, 1 H), 8.38 (d, J = 4.8 Hz, 2 H), 7.71-7.73 (m, 2 H), 7.47-7.56 (m, 3 H), 7.42-7.44 (m, 1 H), 3.52-3.56 (m, 1 H), 3.30-3.32 (m, 1 H), 3.11-3.17 (m, 1 H), 3.01-3.07 (m, 1 H), 2.86-2.90 (m, 1 H), 1.96-1.99 (m, 1 H), 1.72-1.74 (m, 1 H), 1.54-1.62 (m, 2 H) | B | 3.766 | ES+ 307.18 |
| 41 | | 1-Cyano-N-(3-phenylisoxazol-5-yl)piperidine-3-carboxamide | A | 11.86 (s, 1 H), 7.83-7.86 (m, 2 H), 7.49-7.51 (m, 3 H), 6.73 (s, 1 H), 3.54-3.58 (m, 1 H), 3.30-3.32 (m, 1 H), 3.15-3.18 (m, 1 H), 3.02-3.08 (m, 1 H), 2.75-2.80 (m, 1 H), 1.97-1.99 (m, 1 H), 1.72-1.74 (m, 1 H), 1.56-1.60 (m, 2 H) | A | 3.494 | ES+ 297.00 |

Compounds in Table 5 were synthesised by the general methods A-C (Syn. Met.) as exemplified by Examples 1-8 using 1-(tert-butoxycarbonyl)-3-fluoropiperidine-3-carboxylic acid (CAS Number 934342-39-9).

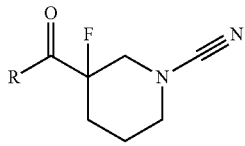

TABLE 5

| Ex | R | Name | Syn. Met. | $^1$H NMR: (400 MHz, DMSO-$d_6$) δ ppm | LCMS Met. | LCMS RT (min) | MS |
|---|---|---|---|---|---|---|---|
| 42 | (5-phenylthiazol-2-yl) | 1-Cyano-3-fluoro-N-(5-phenylthiazol-2-yl)piperidine-3-carboxamide | A | 12.61 (s, 1 H), 7.97 (s, 1 H), 7.63-7.65 (m, 2 H), 7.41-7.45 (m, 2 H), 7.31-7.35 (m, 1 H), 3.53-3.73 (m, 2 H), 3.34-3.43 (m, 1 H), 3.16-3.22 (m, 1 H), 2.00-2.14 (m, 2 H), 1.84-1.87 (m, 1 H), 1.67-1.70 (m, 1 H) | B | 4.064 | ES+ 331.27 |
| 43 | (1-phenyl-1H-imidazol-4-yl) | 1-Cyano-3-fluoro-N-(1-phenyl-1H-imidazol-4-yl)piperidine-3-carboxamide | A | 10.69 (s, 1 H), 8.17 (s, 1 H), 7.76 (s, 1 H), 7.62-7.65 (m, 2 H), 7.48-7.53 (m, 2 H), 7.36-7.39 (m, 1 H), 3.51-3.63 (m, 2 H), 3.34-3.43 (m, 1 H), 3.14-3.18 (m, 1 H), 2.03-2.08 (m, 2 H), 1.82-1.85 (m, 1 H), 1.66-1.68 (m, 1 H) | B | 3.341 | ES+ 314.27 |
| 44 | (4-phenylpyridin-2-yl) | 1-Cyano-3-fluoro-N-(4-phenylpyridin-2-yl)piperidine-3-carboxamide | A | 10.39 (s, 1 H), 8.45 (d, J = 5.2 Hz, 1 H), 8.29 (s, 1 H), 7.73-7.76 (m, 2 H), 7.48-7.57 (m, 4 H), 3.71-3.77 (m, 1 H), 3.53-3.65 (m, 1 H), 3.34-3.43 (m, 1 H), 3.17-3.22 (m, 1 H), 2.12-2.16 (m, 2 H), 1.99-2.05 (m, 1 H), 1.84-1.99 (m, 1 H) | B | 3.982 | ES+ 325.32 |
| 45 | (5-phenylisoxazol-3-yl) | 1-Cyano-3-fluoro-N-(5-phenylisoxazol-3-yl)piperidine-3-carboxamide | A | 11.39 (s, 1 H), 7.88-7.90 (m, 2 H), 7.52-7.54 (m, 3 H), 7.31 (s, 1 H), 3.67-3.73 (m, 1 H), 3.50-3.62 (m, 1 H), 3.36-3.43 (m, 1 H), 3.16-3.22 (m, 1 H), 2.10-2.12 (m, 1 H), 1.95-2.05 (m, 1 H), 1.83-1.90 (m, 1 H), 1.66-1.69 (m, 1 H). | B | 3.902 | ES+ 315.53 |
| 46 | (6-(3-cyanophenyl)pyrimidin-4-yl) | 1-Cyano-N-(6-(3-cyanophenyl)pyrimidin-4-yl)-3-fluoropiperidine-3-carboxamide | C | 11.11 (s, 1 H), 9.10 (d, J = 1.2 Hz, 1 H), 8.56 (d, J = 1.2 Hz, 1 H), 8.50-8.51 (m, 1 H), 8.39-8.42 (m, 1 H), 8.04-8.07 (m, 1 H), 7.79 (d, J = 8.0 Hz, 1H ), 3.73-3.76 (m, 1 H), 3.54-3.66 (m, 1 H), 3.38-3.44 (m, 1 H), 3.16-3.25 (m, 1 H), 2.11-2.17 (m, 1 H), 1.99-2.05 (m, 1 H), 1.83-1.88 (m, 1 H), 1.69-1.72 (m, 1 H) | A | 3.886 | ES+ 351.04 |
| 47 | (4-(3-cyanophenyl)pyridin-2-yl) | 1-Cyano-N-(4-(3-cyanophenyl)pyridin-2-yl)-3-fluoropiperidine-3-carboxamide | B | 10.49 (s, 1 H), 8.50 (d, J = 5.2 Hz, 1 H), 8.24-8.30 (m, 2 H), 8.07-8.09 (m, 1 H), 7.96-7.98 (m, 1 H), 7.74-7.78 (m, 1 H), 7.62 (dd, J = 5.2, 1.6 Hz, 1 H), 3.70-3.77 (m, 1 H), 3.53-3.65 (m, 1 H), 3.40-3.43 (m, 1 H), 3.16-3.23 (m, 1 H), 2.12-2.16 (m, 1 H), 1.98-2.08 (m, 1 H), 1.82-1.91 (m, 1 H), 1.67-1.71 (m, 1 H). | A | 4.505 | ES+ 349.98 |
| 48 | (5-phenyl-1,3,4-thiadiazol-2-yl) | 1-Cyano-3-fluoro-N-(5-phenyl-1,3,4-thiadiazol-2-yl)piperidine-3-carboxamide | A | 13.12 (s, 1 H), 7.95-7.98 (m, 2 H), 7.54-7.56 (m, 3 H), 3.72-3.78 (m, 1 H), 3.54-3.66 (m, 1 H), 3.38-3.44 (m, 1 H), 3.18-3.23 (m, 1 H), 2.10-2.15 (m, 1 H), 1.97-2.05 (m, 1 H), 1.81-1.91 (m, 1 H), 1.68-1.71 (m, 1 H) | B | 3.748 | ES+ 332.31 |

TABLE 5-continued

| Ex | R | Name | Syn. Met. | ¹H NMR: (400 MHz, DMSO-d₆) δ ppm | LCMS Met. | LCMS RT (min) | MS |
|---|---|---|---|---|---|---|---|
| 49 | | N-(5-(1H-Pyrazol-5-yl)pyridin-2-yl)-1-cyano-3-fluoropiperidine-3-carboxamide | B | 12.99-13.38 (m, 1 H), 10.29-19.41 (m, 1 H), 8.01 (s, 1 H), 8.19-8.22 (m, 1 H), 8.14-8.16 (m, 1 H), 7.08 (s, 1 H), 6.78 (s, 1 H), 3.67-3.73 (m, 1 H), 3.50-3.62 (m, 1 H), 3.36-3.40 (m, 1 H), 3.14-3.19 (m, 1 H), 2.08-2.12 (m, 1 H), 1.96-2.03 (m, 1 H), 1.81-1.87 (m, 1 H), 1.63-1.67 (m, 1 H) | B | 3.062 | ES+ 315.40 |
| 50 | | N-(6-(1H-Pyrazol-4-yl)benzo[d]thiazol-2-yl)-1-cyano-3-fluoropiperidine-3-carboxamide | C | 12.86 (s, 2 H), 8.25 (s, 1 H), 8.11 (br s, 2 H), 7.71-7.76 (m, 2 H), 3.72-3.78 (m, 1 H), 3.55-3.67 (m, 1 H), 3.40-3.43 (m, 1 H), 3.16-3.22 (m, 1 H), 2.11-2.15 (m, 1 H), 2.01-2.04 (m, 1 H), 1.84-1.88 (m, 1 H), 1.67-1.71 (m, 1 H). | A | 2.230 | ES+ 370.93 |

Example 51 (R)-4-Cyano-N-(3-(3-(trifluoromethyl)phenyl)isoxazol-5-yl)morpholine-2-carboxamide

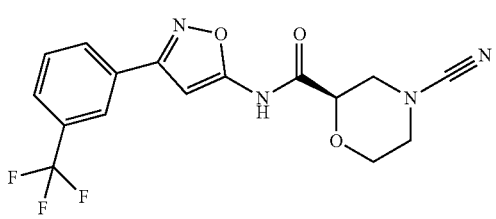 [SMILES: N#CN1CCO[C@@H](C(=O)Nc2cc(-c3cccc(C(F)(F)F)c3)no2)C1]

Separation of the racemate Example 19 by chiral SFC provided the title compound as the first eluting isomer under the following conditions: Waters PSFC 200 and UV detector, using a Chiralcel OJ-H 250×21 mm, 5 µM, column flow was 70.0 ml/min, mobile phase: (A) liquid carbon dioxide and (B) IPA, isocratic gradient of 10% B over 15 minutes. LCMS: Method A, 4.166 min, MS: ES+ 366.94; Chiral SFC: Method Y, 9.08 min; ¹H NMR (400 MHz, DMSO-d6) δ ppm: 11.93 (s, 1H), 8.20 (s, 2H), 7.87-7.89 (m, 1H), 7.73-7.77 (m, 1H), 6.99 (s, 1H), 4.39-4.42 (m, 1H), 3.93-3.96 (m, 1H), 3.69-3.75 (m, 1H), 3.56-3.60 (m, 1H), 3.22-3.32 (m, 3H).

Example 52 (R)-1-Cyano-N-(4-(3-cyanophenyl)pyridin-2-yl)-3-fluoropiperidine-3-carboxamide

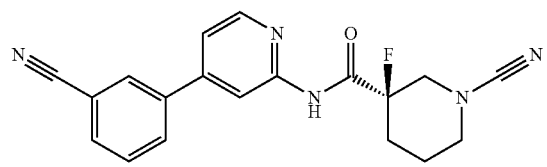 [SMILES: N#Cc1cccc(-c2ccnc(NC(=O)[C@@]3(F)CCCN(C#N)C3)c2)c1]

Separation of the racemate Example 47 by chiral SFC provided the title compound as the first eluting isomer under the following conditions: Waters PSFC 200 and UV detector, using a Chiralpak AD-H 250×21 mm, 5 µM, column flow was 80.0 ml/min, mobile phase: (A) liquid carbon dioxide and (B) IPA:MeCN (50:50), isocratic gradient of 15% B over 25 minutes. LCMS: Method A, 3.815 min, MS: ES+ 349.98; Chiral SFC: Method Z, 5.90 min; ¹H NMR (400 MHz, DMSO-d6) δ ppm: 10.49 (s, 1H), 8.51 (d, J=5.2 Hz, 1H), 8.29 (s, 1H), 8.25 (s, 1H), 8.08 (d, J=8.0 Hz, 1H), 7.98 (d, J=7.6 Hz, 1H), 7.76 (t, J=8.0 Hz, 1H), 7.62 (dd, J=5.2, 1.2 Hz, 1H), 3.70-3.77 (m, 1H), 3.53-3.65 (m, 1H), 3.36-3.43 (m, 1H), 3.17-3.23 (m, 1H), 2.12-2.16 (m, 1H), 1.98-2.09 (m, 1H), 1.82-1.91 (m, 1H), 1.68-1.71 (m, 1H).

Example 53 (R)-4-Cyano-N-(4-(3-cyanophenyl)pyridin-2-yl)morpholine-2-carboxamide Example 54 (S)-4-Cyano-N-(4-(3-cyanophenyl)pyridin-2-yl)morpholine-2-carboxamide

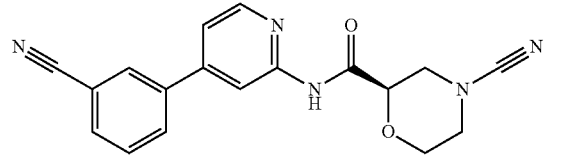

53

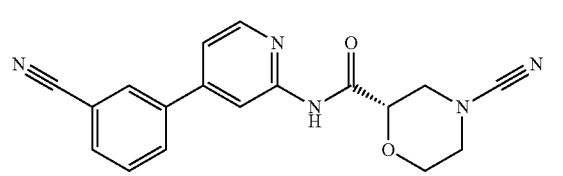

54

The title compounds were synthesised using a procedure similar to that described for Example 4. Separation of the racemate by chiral SFC provided Example 53 as the first eluting isomer and Example 54 as the second eluting isomer under the following conditions: Waters SFC 200 and UV detector, using a Chiralpak AD-H 250×21 mm, 5 µM, column flow was 80.0 ml/min, mobile phase: (A) liquid carbon dioxide and (B) IPA:MeCN (50:50), isocratic gradient of 25% B over 18 minutes. Example 53 LCMS: Method B, 3.700 min, MS: ES+ 334.58; Chiral SFC: Method X, 2.09 min; ¹H NMR (400 MHz, DMSO-d6) δ ppm: 10.20 (s, 1H), 8.46 (d, J=5.2 Hz, 1H), 8.34 (s, 1H), 8.23 (s, 1H), 8.06 (d, J=8.0 Hz, 1H), 7.97 (d, J=6.4 Hz, 1H), 7.75 (t, J=8.0 Hz, 1H), 7.57 (dd, J=5.2, 1.6 Hz, 1H), 4.39-4.42 (m, 1H), 3.97-4.00 (m, 1H), 3.69-3.75 (m, 1H), 3.56-3.60 (m, 1H), 3.22-3.32 (m, 3H). Example 54 LCMS: Method B, 3.707 min, MS: ES+ 334.53; Chiral SFC: Method X, 3.46 min; ¹H NMR (400 MHz, DMSO-d6) δ ppm: 10.20 (s, 1H), 8.46 (d, J=5.2 Hz, 1H), 8.34 (s, 1H), 8.23 (s, 1H), 8.06 (d, J=8.0 Hz, 1H), 7.97 (d, J=6.4 Hz, 1H), 7.75 (t, J=8.0 Hz, 1H), 7.57 (dd, J=5.2, 1.6 Hz, 1H), 4.39-4.42 (m, 1H), 3.97-4.00 (m, 1H), 3.69-3.75 (m, 1H), 3.56-3.60 (m, 1H), 3.22-3.32 (m, 3H).

Example 55 (R)-1-Cyano-N-(5-phenylthiazol-2-yl)piperidine-3-carboxamide

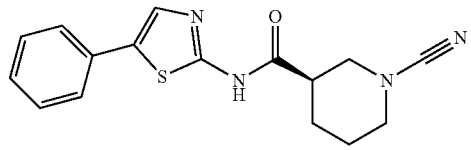 [SMILES: N#CN1CCC[C@@H](C(=O)Nc2ncc(-c3ccccc3)s2)C1]

The title compound was synthesised using a procedure similar to that described for Example 1. LCMS: Method B, 3.919 min, MS: ES+ 313.18; ¹H NMR (400 MHz, DMSO-d6) δ ppm: 12.31 (s, 1H), 7.89 (s, 1H), 7.60-7.62 (m, 2H), 7.40-7.44 (m, 2H), 7.29-7.32 (m, 1H), 3.54-3.59 (m, 1H), 3.30-3.33 (m, 1H), 3.14-3.20 (m, 1H), 3.03-3.08 (m, 1H), 2.82-2.88 (m, 1H), 1.96-1.99 (m, 1H), 1.72-1.74 (m, 1H), 1.54-1.62 (m, 2H).

Example 56 (S)-1-Cyano-N-(5-phenylthiazol-2-yl)piperidine-3-carboxamide

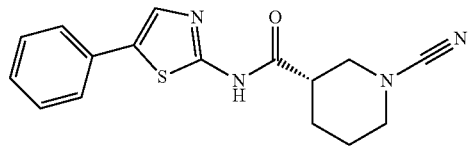 [SMILES: N#CN1CCC[C@H](C(=O)Nc2ncc(-c3ccccc3)s2)C1]

The title compound was synthesised using a procedure similar to that described for Example 1. LCMS: Method A, 3.626 min, MS: ES+ 312.90; ¹H NMR (400 MHz, DMSO-d6) δ ppm: 12.31 (s, 1H), 7.89 (s, 1H), 7.60-7.62 (m, 2H), 7.40-7.44 (m, 2H), 7.29-7.32 (m, 1H), 3.54-3.59 (m, 1H), 3.30-3.33 (m, 1H), 3.14-3.20 (m, 1H), 3.03-3.08 (m, 1H), 2.82-2.88 (m, 1H), 1.96-1.99 (m, 1H), 1.72-1.74 (m, 1H), 1.54-1.62 (m, 2H).

Example 57 (S)-1-Cyano-N-(4-(3-cyanophenyl)pyridin-2-yl)piperidine-3-carboxamide

The title compound was synthesised using a procedure similar to that described for Example 4. LCMS: Method A, 4.347 min, MS: ES+ 331.95; ¹H NMR (400 MHz, DMSO-d6) δ ppm: 10.77 (s, 1H), 8.38-8.43 (m, 2H), 8.20 (s, 1H), 7.94-8.05 (m, 2H), 7.74-7.64 (m, 1H), 7.51 (s, 1H), 3.51-3.54 (m, 1H), 3.30-3.32 (m, 1H), 3.10-3.16 (m, 1H), 3.02-3.06 (m, 1H), 2.82-2.88 (m, 1H), 1.97-1.99 (m, 1H), 1.72-1.74 (m, 1H), 1.52-1.62 (m, 2H).

Example 58 1-Cyano-5,5-difluoro-N-(1-phenyl-1H-imidazol-4-yl)piperidine-3-carboxamide

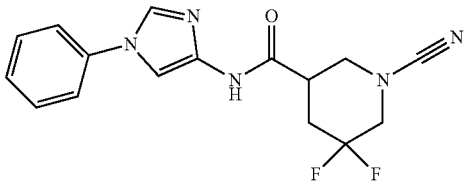 [SMILES: N#CN1CC(C(=O)Nc2cn(-c3ccccc3)cn2)CC(F)(F)C1]

The title compound was synthesised using a procedure similar to that described for Example 8, using 1-(tert-butoxycarbonyl)-5,5-difluoropiperidine-3-carboxylic acid (CAS Number 1255666-86-4). LCMS: Method B, 3.538 min, MS: ES+ 332.30; ¹H NMR (400 MHz, DMSO-d6) δ ppm: 10.85 (s, 1H), 8.13 (d, J=1.2 Hz, 1H), 7.68 (d, J=1.2 Hz, 1H), 7.61-7.63 (m, 2H), 7.49-7.53 (m, 2H), 7.34-7.37 (m, 1H), 3.69-3.75 (m, 1H), 3.57-3.65 (m, 1H), 3.39-3.53 (m, 1H), 3.14-3.29 (m, 2H), 2.36-2.39 (m, 1H), 2.10-2.25 (m, 1H).

Example 59 N-(6-(1H-Pyrazol-4-yl)benzo[d]thiazol-2-yl)-1-cyano-5,5-difluoropiperidine-3-carboxamide

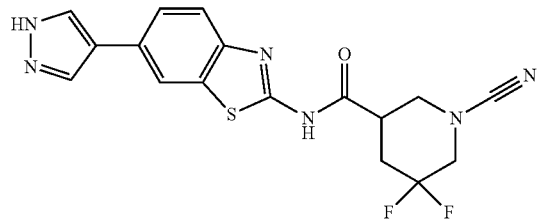 [SMILES: N#CN1CC(C(=O)Nc2nc3ccc(-c4cn[nH]c4)cc3s2)CC(F)(F)C1]

The title compound was synthesised using a procedure similar to that described for Example 5, using 1-(tert-butoxycarbonyl)-5,5-difluoropiperidine-3-carboxylic acid (CAS Number 1255666-86-4). LCMS: Method D, 5.735 min, MS: ES+ 389.15; ¹H NMR (400 MHz, DMSO-d6) δ ppm: 12.96 (s, 1H), 12.63 (s, 1H), 8.22 (s, 2H), 8.02 (br s, 1H), 7.63-7.74 (m, 2H), 3.75-3.78 (m, 2H), 3.50-3.61 (m, 1H), 3.27-3.29 (m, 2H), 2.20-2.31 (m, 2H).

Example 60 (2R,5*)-4-Cyano-N-(6-(3-cyanophenyl)pyrimidin-4-yl)-5-methylmorpholine-2-carboxamide (Single Stereoisomer, Absolute Stereochemistry of 5-Methyl Unknown)

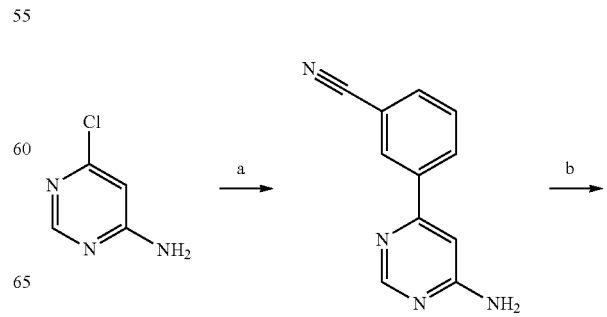

-continued

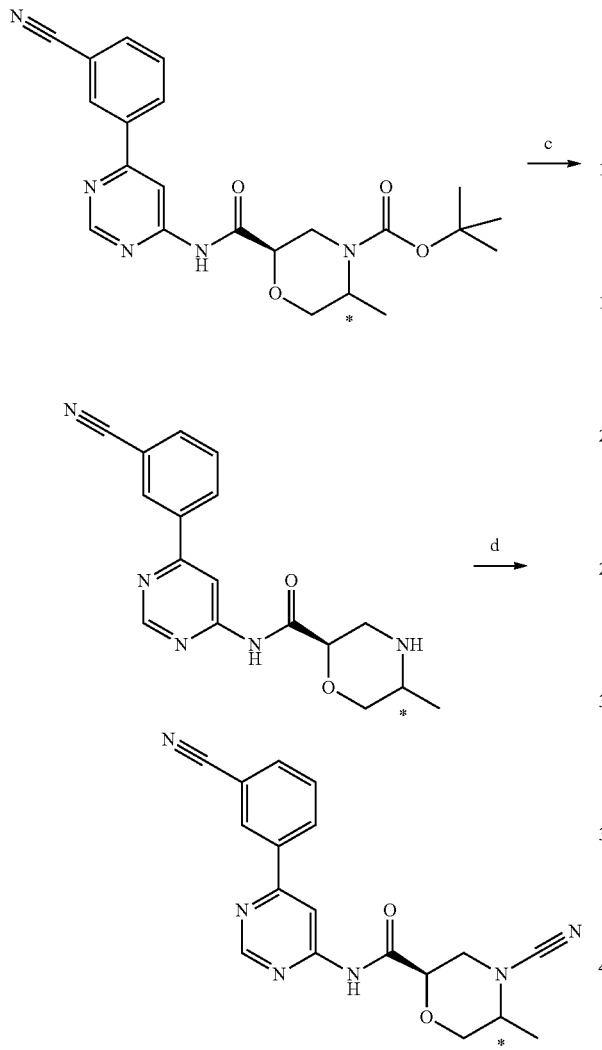

Step a. To a solution of 6-chloropyrimidin-4-amine (CAS Number 5305-59-9; 0.500 g, 3.86 mmol) and (3-cyanophenyl)boronic acid (CAS Number 150255-96-2; 0.681 g, 4.63 mmol) in 1,4-dioxane:water (4:1, 18.5 ml) was added Cs$_2$CO$_3$ (3.77 g, 11.58 mmol) at rt. The reaction mixture was degassed for 30 min before addition of PdCl$_2$(dppf) (0.141 g, 0.193 mmol). The reaction mixture was heated at 80° C. for 3 h. The resulting reaction mixture was cooled to rt and poured into water (70 ml). The mixture was extracted with EtOAc (3×50 ml). The combined organic layer was dried over Na$_2$SO$_4$, filtered and concentrated under reduced pressure. The residue was purified by column chromatography (65% EtOAc in hexane) yielding 3-(6-aminopyrimidin-4-yl) benzonitrile (0.437 g, 2.23 mmol). LCMS: Method C, 1.336 min, MS: ES+ 197.33.

Step b. To a solution of 3-(6-aminopyrimidin-4-yl)benzonitrile (0.360 g, 1.836 mmol) and (2R)-4-(tert-butoxycarbonyl)-5-methylmorpholine-2-carboxylic acid (Intermediate A, 0.500 g, 2.038 mmol) in pyridine (7 ml) at 0° C. POCl$_3$ (0.56 ml, 6.12 mmol) was added dropwise to reaction mixture at 0° C. The reaction mixture was stirred at 0° C. for 20 min and the resulting mixture was poured into water (50 ml) and basified by portion wise addition of solid NaHCO$_3$. The resulting mixture was extracted with EtOAc (3×30 ml). The combined organic layer was dried over Na$_2$SO$_4$, filtered and concentrated under reduced pressure. The residue was purified by column chromatography (24% EtOAc in hexane) yielding tert-butyl (2R)-2-((6-(3-cyanophenyl)pyrimidin-4-yl)carbamoyl)-5-methyl-morpholine-4-carboxylate stereoisomer-1 (0.365 g, 0.861 mmol); LCMS: Method C, 2.297 min, MS: ES+ 424.63 and tert-butyl (2R)-2-((6-(3-cyanophenyl)pyrimidin-4-yl)carbamoyl)-5-methylmorpholine-4-carboxylate stereoisomer-2 (0.170 g, 0.401 mmol); LCMS: Method C, 2.117 min, MS: ES+ 424.68.

Step c. To a solution of (2R)-2-((6-(3-cyanophenyl)pyrimidin-4-yl)carbamoyl)-5-methylmorpholine-4-carboxylate stereoisomer-1 (0.335 g, 0.791 mmol) was added TFA (1.68 ml) at 0° C. The reaction mixture was stirred at rt for 1 h. The resulting reaction mixture was concentrated under reduced pressure and azeotropically distilled using DCM (2×15 ml). The obtained material was dried under vacuum yielding (2R)—N-(6-(3-cyanophenyl)pyrimidin-4-yl)-5-methylmorpholine-2-carboxamide TFA salt (0.33 g, quantitative).

Step d. To a solution of (2R)—N-(6-(3-cyanophenyl)pyrimidin-4-yl)-5-methylmorpholine-2-carboxamide TFA salt (0.33 g, 0.755 mmol) in THF (15 ml) was added K$_2$CO$_3$ (0.417 g, 3.02 mmol) at 0° C. The reaction mixture was stirred at 0° C. for 5 min and then treated with cyanogen bromide (0.096 g, 0.91 mmol). The reaction mixture was warmed to rt and stirred for 30 min. The resulting mixture was poured into water (30 ml) and extracted with EtOAc (3×20 ml). The combined organic phase was dried over Na$_2$SO$_4$, filtered and concentrated under reduced pressure. The residue was purified by flash column chromatography (50% EtOAc in hexane) yielding the title compound (0.210 g, 0.602 mmol). LCMS: Method A, 3.814 min, MS: ES+ 348.98; $^1$H NMR (400 MHz, DMSO-d6) δ ppm: 10.90 (s, 1H), 9.05 (s, 1H), 8.60 (s, 1H), 8.51 (s, 1H), 8.41 (d, J=10.4 Hz, 1H), 8.05 (d, J=10.4 Hz, 1H), 7.79 (t, J=8 Hz, 1H), 4.49-4.51 (m, 1H), 3.78-3.81 (m, 1H), 3.62-3.72 (m, 2H), 3.44-3.53 (m, 2H), 1.22 (d, J=6.8 Hz, 3H).

Example 61 (R)—N-(6-(3-(1H-Pyrazol-4-yl)phenyl)pyrimidin-4-yl)-4-cyanomorpholine-2-carboxamide

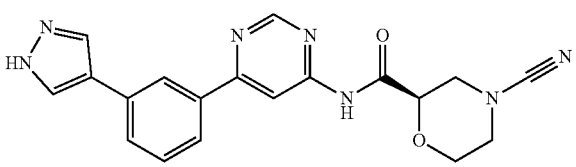 [SMILES: N#CN1CCO[C@@H](C(=O)Nc2cc(-c3cccc(-c4cn[nH]c4)c3)ncn2)C1]

The title compound was synthesised using a procedure similar to that described for Example 2, using 4-amino-6-chloropyrimidine (CAS Number 5305-59-9) and Intermediate B. LCMS: Method D, 4.790 min, MS: ES+ 376.15; $^1$H NMR (400 MHz, DMSO-d6) δ ppm: 13.01 (s, 1H), 10.69 (s, 1H), 8.99 (s, 1H), 8.50 (s, 1H), 8.28 (br s, 1H), 8.23 (s, 1H), 7.97 (br s, 1H), 7.77-7.83 (m, 2H), 7.52 (t, J=8.0 Hz, 1H), 4.39-4.75 (m, 1H), 3.95-3.98 (m, 1H), 3.66-3.71 (m, 1H), 3.57-3.60 (m, 1H), 3.20-3.29 (m, 3H).

Example 62 (R)—N-(5-(3-Chlorophenyl)pyridazin-3-yl)-4-cyanomorpholine-2-carboxamide

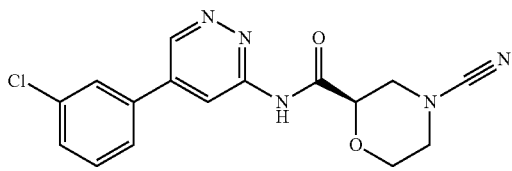 [SMILES: N#CN1CCO[C@@H](C(=O)Nc2cc(-c3cccc(Cl)c3)cnn2)C1]

The title compound was synthesised using a procedure similar to that described for Example 5, using 3-chlorophenylboronic acid (CAS Number 63503-60-6) and Intermediate C. LCMS: Method A, 2.917 min, MS: ES+ 343.92; $^1$H NMR (400 MHz, DMSO-d6) δ ppm: 9.12 (d, J=2.8 Hz, 1H), 8.49-8.50 (m, 2H), 8.12 (s, 1H), 7.97-7.99 (m, 1H), 7.46-7.52 (m, 2H), 4.34-4.38 (m, 1H), 4.17-4.20 (m, 1H), 3.94-3.98 (m, 1H), 3.85-3.89 (m, 1H), 3.34-3.37 (m, 2H), 3.18-3.23 (m, 1H).

Example 63 (R)-4-Cyano-N-(5-(3-cyanophenyl)pyridazin-3-yl)morpholine-2-carboxamide

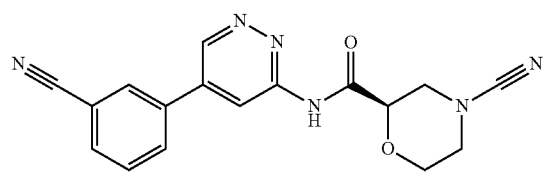 [SMILES: N#Cc1cccc(-c2cnnc(NC(=O)[C@H]3CN(C#N)CCO3)c2)c1]

The title compound was synthesised using a procedure similar to that described for Example 5, using 3-cyanophenylboronic acid (CAS Number 150255-96-2) and Intermediate C. LCMS: Method A, 3.281 min, MS: ES+ 335.01; $^1$H NMR (400 MHz, DMSO-d6) δ ppm: 10.70 (s, 1H), 9.53 (d, J=2.4 Hz, 1H), 8.55 (d, J=2.4 Hz, 1H), 8.46 (s, 1H), 8.37 (d, J=8.0 Hz, 1H), 8.03 (d, J=7.6 Hz, 1H), 7.80 (t, J=8.0 Hz, 1H), 4.45-4.48 (m, 1H), 3.99-4.03 (m, 1H), 3.77-3.82 (m, 1H), 3.59-3.63 (m, 1H), 3.24-3.32 (m, 3H).

Example 64 1-Cyano-N-(5-(3-cyanophenyl)isoxazol-3-yl)-3-fluoropiperidine-3-carboxamide

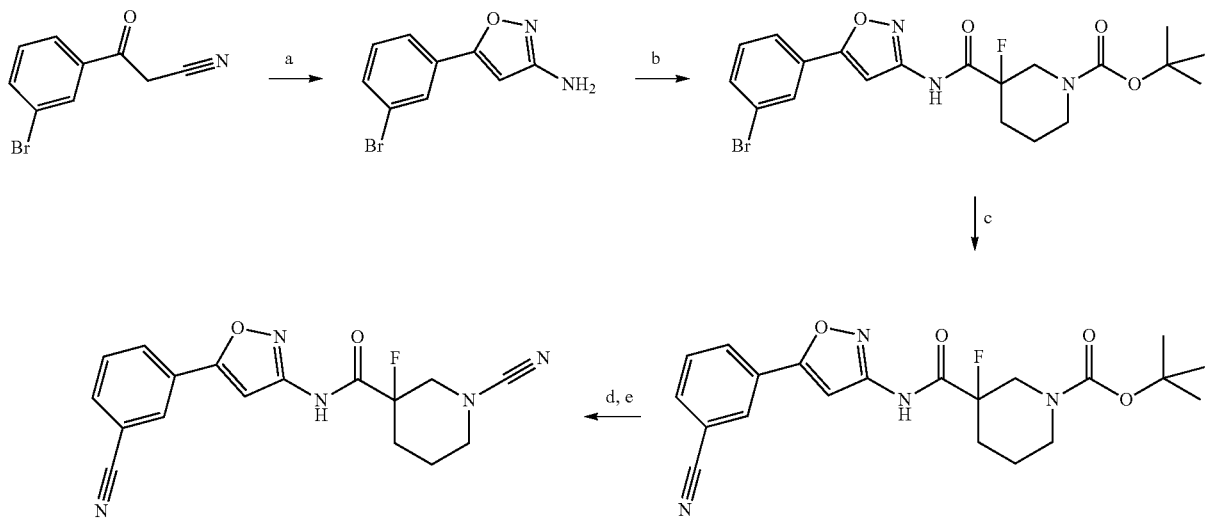

Step a. To a stirred solution of 3-(3-bromophenyl)-3-oxopropanenitrile (CAS Number 70591-86-5; 1.000 g, 4.46 mmol) in EtOH:water (1:1, 20 ml) was portion-wise added NaOH (0.196 g, 4.91 mmol) followed by NH$_2$OH.HCl (0.340 g, 4.91 mmol) at 0° C. The reaction mixture was heated at 80° C. for 16 h. The resulting mixture was concentrated under reduced pressure and the residue diluted with water (30 ml). The resulting mixture was basified with dilute NaOH solution and extracted with EtOAc (3×50 ml). The combined organic phase was dried over anhydrous Na$_2$SO$_4$, filtered and concentrated under reduced pressure. The residue was purified by flash column chromatography (26% EtOAc in hexane) yielding 5-(3-bromophenyl)isoxazol-3-amine (0.100 g, quantitative). LCMS: Method C, 1.787 min, MS: ES+ 239.20, 241.20.

Step b. To a solution of 5-(3-bromophenyl)isoxazol-3-amine (0.200 g, 0.836 mmol) and 1-(tert-butoxycarbonyl)-3-fluoropiperidine-3-carboxylic acid (CAS Number 934342-39-9; 0.206 g, 0.836 mmol) in DCM (2 ml) were dropwise added pyridine (2 ml) followed by POCl$_3$ (0.77 ml, 8.37 mmol) at 0° C. The reaction mixture was stirred for at 0° C. for 20 min and then poured into ice cold saturated NaHCO$_3$ solution (50 ml) and extracted with EtOAc (3×60 ml). The combined organic layer was washed with saturated citric acid solution (3×60 ml), dried over Na$_2$SO$_4$, filtered and concentrated under reduced pressure. The residue was purified by flash column chromatography (15% EtOAc in hexane) yielding tert-butyl 3-((5-(3-bromophenyl)isoxazol-3-yl)carbamoyl)-3-fluoropiperidine-1-carboxylate (0.230 g, 0.491 mmol). LCMS Method C: 2.572 min, MS: ES+ 468.50, 470.50.

Step c. A solution of tert-butyl 3-((5-(3-bromophenyl)isoxazol-3-yl)carbamoyl)-3-fluoropiperidine-1-carboxylate (0.205 g, 0.438 mmol) in DMF (2 ml) was degassed for 20 min before addition of $Zn(CN)_2$ (0.128 g, 1.09 mmol) and zinc dust (0.013 g, 0.22 mmol), followed by $Pd_2(dba)_3$ (0.080 g, 0.087 mmol) and dppf (0.048 g, 0.087 mmol). The reaction mixture was heated at 150° C. for 4 h. The resulting mixture was cooled to rt and filtered through celite. The filtrate was diluted with water (50 ml) and extracted with EtOAc (2×50 ml). The combined organic phase was dried over anhydrous $Na_2SO_4$, filtered and concentrated under reduced pressure. The residue was purified by column chromatography (26% EtOAc in hexane) yielding tert-butyl 3-((5-(3-cyanophenyl)isoxazol-3-yl)carbamoyl)-3-fluoropiperidine-1-carboxylate (0.085 g, 0.20 mmol). LCMS: Method C, 2.253 min, MS: ES+ 415.60.

Steps d, e. The title compound was synthesised from the intermediate above using a procedure similar to that described for Example 1, steps b, c. LCMS: Method B, 3.837 min, MS: ES+ 340.43; $^1$H NMR (400 MHz, DMSO-$d_6$) δ ppm: 11.47 (s, 1H), 8.46 (s, 1H), 8.23 (d, J=8.0 Hz, 1H), 8.23 (d, J=7.6 Hz, 1H), 7.75 (t, J=8.0 Hz, 1H), 7.54 (s, 1H), 3.68-3.74 (m, 1H), 3.51-3.63 (m, 1H), 3.39-3.43 (m, 1H), 3.18-3.23 (m, 1H), 2.10-2.13 (m, 1H), 1.99-2.05 (m, 1H), 1.84-1.87 (m, 1H), 1.67-1.70 (m, 1H).

Example 65 (R)-4-Cyano-N-(6-cyanoisoquinolin-3-yl)morpholine-2-carboxamide

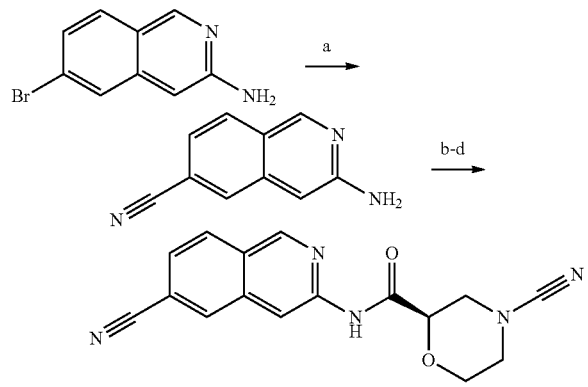

Step a. To a stirred solution of 6-bromoisoquinolin-3-amine (CAS Number 891785-28-7; 0.500 g, 2.24 mmol) in DMA (5 ml) was added $Zn(CN)_2$ (1.316 g, 11.21 mmol) at rt. The reaction mixture was degassed for 20 min before addition of $Pd(PPh_3)_4$ (0.776 g, 0.672 mmol). The reaction mixture was heated at 90° C. for 1 h. The resulting mixture was cooled to rt, diluted with water (100 ml) and extracted with EtOAc (2×100 ml). The combined organic phase was dried over anhydrous $Na_2SO_4$, filtered and concentrated under reduced pressure. The residue was purified by column chromatography (20% EtOAc in hexane) yielding 3-aminoisoquinoline-6-carbonitrile (0.640 g, quantitative). LCMS: Method C, 1.460 min, MS: ES+ 170.33.

Steps b-d. The title compound was synthesised from the intermediate above using a procedure similar to that described for Example 1. LCMS: Method A, 3.844 min, MS: ES+ 308.01; $^1$H NMR (400 MHz, DMSO-$d_6$) δ ppm: 10.35 (s, 1H), 9.33 (s, 1H), 8.66 (s, 1H), 8.55 (s, 1H), 8.27 (d, J=8.4 Hz, 1H), 7.84 (d, J=7.6 Hz, 1H), 4.42-4.45 (m, 1H), 3.98-4.01 (m, 1H), 3.70-3.75 (m, 1H), 3.59-3.62 (m, 1H), 3.24-3.32 (m, 3H).

Example 66 (2R)-4-Cyano-N-(1-(4-cyanopyridin-2-yl)pyrrolidin-3-yl)morpholine-2-carboxamide

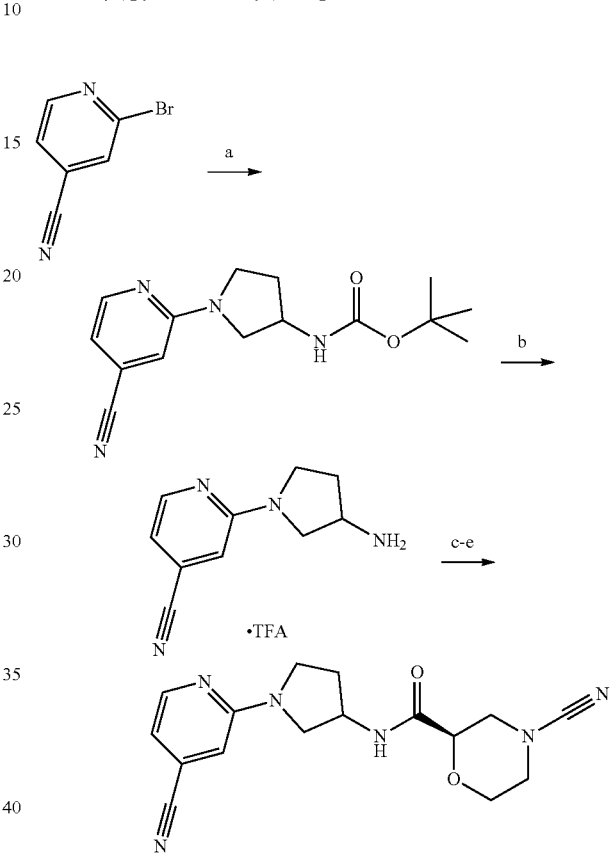

Step a. To a stirred solution of 2-bromo-4-cyanopyridine (CAS Number 10386-27-3; 0.500 g, 2.73 mmol) and tert-butyl pyrrolidin-3-ylcarbamate (CAS Number 99724-19-3; 0.509 g, 2.73 mmol) in DMF (10 ml) was added $Na_2CO_3$ (0.578 g, 5.46 mmol). The reaction mixture was stirred at rt for 16 h. The resulting mixture was diluted with water (50 ml) and extracted with EtOAc (3×50 ml). The combined organic phase was washed with brine solution (50 ml), dried over anhydrous $Na_2SO_4$, filtered and concentrated under reduced pressure. The residue was purified by column chromatography (18% EtOAc in hexane) yielding tert-butyl (1-(4-cyanopyridin-2-yl)pyrrolidin-3-yl)carbamate (0.480 g, 1.67 mmol). LCMS: Method C, 1.871 min, MS: ES+ 289.48.

Step b. To a solution of tert-butyl (1-(4-cyanopyridin-2-yl)pyrrolidin-3-yl)carbamate (0.450 g, 1.56 mmol) in DCM (10 ml) was added TFA (2.25 ml) at rt. The reaction mixture was stirred at rt for 5 h. The resulting reaction mixture was concentrated under reduced pressure. The obtained residue was azeotropically distilled using DCM (20 ml) followed by diethyl ether (25 ml). The obtained material was dried under vacuum yielding 2-(3-aminopyrrolidin-1-yl)isonicotinonitrile (0.280 g, 1.49 mmol). MS: ES+ 189.10.

Steps c-e. The title compound was synthesised from the intermediate above using a procedure similar to that described for Example 1. LCMS: Method F, 16.993, 17.578 min, MS: ES+ 327.20; $^1$H NMR (400 MHz, DMSO-d$_6$) δ ppm: 8.20-8.35 (m, 2H), 6.84-6.86 (m, 2H), 4.38-4.39 (m, 1H), 4.04-4.09 (m, 1H), 3.84-3.87 (m, 1H), 3.58-3.64 (m, 2H), 3.41-3.48 (m, 4H), 3.24-3.27 (m, 1H), 3.07-3.18 (m, 2H), 2.10-2.14 (m, 1H), 1.93-1.98 (m, 1H).

Example 67 (S)-4-Cyano-1-methyl-N-(5-phenylthiazol-2-yl)piperazine-2-carboxamide

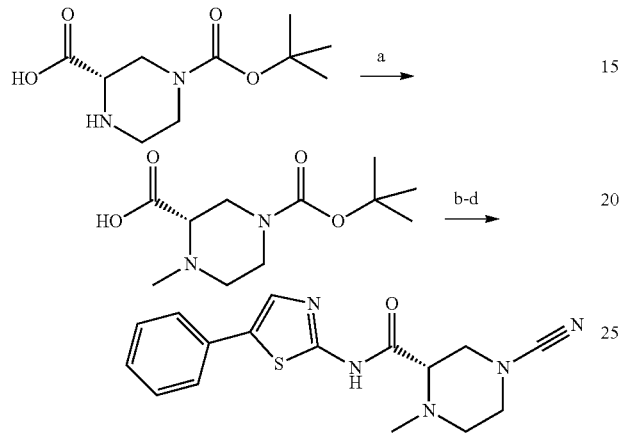

Step a. To a stirred solution of (S)-4-(tert-butoxycarbonyl)piperazine-2-carboxylic acid (CAS Number 848482-93-9; 0.540 g, 2.35 mmol) in MeOH (15 ml) was added 37% aqueous formaldehyde solution (0.2 ml) and a catalytic amount of acetic acid, followed by 10% dry Pd/C (0.100 g) under nitrogen atmosphere at rt. The reaction mixture was purged with H$_2$ gas at rt for 2 h. The resulting reaction mixture was carefully filtered through celite hyflow and the filtrate was concentrated under reduced pressure. The residue was triturated with n-pentane (5 ml) to obtain a solid material, which was dried under high vacuum to yield (S)-4-(tert-butoxycarbonyl)-1-methylpiperazine-2-carboxylic acid (0.300 g, 1.23 mmol). This material was used directly for the next step without further purification. LCMS: Method C, 1.560 min, MS: ES+ 245.33.

Steps b-d. The title compound was synthesised from the intermediate above using a procedure similar to that described for Example 1. LCMS: Method B, 3.252 min, MS: ES+ 328.48; $^1$H NMR (400 MHz, DMSO-d6) δ ppm: 12.42 (s, 1H), 7.92 (s, 1H), 7.62-7.64 (m, 2H), 7.40-7.44 (m, 2H), 7.30-7.33 (m, 1H), 3.51-3.54 (m, 1H), 3.30-3.32 (m, 1H), 3.21-3.29 (m, 3H), 2.94-2.97 (m, 1H), 2.28-2.34 (m, 1H), 2.23 (s, 3H).

Example 68 (R)-1-Cyano-N-(4-(3-cyanophenyl)pyridin-2-yl)piperidine-3-carboxamide

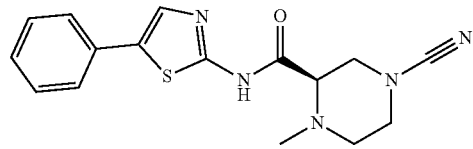 [SMILES: CN1CCN(C#N)C[C@@H]1C(=O)Nc1ncc(-c2ccccc2)s1]

The title compound was synthesised using a procedure similar to that described for Example 67, using (R)-4-(tert-butoxycarbonyl)piperazine-2-carboxylic acid (CAS Number 192330-11-3). LCMS: Method B, 3.253 min, MS: ES+ 328.48; $^1$H NMR (400 MHz, DMSO-d6) δ ppm: 12.42 (s, 1H), 7.92 (s, 1H), 7.62-7.64 (m, 2H), 7.40-7.44 (m, 2H), 7.30-7.33 (m, 1H), 3.51-3.54 (m, 1H), 3.30-3.32 (m, 1H), 3.21-3.29 (m, 3H), 2.94-2.97 (m, 1H), 2.28-2.34 (m, 1H), 2.23 (s, 3H).

Example 69 4-Cyano-1-phenyl-N-(5-phenylthiazol-2-yl)piperazine-2-carboxamide

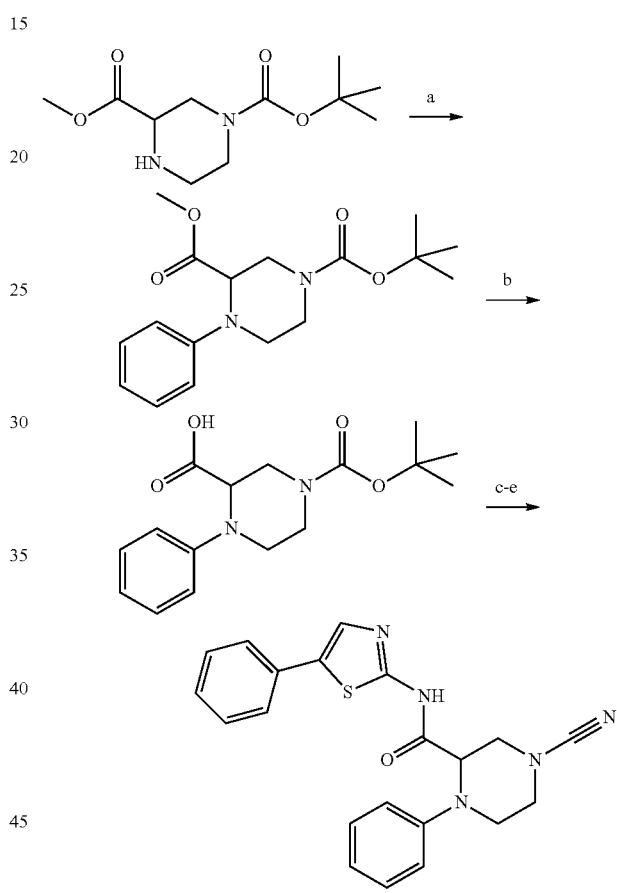

Step a. To a stirred solution of 1-(tert-butyl) 3-methyl piperazine-1,3-dicarboxylate (CAS Number 129799-08-2; 0.500 g, 2.05 mmol) in DCM (5 ml) were added phenylboronic acid (0.347 g, 3.07 mmol) and copper acetate (0.111 g, 0.614 mmol) at rt. The reaction mixture was stirred at rt for 16 h. The resulting reaction mixture was poured into water (50 ml) and extracted with EtOAc (2×25 ml). The combined organic phase was collected, dried over Na$_2$SO$_4$, filtered and concentrated under reduced pressure. The resulting residue was purified by column chromatography (10% MeOH in DCM) yielding 1-(tert-butyl) 3-methyl 4-phenylpiperazine-1,3-dicarboxylate (0.200 g, 0.625 mmol). LCMS: Method C, 2.385 min, MS: ES+ 321.53.

Step b. To a stirred solution of 1-(tert-butyl) 3-methyl 4-phenylpiperazine-1,3-dicarboxylate (0.200 g, 0.625 mmol) in THF:water (9:1, 5.5 ml) was added LiOH (0.105 g, 2.051 mmol) at rt. The reaction mixture was stirred at rt for 16 h. The resulting reaction mixture was diluted with water (5 ml) and extracted with EtOAc (2×10 ml). The aqueous layer was acidified using aqueous citric acid solution and extracted with DCM (3×10 ml). The combined organic phase was dried over $Na_2SO_4$, filtered and concentrated under reduced pressure yielding 1-(tert-butyl) 3-methyl 4-phenylpiperazine-1,3-dicarboxylate (0.08 g, 0.261 mmol). This material was used directly for the next step without further purification. LCMS: Method C, 2.137 min, MS: ES+ 307.82.

Steps c-e. The title compound was synthesised from the intermediate above using a procedure similar to that described for Example 1. LCMS: Method C, 2.234 min, MS: ES+ 390.58; $^1$H NMR (400 MHz, DMSO-d6) δ ppm: 12.42 (s, 1H), 7.89 (s, 1H), 7.58-7.60 (m, 2H), 7.38-7.42 (m, 2H), 7.21-7.31 (m, 3H), 6.91-6.93 (m, 2H), 6.78-6.82 (m, 1H), 4.74-4.76 (m, 1H), 3.92-3.96 (m, 1H), 3.64-3.75 (m, 2H), 3.55-3.58 (m, 2H), 3.34-3.37 (m, 1H).

Example 70 1-Acetyl-4-cyano-N-(5-phenylthiazol-2-yl)piperazine-2-carboxamide

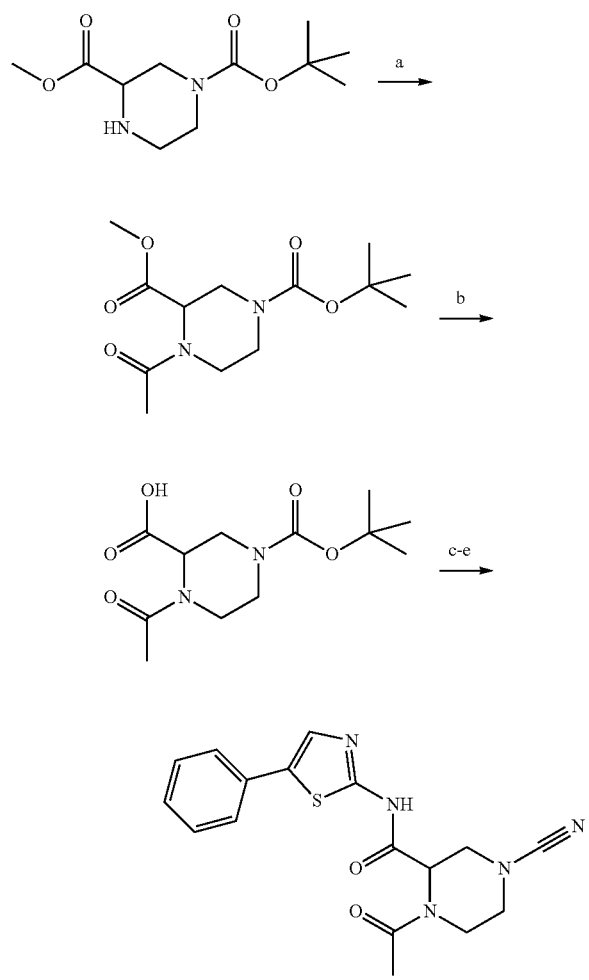

Step a. To a stirred solution of 1-(tert-butyl) 3-methyl piperazine-1,3-dicarboxylate (CAS Number 129799-08-2; 0.500 g, 2.049 mmol) in DMF (10 ml) was added TEA (0.500 ml, 3.590 mmol) at 0° C. The reaction mixture was stirred for 10 min before dropwise addition of acetyl chloride (0.200 ml, 2.67 mmol) at 0° C. The reaction mixture was stirred at rt for 16 h. The resulting mixture was poured into water (50 ml) and extracted with EtOAc (2×25 ml). The combined organic phase was dried over $Na_2SO_4$, filtered and concentrated under reduced pressure. The residue was purified by column chromatography (2% MeOH in DCM) yielding 1-(tert-butyl) 3-methyl 4-acetylpiperazine-1,3-dicarboxylate (0.400 g, 1.40 mmol). LCMS: Method C, 1.779 min, MS: ES+ 287.48.

Step b. To a stirred solution of 1-(tert-butyl) 3-methyl 4-acetylpiperazine-1,3-dicarboxylate (0.400 g, 1.40 mmol) in EtOH (2 ml) was dropwise added 10% aqueous NaOH (2 ml) at rt. The reaction mixture was stirred at rt for 16 h. The resulting reaction mixture was acidified using 2M HCl and extracted with EtOAc (2×25 ml). The combined organic phase was dried over $Na_2SO_4$, filtered and concentrated under reduced pressure yielding 1-acetyl-4-(tert-butoxycarbonyl)piperazine-2-carboxylic acid (0.300 g, 1.10 mmol). This material was used directly for the next step without further purification. LCMS: Method C, 1.616 min, MS: ES− 271.53.

Steps c-e. The title compound was synthesised from the intermediate above using a procedure similar to that described for Example 1. LCMS: Method A, 2.704 min, MS: ES+ 356.02; $^1$H NMR (400 MHz, DMSO-d6) δ ppm: 12.53 (s, 1H), 7.93 (s, 1H), 7.62-7.64 (m, 2H), 7.41-7.44 (m, 2H), 7.30-7.33 (m, 1H), 5.21-5.23 (m, 1H), 4.10-4.30 (m, 2H), 3.82-3.94 (m, 1H), 3.37-3.64 (m, 2H), 3.19-3.26 (m, 1H), 2.12 (s, 3H).

Example 71 4-Cyano-1-(methylsulfonyl)-N-(5-phenylthiazol-2-yl)piperazine-2-carboxamide

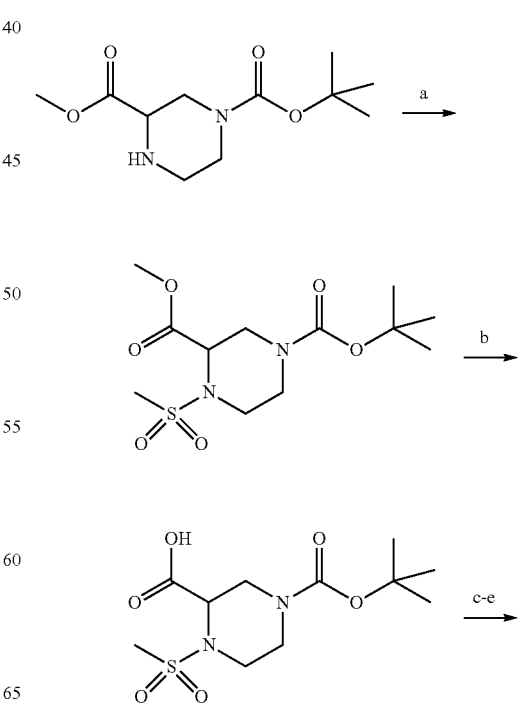

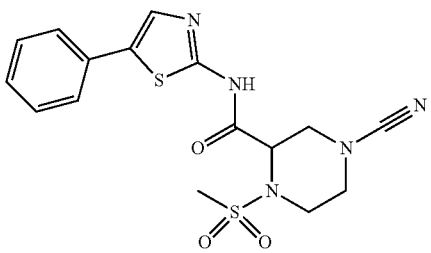

Step a. To a stirred solution of 1-(tert-butyl) 3-methyl piperazine-1,3-dicarboxylate (CAS Number 129799-08-2; 0.500 g, 2.05 mmol) in DMF (10 ml) was added TEA (0.300 ml, 2.670 mmol) at 0° C. Methanesulphonyl chloride (0.300 g, 2.67 mmol) was added dropwise to the reaction mixture at 0° C., warmed to rt and stirred for 4 h. The resulting reaction mixture was poured into water (40 ml) and extracted with EtOAc (2×30 ml). The combined organic phase was collected, dried over $Na_2SO_4$, filtered and concentrated under reduced pressure yielding 1-(tert-butyl) 3-methyl 4-(methylsulfonyl)-piperazine-1,3-dicarboxylate (0.120 g, 0.372 mmol). This material was used directly for the next step without further purification. LCMS: Method C, 1.900 min, MS: ES+ 267.30 [M-56].

Step b. To a stirred solution of 1-(tert-butyl) 3-methyl 4-(methylsulfonyl)-piperazine-1,3-dicarboxylate (0.120 g, 0.372 mmol) in EtOH (2 ml) was added dropwise 10% aqueous NaOH (1 ml) at rt. The reaction mixture was stirred at rt for 16 h. The resulting reaction mixture was concentrated under reduced pressure. The obtained residue was diluted with water (10 ml) and acidified using 2M HCl. The resulting mixture was extracted with EtOAc (2×25 ml). The combined organic phase was collected, dried over $Na_2SO_4$, filtered and concentrated under reduced pressure yielding 4-(tert-butoxycarbonyl)-1-(methylsulfonyl)piperazine-2-carboxylic acid (0.100 g, 0.324 mmol). This material was used directly for the next step without further purification. LCMS: Method C, 1.680 min, MS: ES− 307.48.

Steps c-e. The title compound was synthesised from the intermediate above using a procedure similar to that described for Example 1. LCMS: Method A, 2.663 min, MS: ES+ 391.92; $^1$H NMR (400 MHz, DMSO-d6) δ ppm: 12.64 (s, 1H), 7.95 (s, 1H), 7.63-7.65 (m, 2H), 7.41-7.44 (m, 2H), 7.30-7.34 (m, 1H), 4.71-4.72 (m, 1H), 4.10-4.30 (m, 2H), 3.94-3.98 (m, 1H), 3.49-3.76 (m, 2H), 3.19-3.25 (m, 1H), 3.06 (s, 3H).

Example 72 (R)—N-(5-(1H-Pyrazol-5-yl)pyridin-2-yl)-1-cyano-3-fluoropiperidine-3-carboxamide

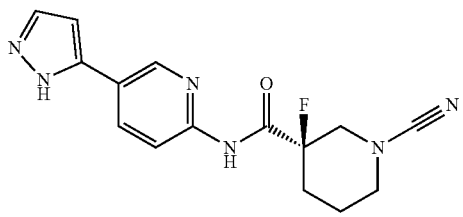 [SMILES: N#CN1CCC[C@](F)(C(=O)Nc2ccc(-c3ccn[nH]3)cn2)C1]

Separation of the racemate Example 49 by chiral SFC provided the title compound as the first eluting isomer under the following conditions: Waters SFC 200 and UV detector, using a Chiralcel OX-H 250×21 mm, 5 μM, column flow was 80.0 ml/min, mobile phase: (A) liquid carbon dioxide and (B) IPA, isocratic gradient of 25% B over 9 minutes. LCMS: Method A, 2.645 min, MS: ES+ 315.10; $^1$H NMR (400 MHz, DMSO-d6) δ ppm: 13.04 (s, 1H), 10.36 (s, 1H), 8.82-8.83 (d, J=1.6 Hz, 1H), 8.22-8.24 (d, J=7.6 Hz, 1H), 8.03-8.05 (d, J=8.4 Hz, 1H), 7.82 (br s, 1H), 6.80-6.81 (d, J=2.0 Hz, 1H), 3.71-3.77 (m, 1H), 3.53-3.65 (m, 1H), 3.40-3.43 (m, 1H), 3.17-3.23 (m, 1H), 2.11-2.14 (m, 1H), 1.98-2.08 (m, 1H), 1.81-1.90 (m, 1H), 1.66-1.70 (m, 1H)

Example 73 1-Cyano-N-(3-(3-cyanophenyl)isoxazol-5-yl)-3-fluoropiperidine-3-carboxamide

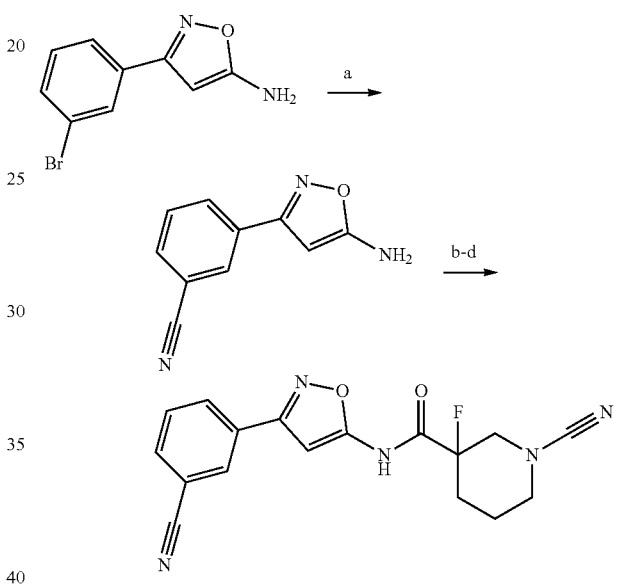

Step a. A solution of 3-(3-bromophenyl) isoxazol-5-amine (CAS Number 119162-52-6; 0.250 g, 1.05 mmol) in NMP (10 ml) was degassed for 15 min at rt. Zinc dust (0.034 g, 0.52 mmol), zinc cyanide (0.30 g, 2.62 mmol), $Pd_2(dba)_3$ (0.190 g, 0.21 mmol) and tri-tert-butylphosphonium tetrafluoroborate (CAS Number 131274-22-1; 0.060 g, 0.21 mmol) were added sequentially to the reaction mixture. The reaction mixture was heated under microwave irradiation at 160° C. for 4 h. The resulting mixture was poured into water (70 ml) and extracted with EtOAc (2×50 ml). The collected organic extracts were washed with brine (50 ml), dried over anhydrous sodium sulfate and concentrated under reduced pressure to afford crude mass, which was purified by column chromatography (compound eluted at 30% EtOAc in n-hexane) to yielding 3-(5-aminoisoxazol-3-yl)benzonitrile (0.150 g, 0.81 mmol). LCMS: Method C, 1.770 min, MS: ES+ 186.1

Steps b-d. The title compound was synthesised from the intermediate above using a procedure similar to that described for Example 60, steps b-d. LCMS: Method C, 2.663 min, MS: ES− 338.6; $^1$H NMR (400 MHz, DMSO-d6) δ ppm: 12.21 (s, 1H), 8.39 (s, 1H), 8.22-8.24 (d, J=8.0 Hz, 1H), 7.98-8.00 (d, J=8.0 Hz, 1H), 7.73 (t, J=8.0 Hz, 1H), 7.034 (s, 1H), 3.71-3.77 (m, 1H), 3.51-3.63 (m, 1H), 3.40-3.43 (m, 1H), 3.19-3.24 (m, 1H), 1.96-2.13 (m, 2H), 1.84-1.90 (m, 1H), 1.67-1.71 (m, 1H).

Example 74 (R)—N-(5-(3-Chlorophenyl)isoxazol-3-yl)-1-cyano-3-fluoropiperidine-3-carboxamide

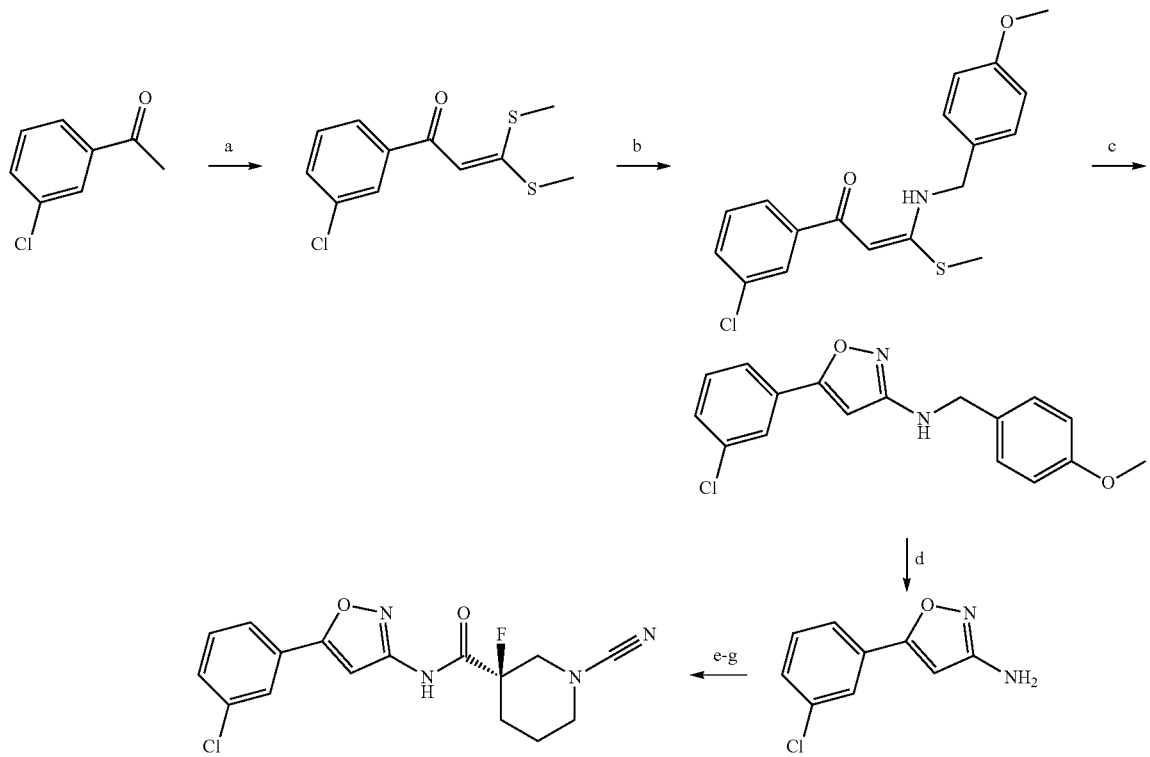

Step a. To a stirred solution of 3-chloroacetophenone (CAS Number 99-02-5; 1.00 g, 6.47 mmol) in toluene (10 ml) was added sodium tert-butoxide (2.40 g, 25.0 mmol) at 0° C. After stirring for 30 min carbon disulphide (0.7 ml, 11.6 mmol) was added dropwise into the reaction mixture. Stirring was further continued for 1 h at 0° C. followed by the addition of MeOH (15 ml) and methyl iodide (1.2 ml, 19.3 mmol). The resulting mixture was heated at 70° C. for 30 min. The solvents were distilled off under reduced pressure, and the residue partitioned between water (60 ml) and EtOAc (3×20 ml). Combined organic extracts were dried over anhydrous sodium sulfate and concentrated under reduced pressure. The crude product was purified by flash column chromatography (compound eluted at 15% EtOAc in n-hexane) to give 1-(3-chlorophenyl)-3,3-bis(methylthio)prop-2-en-1-one (1.05 g, 3.86 mmol). $^1$H NMR (400 MHz, CDCl$_3$) δ ppm 7.88-7.88 (m, 1H), 7.82-7.79 (m, 1H), 7.50-7.47 (m, 1H), 7.42-7.38 (m, 1H), 6.70 (s, 1H), 2.60-2.35 (m, 6H).

Step b. To a stirred solution of 1-(3-chlorophenyl)-3,3-bis(methylthio)prop-2-en-1-one (1.00 g, 3.88 mmol) in EtOH (25 ml) was added 4-methoxybenzylamine (1.06 g, 7.75 mmol) at rt and the resulting mixture was heated to 80° C. for 24 h. The reaction mixture was concentrated under reduced pressure and the crude residue was purified by flash column chromatography (compound eluted at 12% EtOAc in n-hexane) to yield 1-(3-chlorophenyl)-3-((4-methoxybenzyl) amino)-3-(methylthio)prop-2-en-1-one (0.945 g, 2.72 mmol). LCMS: Method C, 2.522 min, MS: ES+ 348.3

Step c. To a stirred solution of 1-(3-chlorophenyl)-3-((4-methoxybenzyl)amino)-3-(methylthio)-prop-2-en-1-one (0.940 g, 2.71 mmol) in EtOH (20 ml) were added NH$_2$OH.HCl (0.752 g, 10.8 mmol), KOH (0.608 g, 10.83 mmol) and water (6 ml) at rt and the resulting mixture was heated at 90° C. for 6 h. The reaction mixture was concentrated under reduced pressure, poured into cold water (50 ml) and extracted with EtOAc (3×20 ml). The combined organic extracts were dried over anhydrous sodium sulfate and concentrated under reduced pressure. The residue was purified by flash column chromatography (compound eluted at 16% EtOAc in n-hexane) to yield 5-(3-chlorophenyl)-N-(4-methoxybenzyl)isoxazol-3-amine (0.650 g, 2.07 mmol). LCMS: Method C, 2.255 min, MS: ES+ 315.38.

Step d. A solution of 5-(3-chlorophenyl)-N-(4-methoxybenzyl)isoxazol-3-amine (0.600 g, 1.91 mmol) in TFA (6 ml) was stirred for 2 h at rt. The reaction mixture was poured into aqueous saturated NaHCO$_3$ (80 ml) and extracted with EtOAc (3×20 ml). The combined organic extracts were dried over anhydrous sodium sulfate and concentrated under reduced pressure. The resulting residue was purified by flash column chromatography (compound eluted at 20% EtOAc in n-hexane) to give 5-(3-chlorophenyl)isoxazol-3-amine (0.210 g, 1.08 mmol). LCMS: Method C, 1.738 min, MS: ES+ 195.33. $^1$H NMR (400 MHz, CDCl$_3$) δ ppm: 7.72 (s, 1H), 7.60-7.63 (m, 1H), 7.38-7.44 (m, 2H), 6.13 (s, 1H), 4.05 (brs, 2H).

Steps e-g. The title compound was synthesised from the intermediate above using a procedure similar to that described for Example 60, steps b-d. Separation of the racemate by chiral SFC provided the title compound as the first eluting isomer under the following conditions: Waters SFC 200 and UV detector, using a Chiralcel OX-H 250×21 mm, 5 µM, column flow was 75.0 ml/min, mobile phase: (A) liquid carbon dioxide and (B) IPA, isocratic gradient of 25% B over 11 minutes. LCMS: Method B, 4.216 min, MS: ES+ 349.5; ¹H NMR (400 MHz, DMSO-d6) δ ppm: 11.43 (s, 1H), 8.01 (br s, 1H), 7.87-7.89 (m, 1H), 7.55-7.60 (m, 2H), 7.46 (s, 1H), 3.67-3.73 (m, 1H), 3.50-3.62 (m, 1H), 3.37-3.43 (m, 1H), 3.17-3.23 (m, 1H), 1.98-2.12 (m, 2H), 1.84-1.90 (m, 1H), 1.66-1.70 (m, 1H).

Example 75 (R)-1-cyano-3-fluoro-N-(5-(3-(trifluoromethyl)phenyl)isoxazol-3-yl)piperidine-3-carboxamide

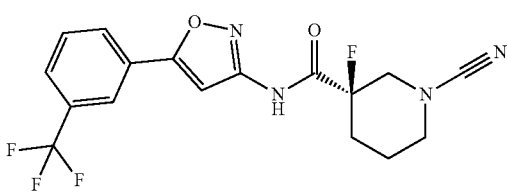 [SMILES: N#CN1CCC[C@](F)(C(=O)Nc2cc(-c3cccc(C(F)(F)F)c3)on2)C1]

The title compound was synthesised using a procedure similar to that described for Example 74, using 1-(3-(trifluoromethyl)phenyl)ethan-1-one (CAS Number 349-76-8). LCMS: Method C, 2.151 min, MS: ES– 381.5; ¹H NMR (400 MHz, DMSO-d6) δ ppm: 11.47 (br s, 1H), 8.26 (s, 1H), 8.21-8.23 (d, J=8.0 Hz, 1H), 7.88-7.90 (d, J=7.6 Hz, 1H), 7.78 (t, J=8.0 Hz, 1H), 7.58 (s, 1H), 3.67-3.73 (m, 1H), 3.50-3.63 (m, 1H), 3.39-3.42 (m, 1H), 3.17-3.23 (m, 1H), 1.98-2.12 (m, 2H), 1.83-1.89 (m, 1H), 1.66-1.70 (m, 1H).

Example 76 (R)—N-(3-(3-Chlorophenyl)isoxazol-5-yl)-1-cyano-3-fluoropiperidine-3-carboxamide

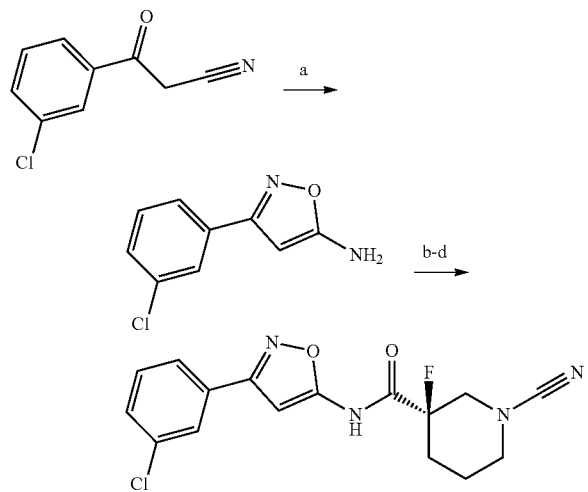

Step a. To a stirred solution of 3-(3-chlorophenyl)-3-oxopropanenitrile (CAS Number 21667-62-9; 5.00 g, 27.9 mmol) and hydroxylamine hydrochloride (2.32 g, 33.5 mmol) in water (75 ml) was added NaOH (2.23 g, 55.9 mmol) at 0° C. and the resulting mixture was heated at 100° C. for 3 h. The reaction mixture was cooled to rt, poured into water (300 ml) and extracted into EtOAc (4×200 ml). The combined organic extracts were washed with brine (50 ml), dried over anhydrous sodium sulfate and concentrated under reduced pressure. The resulting residue was purified by manual column purification (compound eluted at 28% EtOAc in n-hexane) to give 3-(3-chlorophenyl)isoxazol-5-amine (2.90 g, 14.94 mmol). LCMS: Method C, 1.803 min, MS: ES+ 195.28

Steps b-d. The title compound was synthesised from the intermediate above using a procedure similar to that described for Example 60, steps b-d. Separation of the racemate by chiral SFC provided the title compound as the first eluting isomer under the following conditions: Waters SFC 200 and UV detector, using a Chiralcel OX-H 250×21 mm, 5 µM, column flow was 75.0 ml/min, mobile phase: (A) liquid carbon dioxide and (B) IPA, isocratic gradient of 30% B over 15 minutes. LCMS: Method A, 3.962 min, MS: ES– 347; ¹H NMR (400 MHz, DMSO-d6) δ ppm: 12.17 (s, 1H), 7.94 (br s, 1H), 7.85-7.86 (d, J=7.2 Hz, 1H), 7.52-7.59 (m, 2H), 6.93 (s, 1H), 3.69-3.75 (m, 1H), 3.50-3.62 (m, 1H), 3.40-3.43 (m, 1H), 3.18-3.24 (m, 1H), 1.95-2.12 (m, 2H), 1.81-1.90 (m, 1H), 1.67-1.70 (m, 1H).

Example 77 (R)—N-(5-(1H-Pyrazol-1-yl)pyridin-2-yl)-1-cyano-3-fluoropiperidine-3-carboxamide

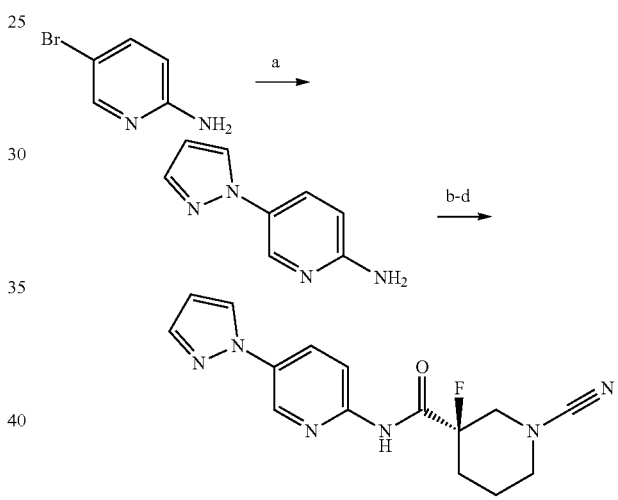

Step a. To a stirred solution of 5-bromopyridin-2-amine (CAS Number 1072-97-5; 0.50 g, 1.44 mmol) and 1H-pyrazole (0.60 g, 6.33 mmol) in DMF (5 ml) was added $K_2CO_3$ (0.60 g, 6.33 mmol) and CuI (0.05 g, 0.29 mmol) at rt and the resulting mixture was heated at 100° C. for 16 h. The reaction mixture was poured into water (70 ml) and extracted with EtOAc (2×100 ml). The combined organic extracts were washed with brine (50 ml), dried over anhydrous sodium sulfate and concentrated under reduced pressure. The residue was purified by column chromatography (compound eluted at 40% EtOAc in n-hexane) yielding 5-(1H-pyrazol-1-yl) pyridin-2-amine (0.200 g, 1.25 mmol). LCMS: Method C, 0.274 min, MS: ES+ 161.32

Steps b-d. The title compound was synthesised from the intermediate above using a procedure similar to that described for Example 60, steps b-d. Separation of the racemate by chiral SFC provided the title compound as the second eluting isomer under the following conditions: Waters SFC 200 and UV detector, using a Chiralpak AD-H 250×21 mm, 5 µM, column flow was 80.0 ml/min, mobile phase: (A) liquid carbon dioxide and (B) 0.1% DEA in IPA:MeCN (50:50), isocratic gradient of 20% B over 9 minutes. LCMS: Method A, 3.120 min, MS: ES+ 315; ¹H NMR (400 MHz, DMSO-d6) δ ppm: 10.52 (s, 1H), 8.91-8.91 (d, J=2.8 Hz, 1H), 8.57-8.58 (d, J=2.4 Hz, 1H), 8.30-8.33 (dd, J=2.8 Hz, J2=9.2 Hz, 1H), 8.11-8.13 (d, J=8.8 Hz, 1H), 7.81-7.81 (d, J=1.2 Hz, 1H), 6.61 (d, J=2.0 Hz, 1H), 3.71-3.77 (m, 1H), 3.54-3.66 (m, 1H), 3.39-3.43 (m, 1H), 3.17-3.23 (m, 1H), 2.12-2.15 (m, 1H), 2.02-2.05 (m, 1H), 1.85-1.88 (m, 1H), 1.67-1.70 (m, 1H).

Example 78 (R)-1-Cyano-N-(4-(3-cyanophenyl)oxazol-2-yl)-3-fluoropiperidine-3-carboxamide Example 79 (R)-1-Cyano-N-(1-(3-cyanophenyl)-1H-imidazol-4-yl)-3-fluoropiperidine-3-carboxamide

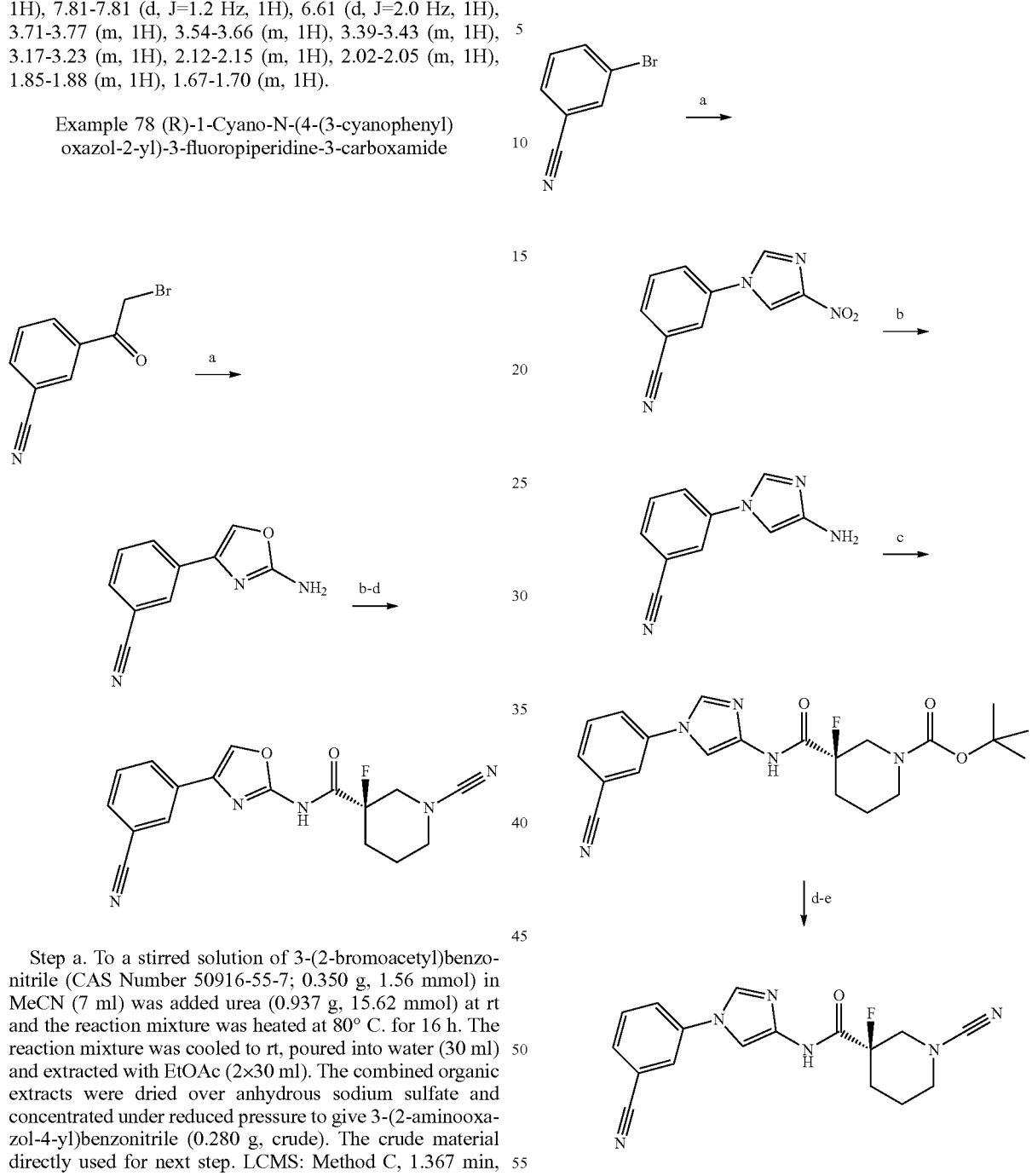

Step a. To a stirred solution of 3-(2-bromoacetyl)benzonitrile (CAS Number 50916-55-7; 0.350 g, 1.56 mmol) in MeCN (7 ml) was added urea (0.937 g, 15.62 mmol) at rt and the reaction mixture was heated at 80° C. for 16 h. The reaction mixture was cooled to rt, poured into water (30 ml) and extracted with EtOAc (2×30 ml). The combined organic extracts were dried over anhydrous sodium sulfate and concentrated under reduced pressure to give 3-(2-aminooxazol-4-yl)benzonitrile (0.280 g, crude). The crude material directly used for next step. LCMS: Method C, 1.367 min, MS: ES+ 186.18.

Steps b-d. The title compound was synthesised from the intermediate above using a procedure similar to that described for Example 60, steps b-d and using (R)-1-(tert-butoxycarbonyl)-3-fluoropiperidine-3-carboxylic acid (Intermediate D) in step b. LCMS: Method A, 2.814 min, MS: ES+ 340.0; $^1$H NMR (400 MHz, DMSO-d6) δ ppm: 8.63 (s, 1H), 8.19 (s, 1H), 8.06-8.08 (d, J=7.6 Hz, 1H), 7.80-7.82 (d, J=7.6 Hz, 1H), 7.67 (t, J=7.6 Hz, 1H), 3.70 (m, 1H), 3.49-3.68 (m, 1H), 3.39-3.42 (m, 1H), 3.20 (m, 1H), 2.08-2.11 (m, 1H), 1.91-2.07 (m, 1H), 1.80-1.89 (m, 1H), 1.66-1.70 (m, 1H).

Step a. To a stirred solution of methyl 4-nitro-1H-imidazole (CAS Number 3034-38-6; 15.0 g, 133 mmol) and 3-bromobenzonitrile (29.0 g, 159 mmol) in DMSO (150 ml) was added CuI (5.04 g, 26.54 mmol), K$_2$CO$_3$ (36.6 g, 265 mmol) and L-proline (3.0 g, 26.5 mmol) sequentially at rt. The solution was heated at 90° C. for 16 h. Another 2 batches of the reaction were carried out on the same scale by an identical method, in parallel. All 3 batches of the reaction were combined at rt and poured into ice cold water (3000 ml). The resulting mixture was filtered through Buchner funnel and the solid material was azeotroped with toluene, dried over anhydrous sodium sulfate and concentrated under reduced pressure. The resulting residue was purified by column chromatography (compound eluted at 50% EtOAc in n-hexane) yielding 3-(4-nitro-1H-imidazol-1-yl)benzonitrile (24.5 g, 114.38 mmol). LCMS: Method C, 1.453 min, MS: ES+ 215.18

Step b. Ammonium carbonate (29.2 g, 304 mmol) and zinc dust (38.9 g, 607 mmol) were sequentially added to a stirred solution of 3-(4-nitro-1H-imidazol-1-yl)benzonitrile (13.0 g, 60.7 mmol) in THF (1300 ml) and 2M HCl (300 ml) at rt and the resulting reaction mixture was heated at 50° C. for 10 min. The reaction mixture was poured into brine (1300 ml), combined with 2 other batches prepared on the same scale by an identical method and extracted together with EtOAc (3×1500 ml). The combined organic extracts were dried over anhydrous sodium sulfate and concentrated under reduced pressure to provide 3-(4-amino-1H-imidazol-1-yl)benzonitrile (23.0 g 125.0 mmol; crude). LCMS: Method C, 1.202 min, MS: ES+ 185.17

Step c. To a stirred solution of 3-(4-amino-1H-imidazol-1-yl)benzonitrile (22.0 g, 119.5 mmol) in THF (1000 mL) was added DIPEA (30.8 g, 239 mmol) followed by TBTU (57.5 g, 179.2 mmol) at 0° C. After stirring for 30 min was added was added a solution of (R)-1-(tert-butoxycarbonyl)-3-fluoro-piperidine-3-carboxylic acid (Intermediate D, 29.5 g, 119.5 mmol) in THF (200 ml) dropwise and stirred at rt for 16 h. The reaction mixture was poured into water (3000 ml) and extracted with EtOAc (2×2000 ml). The combined organic phase was washed with an aqueous solution of saturated NaHCO₃ (3×2000 ml), dried over anhydrous sodium sulfate and concentrated under reduced pressure. The resulting residue was purified by column purification (compound eluted at 50% EtOAc in n-hexane) to give tert-butyl (R)-3-((1-(3-cyanophenyl)-1H-imidazol-4-yl)carbamoyl)-3-fluoropiperidine-1-carboxylate (30.1 g, 72.9 mmol). LCMS: Method C, 1.643 min, MS: ES+ 414.37

Step d. To a stirred solution of tert-butyl (R)-3-((1-(3-cyanophenyl)-1H-imidazol-4-yl)carbamoyl)-3-fluoropiperidine-1-carboxylate (30.00 g, 72.63 mmol) in DCM (300 ml) was added TFA (200 ml) at 0° C. and stirred for 1 h. The solvent was distilled off under reduced pressure and the crude product was azeotropically distilled with DCM (4×100 ml) followed by trituration with diethyl ether (100 ml) and dried under high vacuum to give (R)—N-(1-(3-cyanophenyl)-1H-imidazol-4-yl)-3-fluoropiperidine-3-carboxamide TFA salt. (35.1 g, quantitative; crude). LCMS: Method C, 1.301 min, MS: ES+ 314.36.

Step e. To a stirred solution of (R)—N-(1-(3-cyanophenyl)-1H-imidazol-4-yl)-3-fluoropiperidine-3-carboxamide TFA salt (35.0 g, 82.0 mmol) in THF (1000 ml) was added K₂CO₃ (113.1 g, 820 mmol) at 0° C. After stirring at 0° C. for 20 min, cyanogen bromide (17.4 g, 164 mmol) was added. The reaction mixture was stirred at 0° C. to rt for 1 h. The resulting mixture was poured into water (2000 ml) and extracted with EtOAc (2×2000 ml). The combined organic extracts were dried over anhydrous sodium sulfate and concentrated under reduced pressure. The crude residue was purified by flash column chromatography (compound was eluted at 1% MeOH in DCM) yielding (R)-1-cyano-N-(1-(3-cyanophenyl)-1H-imidazol-4-yl)-3-fluoropiperidine-3-carboxamide (17.0 g, 50.3 mmol). LCMS: Method B, 3.158 min, MS: ES+ 339.43; ¹H NMR (400 MHz, DMSO-d6) δ ppm: 10.74 (s, 1H), 8.30 (d, J=6.0 Hz, 2H), 8.05 (d, J=8.0 Hz, 1H), 7.91 (s, 1H), 7.83 (d, J=7.6 Hz, 1H), 7.72 (t, J=8.0 Hz, 1H), 3.68-3.51 (m, 2H), 3.43-3.40 (m, H), 3.19 (t, J=12.0 Hz, 1H), 2.09-1.99 (m, 2H), 1.87-1.84 (m, 1H), 1.69-1.66 (m, 1H).

Example 80 1-Cyano-3-fluoro-N-(1-(3-(trifluoromethyl)phenyl)-1H-imidazol-4-yl)piperidine-3-carboxamide

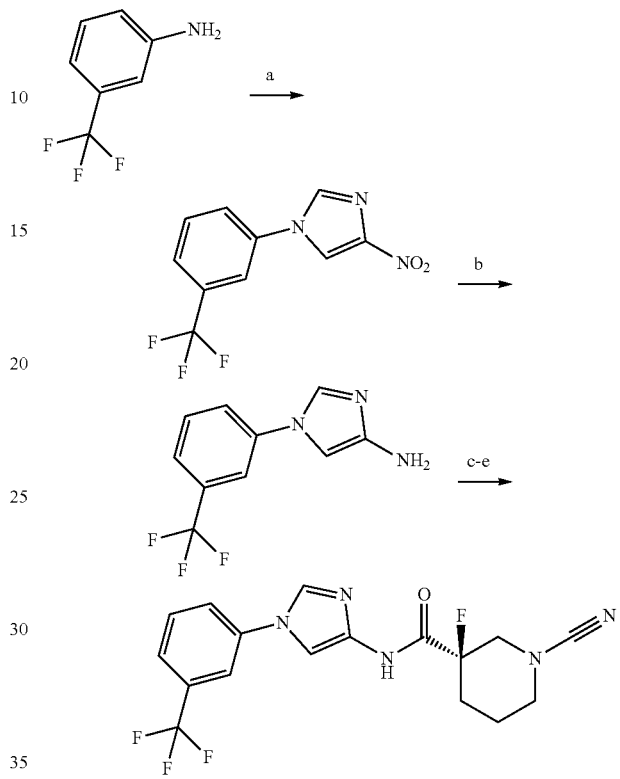

Step a. To a stirred solution of 1,4-dinitro-1H-imidazole (0.490 g, 3.10 mmol) in MeOH (8 ml) and water (2 ml) was added 3-(trifluoromethyl)aniline (0.500 g, 3.105 mmol) at rt and stirred for 18 h. The reaction mixture was taken into water (50 ml) and extracted with EtOAc (3×50 ml). The combined organic extracts were washed with brine (30 ml), dried over anhydrous sodium sulfate and concentrated under reduced pressure. The residue was purified by flash chromatography (compound eluted at 24% EtOAc in n-hexane) to yield 4-nitro-1-(3-(trifluoromethyl)phenyl)-1H-imidazole (0.600 g, 2.34 mmol). LCMS: Method C, 1.835 min, MS: ES+ 258.16, ¹H NMR (400 MHz, DMSO-d6) δ ppm: 9.18-9.17 (m, 1H), 8.63-8.62 (m, 1H), 8.29 (s, 1H), 8.17-8.15 (m, 1H), 7.89-7.82 (m, 2H).

Step b. To a stirred solution of 4-nitro-1-(3-(trifluoromethyl)phenyl)-1H-imidazole (0.250 g, 0.98 mmol) in THF:water mixture (4:1, 10 ml) was added NH₄Cl (0.522 g, 0.98 mmol) and zinc dust (0.625 g, 9.77 mmol) at rt and the resulting mixture was heated to 50° C. for 5 min. The reaction mixture was taken into brine (50 ml) and extracted with EtOAc (3×50 ml). The combined organic extracts were dried over anhydrous sodium sulfate and concentrated under reduced pressure to afford crude residue to give 1-(3-(trifluoromethyl)phenyl)-1H-imidazol-4-amine (0.230 g, crude). LCMS: Method C, 1.403 min, MS: ES+ 228.2, ¹H NMR (400 MHz, DMSO-d6) δ ppm: 8.11 (d, J=1.2 Hz, 1H). 7.97 (s, 1H), 7.91-7.89 (m, 1H), 7.73-7.69 (m, 1H), 7.65-7.64 (m, 1H), 6.85 (d, J=1.2 Hz, 1H), 4.63 (s, 2H). The crude was directly used for next step without further purification.

Steps c-e. The title compound was synthesised from the intermediate above using a procedure similar to that described for Example 79, steps c-e. LCMS: Method A, 3.706 min, MS: ES+ 382.1; $^1$H NMR (400 MHz, DMSO-d6) δ ppm: 10.71 (s, 1H), 8.33-8.34 (dd, J=1.2 Hz, 1H), 8.07 (s, 1H), 7.98-8.00 (d, J=7.6 Hz, 1H), 7.90 (s, 1H), 7.71-7.77 (m, 2H), 3.50-3.64 (m, 2H), 3.39-3.42 (m, 1H), 3.15-3.21 (m, 1H), 1.98-2.102 (m, 2H), 1.83-1.87 (m, 1H), 1.65-1.68 (m, 1H)

Example 81 1-Cyano-3-fluoro-N-(1-(3-(trifluoromethoxy)phenyl)-1H-imidazol-4-yl)piperidine-3-carboxamide

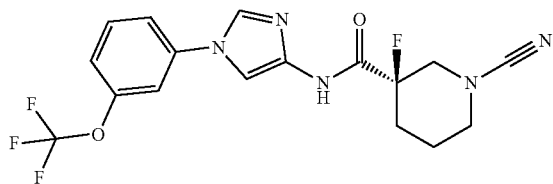 [SMILES: N#CN1CCC[C@](F)(C(=O)Nc2cn(-c3cccc(OC(F)(F)F)c3)cn2)C1]

The title compound was synthesised using a procedure similar to that described for Example 80, using 1-(3-(trifluoromethyl)phenyl)ethan-1-one (CAS Number 349-76-8). LCMS: Method A, 3.878 min, MS: ES+ 398.1; $^1$H NMR (400 MHz, DMSO-d6) δ ppm: 10.73 (s, 1H), 8.29-8.30 (d, J=1.2 Hz, 1H), 7.86-7.86 (d, J=1.2 Hz, 1H), 7.80 (br, s, 1H), 7.74-7.76 (d, J=8.4 Hz, 1H), 7.65 (t, J=8.4 Hz, 1H), 7.37-7.39 (d, J=8.0, 1H), 3.51-3.68 (m, 2H), 3.39-3.43 (m, 1H), 3.19 (m, 1H), 1.95-2.10 (m, 2H), 1.84-1.88 (m, 1H), 1.66-1.69 (m, 1H)

Example 82 (R)-1-Cyano-N-(1-(3-cyanophenyl)-1H-1,2,3-triazol-4-yl)-3-fluoropiperidine-3-carboxamide (2×50 ml). The combined organic extracts were dried over anhydrous sodium sulfate and concentrated under reduced pressure to afford crude residue to give 1-azido-3-bromobenzene (2.000 g, crude). The crude residue was carried to next step without further purification. $^1$H NMR (400 MHz, DMSO-d6) δ ppm: 7.41-7.33 (m, 3H), 7.16-7.13 (m, 1H).

Step b. A mixture of DMF.DMA (2.280 g, 19.19 mmol) and nitromethane (0.585 g, 9.59 mmol) was heated in microwave at 150° C. for 30 min. The resulting reaction mixture was cooled to rt. A solution of 1-azido-3-bromobenzene (1.890 g, 9.59 mmol) in toluene (10 ml) was added to the reaction mixture and subjected to heating at 100° C. for 22 h. The reaction mixture was brought to rt, diluted with water (50 ml) and was extracted with EtOAc (2×50 ml). The combined organic extracts were dried over anhydrous Na$_2$SO$_4$, filtered and concentrated under reduced pressure. The crude residue was purified by flash column chromatography (compound eluted at 15% EtOAc in n-hexane) to yield 1-(3-bromophenyl)-4-nitro-1H-1,2,3-triazole (0.258 g, 0.95 mmol). LCMS: Method C, 1.985 min, MS: ES+ 269.1, 271.1, $^1$H NMR (400 MHz, CDCl$_3$) δ ppm: 8.74 (s, 1H), 8.07-8.03 (m, 1H), 7.79-7.76 (m, 2H), 7.56-7.53 (m, 1H).

Step c. To a stirred suspension of 1-(3-bromophenyl)-4-nitro-1H-1,2,3-triazole (0.255 g, 0.95 mmol) in EtOH:water mixture (2:1; 10.5 ml) was added iron powder (0.319 g, 5.71 mmol) followed by AcOH (0.343 g, 5.71 mmol) at rt and the resulting reaction mixture was heated at 80° C. for 1 h. The resulting reaction mixture was cooled to rt, diluted with water (50 ml), basified with solid NaHCO$_3$ and extracted into EtOAc (2×30 ml). The combined organic extracts were dried over anhydrous sodium sulfate and concentrated under reduced pressure to afford crude residue to give 1-(3-bromophenyl)-1H-1,2,3-triazol-4-amine (0.238 g, crude). LCMS: Method C, 1.575 min, MS: ES+ 239.09, 241.09. The crude residue was carried to next step without further purification.

Step d. To a stirred solution of 1-(tert-butoxycarbonyl)-3-fluoropiperidine-3-carboxylic acid (0.280 g, 1.13 mmol)

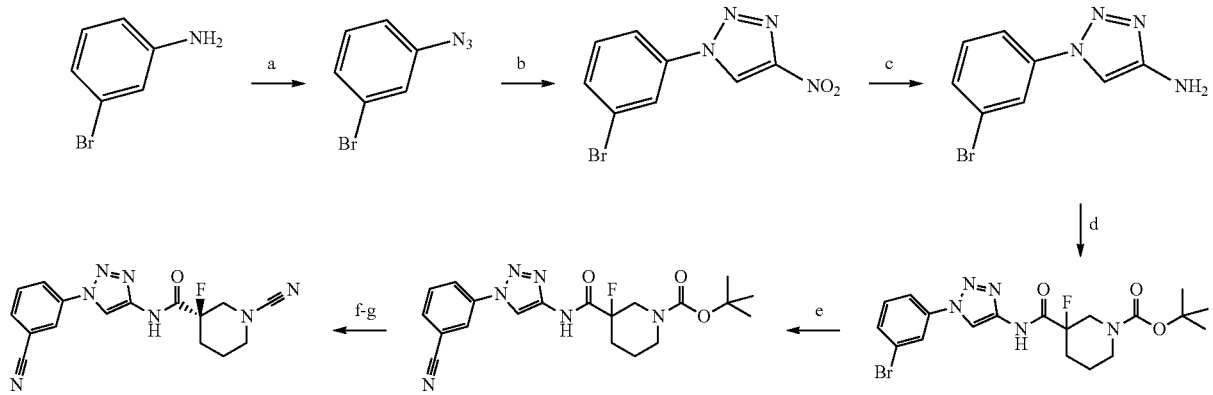

Step a. To a stirred solution of p-toluenesulphonic acid (19.90 g, 104.6 mmol) in water (15 ml) was added 3-bromoaniline (2.00 g, 11.6 mmol) followed by the portion wise addition of NaNO$_2$ (7.21 g, 104.6 mmol) at 0° C. over 30 min. The resulting reaction mixture was stirred at rt for 1 h. Sodium azide (1.20 g, 18.6 mmol) was added to the reaction mixture portion wise at 0° C. over 15 min and the resulting mixture was stirred at rt for 10 min. The reaction mixture was diluted with water (50 ml) and extracted into EtOAc in THF (5 ml) were added DIPEA (0.48 ml, 0.365 g, 2.84 mmol) and TBTU (0.456 g, 1.42 mmol) at rt. After stirring for 30 min the reaction mixture was treated with 1-(3-bromophenyl)-1H-1,2,3-triazol-4-amine (0.225 g, 0.95 mmol). Stirring was continued for an additional 5 h. The reaction mixture was diluted with an aqueous saturated NaHCO$_3$ solution (30 ml) and extracted with EtOAc (2×30 ml). The combined organic extracts were dried over anhydrous sodium sulfate and concentrated under reduced pressure. The resulting residue was purified by flash column chromatography (compound eluted at 15% EtOAc in n-hexane) yielding tert-butyl 3-((1-(3-bromophenyl)-1H-1,2,3-triazol-4-yl)carbamoyl)-3-fluoropiperidine-1-carboxylate (0.200 g, 0.43 mmol). LCMS: Method C, 2.291 min, MS: ES+ 468.4, 470.4

Step e. To a stirred solution of tert-butyl 3-((1-(3-cyanophenyl)-1H-1,2,3-triazol-4-yl)carbamoyl)-3-fluoropiperidine-1-carboxylate (0.160 g, 0.34 mmol) in DMF (3 ml) was added Zn(CN)$_2$ (0.040 g, 0.34 mmol) at rt. The resulting mixture was degassed for 15 min before addition of tetrakis (triphenylphosphine) palladium (0) (0.039 g, 0.034 mmol) and the resulting mixture was heated at 140° C. for 2 h under microwave irradiation. The resulting mixture was cooled to rt, diluted with water (30 Zo ml) and was extracted with EtOAc (2×30 ml). The combined organic phases were dried over anhydrous sodium sulfate, filtered and concentrated under reduced pressure. The crude residue was purified by flash column chromatography (compound eluted in 25% EtOAc in hexane) to give tert-butyl 3-((1-(3-cyanophenyl)-1H-1,2,3-triazol-4-yl)carbamoyl)-3-fluoropiperidine-1-carboxylate (0.095 g, 0.23 mmol). LCMS: Method C, 2.023 min, MS: ES+415.4

Steps f, g. The title compound was synthesised from the intermediate above using a procedure similar to that described for Example 1, steps b, c. Separation of the racemate by chiral HPLC provided the title compound as the first eluting isomer under the following conditions: Shimadzu LC-20AP and UV detector, using a Chiralpak IB 250×20 mm, 5 µM, column flow was 18.0 ml/min, mobile phase: (A) 0.1% DEA in n-hexane and (B) 0.1% DEA in IPA, isocratic gradient of 55% B over 28 minutes. LCMS: Method B, 3.284 min, MS: ES+ 340.3; $^1$H NMR (400 MHz, DMSO-d6) δ ppm: 11.47 (s, 1H), 9.00 (s, 1H), 8.54 (s, 1H), 8.34-8.36 (d, J=8.0 Hz, 1H), 7.97-7.99 (d, J=7.6 Hz, 1H), 7.81 (t, J=8.0 Hz, 1H), 3.66-3.73 (m, 1H), 3.53-3.65 (m, 1H), 3.39-3.44 (m, 1H), 3.18-3.24 (m, 1H), 2.10-2.13 (m, 1H), 2.01-2.04 (m, 1H), 1.86-1.89 (m, 1H), 1.68-1.71 (m, 1H).

Example 83 (R)-1-Cyano-N-(1-(3-cyanophenyl)-1H-1,2,4-triazol-3-yl)-3-fluoropiperidine-3-carboxamide

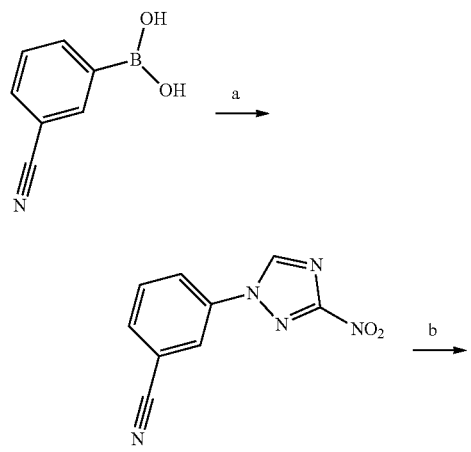

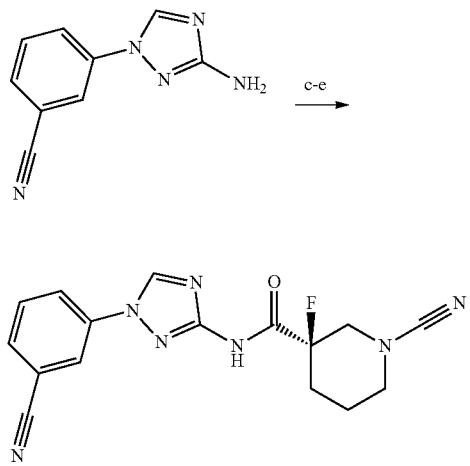

Step a. To a solution of 3-nitro-4H-1,2,4-triazole (CAS Number 24807-55-4; 1.00 g, 8.77 mmol) and (3-cyanophenyl)boronic acid (2.57 g, 17.54 mmol) in DCM (25 ml) was added copper (II) acetate (2.62 g, 13.1 mmol), pyridine (1.43 ml, 17.5 mmol) and molecular sieves (0.60 g) and stirred at rt for 16 h. The resulting reaction mixture was poured into water (250 ml) and extracted into DCM (2×200 ml). Combined organic extracts were dried over anhydrous sodium sulfate and concentrated under reduced pressure to afford crude residue, which was purified by column chromatography (compound eluted at 30% EtOAc in n-hexane) to yield 3-(3-nitro-1H-1,2,4-triazol-1-yl)benzonitrile (0.60 g, 2.79 mmol). The crude product was taken directly onto the next step.

Step b. To a stirred solution of 3-(3-nitro-1H-1,2,4-triazol-1-yl)benzonitrile (0.57 g, 2.65 mmol) in THF (10 ml) and water (5 ml) was added AcOH (1.71 ml, 3 vol) and iron powder (0.74 g, 13.2 mmol) at 0° C. The reaction mixture was stirred at rt for 2 h. The resulting mixture was filtered and the filtrate was diluted with water (100 ml), basified with solid NaHCO$_3$ and extracted into EtOAc (2×100 ml). The combined organic extracts were dried over anhydrous sodium sulfate and concentrated under reduced pressure. The residue was purified by trituration using diethyl ether (2×5 ml) to give 3-(3-amino-1H-1,2,4-triazol-1-yl)benzonitrile (0.49 g, 2.64 mmol). LCMS: Method C, 1.35 min, MS: ES+ 186.1

Steps c-e. The title compound was synthesised from the intermediate above using a procedure similar to that described for Example 5, steps b-d. Separation of the racemate by chiral SFC provided the title compound as the second eluting isomer under the following conditions: Waters SFC 200 and UV detector, using a Chiralpak AD-H 250×21 mm, 5 µM, column flow was 70.0 ml/min, mobile phase: (A) liquid carbon dioxide and (B) 0.1% DEA in IPA:MeCN (50:50), isocratic gradient of 30% B over 8 minutes. LCMS: Method A, 2.683 min, MS: ES+ 340.1; $^1$H NMR (400 MHz, DMSO-d6) δ ppm: 11.00 (s, 1H), 9.34 (s, 1H), 8.37 (s, 1H), 8.16-8.18 (dd, J1=1.2 Hz, J2=8.4 Hz, 1H), 7.90-7.92 (d, J=7.6 Hz, 1H), 7.80 (t, J=8.0 Hz, 1H), 3.51-3.71 (m, 2H), 3.41-3.44 (m, 1H), 3.17-3.23 (m, 1H), 2.09-2.12 (m, 1H), 1.96-2.06 (m, 1H), 1.85-1.91 (m, 1H), 1.67-1.70 (m, 1H).

Example 84 (R)—N-(5-(1H-Indazol-7-yl)pyridin-2-yl)-1-cyano-3-fluoropiperidine-3-carboxamide (Prepared According to General Method C)

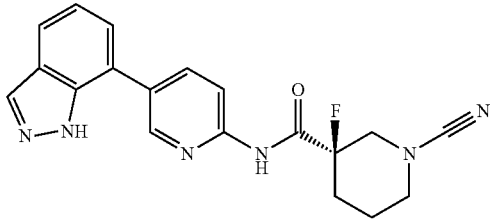

Step a. To a stirred solution of 7-bromo-1H-indazole (CAS Number 53857-58-2; 0.34 g, 1.73 mmol) and 2-aminopyridine-5-boronic acid pinacol ester (CAS Number 827614-64-2; 0.40 g, 1.82 mmol) in 1,4-dioxane:water mixture (8:2, 5 ml) was added $Cs_2CO_3$ (1.80 g, 5.52 mmol) at rt. The reaction mixture was degassed for 15 min before addition of tetrakis(triphenylphosphine) palladium (0) (0.910 g, 0.08 mmol) at rt and the resulting mixture was heated at 80° C. for 16 h. The reaction mixture was cooled to rt, diluted with water (70 ml) and was extracted with EtOAc (2×150 ml). The combined organic extracts were dried over anhydrous sodium sulfate and concentrated under reduced pressure. The resulting residue was purified by flash column chromatography (compound eluted at 2.4% MeOH in DCM) to yield 5-(1H-indazol-7-yl)pyridin-2-amine (0.30 g, 1.43 mmol). LCMS: Method C, 1.553 min, MS: ES+211.25

Steps b-d. The title compound was synthesised from the intermediate above using a procedure similar to that described for Example 5, steps b-d. Separation of the racemate by chiral SFC provided the title compound as the second eluting isomer under the following conditions: Waters SFC 200 and UV detector, using a Chiralpak IC 250×21 mm, 5 µM, column flow was 60.0 ml/min, mobile phase: (A) liquid carbon dioxide and (B) IPA:MeCN (50:50), isocratic gradient of 30% B over 12 minutes. LCMS: Method A, 3.470 min, MS: ES+ 365.1; $^1$H NMR (400 MHz, DMSO-d6) δ ppm: 13.34 (s, 1H), 10.52 (s, 1H), 8.71 (s, 1H), 8.14-8.21 (m, 3H), 7.81-7.83 (d, J=8.0 Hz, 1H), 7.46-7.47 (d, J=6.8 Hz, 1H), 7.24 (t, J=8.0 Hz, 1H), 3.73-3.79 (m, 1H), 3.56-3.68 (m, 1H), 3.41-3.44 (m, 1H), 3.18-3.24 (m, 1H), 2.14-2.17 (m, 1H), 2.01-2.07 (m, 1H), 1.85-1.92 (m, 1H), 1.68-1.71 (m, 1H).

Example 85 (R)—N-(5-(1H-Indazol-4-yl)pyridin-2-yl)-1-cyano-3-fluoropiperidine-3-carboxamide (Prepared Using a Procedure Similar to that Described for Example 84)

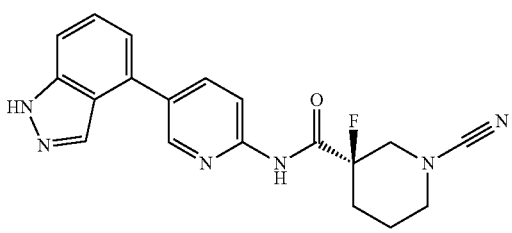 [SMILES: N#CN1CCC[C@](F)(C(=O)Nc2ccc(-c3cccc4[nH]ncc34)cn2)C1]

Step a. To a solution of 5-bromopyridin-2-amine (CAS Number 1072-97-5; 0.25 g, 1.45 mmol) in 1,4-dioxane:water (8:2; 10.0 ml) was added $Cs_2CO_3$ (1.40 g, 4.34 mmol) and (1H-indazol-4-yl)boronic acid (CAS Number 1023595-17-6; 0.23 g, 1.45 mmol) at rt. The reaction mixture was degassed for 30 min before addition of tetrakis(triphenylphosphine)palladium(0) (0.008 g, 0.07 mmol) and the reaction mixture was heated at 85° C. for 16 h. The resulting reaction mixture was poured into cold water (200 ml) and exacted with EtOAc (3×50 ml). The combined organic extracts were dried over anhydrous sodium sulfate and concentrated under reduced pressure. The resulting residue was purified by Combi-flash chromatography (compound eluted at 3.0% MeOH in DCM) to yield 5-(1H-indazol-4-yl)pyridin-2-amine (0.20 g, 0.95 mmol). LCMS: Method C, 1.32 min, MS: ES+ 211

Steps b-d. The title compound was synthesised from the intermediate above using a procedure similar to that described for Example 5, steps b-d. Separation of the racemate by chiral HPLC provided the title compound as the first eluting isomer under the following conditions: Shimadzu LC-20AP and UV detector, using a Chiralpak IB 250×20 mm, 5 µM, column flow was 17.0 ml/min, mobile phase: (A) 0.05% DEA in n-hexane and (B) 0.05% DEA in IPA, isocratic gradient of 35% B over 35 minutes. LCMS: Method A, 3.211 min, MS: ES+ 365.1; $^1$H NMR (400 MHz, DMSO-d6) δ ppm: 13.32 (s, 1H), 10.47 (s, 1H), 8.76-8.77 (d, J=2.0 Hz, 1H), 8.16-8.27 (m, 3H), 7.60-7.62 (d, J=8.0 Hz, 1H), 7.48 (t, J=7.2 Hz, 1H), 7.31-7.32 (d, J=6.8 Hz, 1H), 3.56-3.80 (m, 2H), 3.40-3.44 (m, 1H), 3.19-3.25 (m, 1H), 2.15-2.18 (m, 1H), 2.05-2.10 (m, 1H), 1.86-1.89 (m, 1H), 1.69-1.72 (m, 1H)

Example 86 (R)—N-(5-(1H-Indazol-7-yl)pyrazin-2-yl)-1-cyano-3-fluoropiperidine-3-carboxamide (Prepared Using a Procedure Similar to that Described for Example 84)

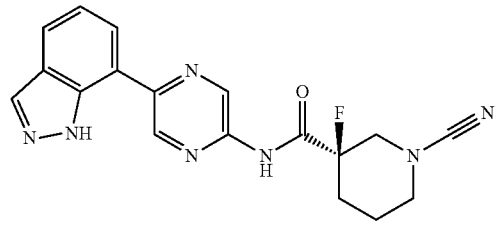 [SMILES: N#CN1CCC[C@](F)(C(=O)Nc2cnc(-c3cccc4cn[nH]c34)cn2)C1]

Step a. To a stirred suspension of 5-bromopyrazin-2-amine (CAS Number 59489-71-3; 0.100 g, 0.575 mmol) and 1H-indazol-7-ylboronic acid (CAS Number 915411-01-7; 0.102 g, 0.630 mmol) in DMF (2.4 ml) and water (0.6 ml) was added $K_2CO_3$ (0.238 g, 1.7 mmol) at rt. The reaction mixture was degassed for 30 minutes before addition of $PdCl_2$(dppf) (0.021 g, 0.028 mmol) and heated at 90° C. for 16 h. The reaction mixture was cooled to rt and quickly poured into saturated aqueous $NaHCO_3$ solution (50 ml) and extracted into EtOAc (3×20 ml). The combined organic extracts were dried over sodium sulphate and concentrated under reduced pressure. The resulting residue was purified by flash column chromatography (100% EtOAc) to yield 5-(1H-indazol-7-yl)pyrazin-2-amine (0.210 g, 0.995 mmol). LCMS: Method C, 1.437 min, MS: ES+ 212.18

Step b. To a solution of 5-(1H-indazol-7-yl)pyrazin-2-amine (0.200 g, 0.948 mmol) and (R)-1-(tert-butoxycarbonyl)-3-fluoropiperidine-3-carboxylic acid (Intermediate D, 0.257 g, 1.04 mmol) in pyridine (3 ml) was stirred at 0° C. $POCl_3$ (0.725 g, 4.738 mmol) was added dropwise to the reaction mixture at 0° C. The resulting mixture was stirred at 0° C. for 30 min. The resulting mixture was slowly poured into saturated aqueous NaHCO₃ solution (100 ml) and extracted with EtOAc (2×100 ml). The combined organic phase was dried over Na₂SO₄, filtered and concentrated under reduced pressure to yield tert-butyl (R)-3-((5-(1H-indazol-7-yl)pyrazin-2-yl)carbamoyl)-3-fluoropiperidine-1-carboxylate (0.150 g, 0.341 mmol). LCMS: Method C, 1.774 min, MS: ES+ 441.61

Steps c, d. The title compound was synthesised from the intermediate above using a procedure similar to that described for Example 5, steps c, d. LCMS: Method A, 3.523 min, MS: ES+ 366.0; ¹H NMR (400 MHz, DMSO-d6) δ ppm: 13.41 (s, 1H), 10.95 (s, 1H), 9.44 (s, 1H), 9.32 (s, 1H), 8.20-8.23 (m, 2H), 7.93-7.94 (d, J=7.6 Hz, 1H), 7.29 (m, 1H), 3.76-3.82 (m, 1H), 3.58-3.71 (m, 1H), 3.42-3.45 (m, 1H), 3.19-3.26 (m, 1H), 2.17-2.20 (m, 1H), 2.06-2.10 (m, 1H), 1.81-1.96 (m, 1H), 1.73-1.77 (m, 1H)

Example 87 (R)—N-(5-(1H-Indazol-4-yl)pyrazin-2-yl)-1-cyano-3-fluoropiperidine-3-carboxamide

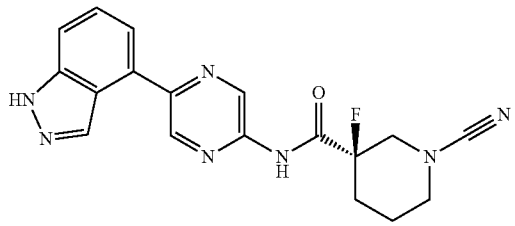 [SMILES: N#CN1CCC[C@](F)(C(=O)Nc2cnc(-c3cccc4[nH]ncc34)cn2)C1]

The title compound was synthesised using a procedure similar to that described for Example 86, using 4-(4,4,5,5-tetramethyl-1,3,2-dioxaborolan-2-yl)-1H-indazole (CAS Number 885618-33-7). LCMS: Method A, 3.187 min, MS: ES+ 366.2; ¹H NMR (400 MHz, DMSO-d6) δ ppm: 13.31 (s, 1H), 10.96 (s, 1H), 9.39 (s, 1H), 9.18 (s, 1H), 8.63 (s, 1H), 7.82-7.84 (d, J=7.2 Hz, 1H), 7.67-7.69 (d, J=8.4 Hz, 1H), 7.48-7.52 (m, 1H), 3.58-3.81 (m, 2H), 3.42-3.45 (m, 1H), 3.19-3.26 (m, 1H), 2.14-2.19 (m, 1H), 2.02-2.09 (m, 1H), 1.82-1.93 (m, 1H), 1.69-1.73 (m, 1H).

Example 88 (R)—N-(6-(1H-indazol-7-yl)pyridazin-3-yl)-1-cyano-3-fluoropiperidine-3-carboxamide (Prepared Using a Procedure Similar to that Described for Example 84)

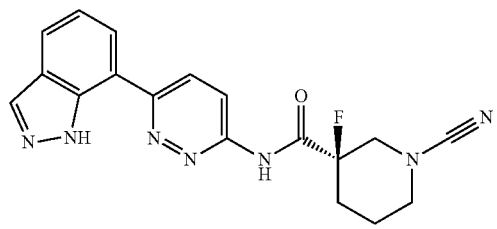

Step a. To a mixture of 6-bromopyridazin-3-amine (CAS Number 88497-27-2; 0.200 g, 1.15 mmol) and (1H-indazol-7-yl)boronic acid (CAS Number 915411-01-7; 0.277 g, 0.1.72 mmol) in 1,4-dioxane:water (1:0.5; 5 ml) was added K₂CO₃ (0.476 g, 3.45 mmol) at rt. The resulting mixture was degassed with nitrogen for 20 min before addition of PdCl₂(dppf) (0.084 g, 0.12 mmol) and the resulting reaction mixture was heated at 100° C. for 6 h. The resulting reaction mixture was cooled to rt, diluted with water (50 ml) and was extracted with EtOAc (2×50 ml). The combined organic extracts were dried over anhydrous sodium sulfate, filtered and concentrated under reduced pressure. The crude residue was purified by flash column chromatography (compound eluted in 6% MeOH in DCM) to yield 6-(1H-indazol-7-yl)pyridazin-3-amine (0.16 g, 0.76 mmol). LCMS: Method C, 1.261 min, MS: ES+ 212.17, ¹H NMR (400 MHz, CDCl₃) δ ppm 12.49 (brs, 1H), 8.21-8.22 (d, J=1.6 Hz, 1H), 8.02-8.04 (d, J=9.2 Hz, 1H), 7.90-7.92 (d, J=8.0 Hz, 1H), 7.82-7.83 (d, J=7.2 Hz, 1H), 6.99-7.01 (d, J=9.6 Hz, 1H), 4.96 (s, 2H).

Step b. To a stirred solution of 6-(1H-indazol-7-yl)pyridazin-3-amine (0.100 g, 0.47 mmol) and (R)-1-(tert-butoxycarbonyl)-3-fluoropiperidine-3-carboxylic acid (Intermediate D, 0.117 g, 0.47 mmol) in pyridine (1 ml) was added POCl₃ (0.217 g, 1.42 mmol) dropwise at 0° C. The resulting mixture was stirred at 0° C. for 15 min. The resulting mixture was diluted with water (50 ml) and extracted with EtOAc (2×50 ml). The combined organic extracts were dried over anhydrous sodium sulfate, filtered and concentrated under reduced pressure. The crude material was triturated with toluene (3×10 ml) and dried under high vacuum to give tert-butyl (R)-3-((6-(1H-indazol-7-yl)pyridazin-3-yl)carbamoyl)-3-fluoropiperidine-1-carboxylate (0.170 g, crude). The product was taken to the next step without further purification. LCMS: Method C, 1.702 min, MS: ES+ 441.56.

Steps c, d. The title compound was synthesised from the intermediate above using a procedure similar to that described for Example 5, steps c, d. LCMS: Method A, 3.356 min, MS: ES+ 366.0; ¹H NMR (400 MHz, DMSO-d6) δ ppm: 13.19 (s, 1H), 11.25 (s, 1H), 8.53-8.55 (d, J=9.6 Hz, 1H), 8.34-8.36 (d, J=9.6 Hz, 1H), 8.26 (s, 1H), 8.05-8.07 (d, J=7.2 Hz, 1H), 7.97-7.99 (d, J=8.0 Hz, 1H), 7.33 (t, J=7.6 Hz, 1H), 3.77-3.83 (m, 1H), 3.59-3.71 (m, 1H), 3.43-3.46 (m, 1H), 3.20-3.26 (m, 1H), 2.17-2.22 (m, 1H), 2.07-2.10 (m, 1H), 1.84-1.98 (m, 1H), 1.71-1.74 (m, 1H)

Example 89 (R)—N-(5-(1H-Pyrazolo[3,4-c]pyridin-7-yl)pyridin-2-yl)-1-cyano-3-fluoropiperidine-3-carboxamide

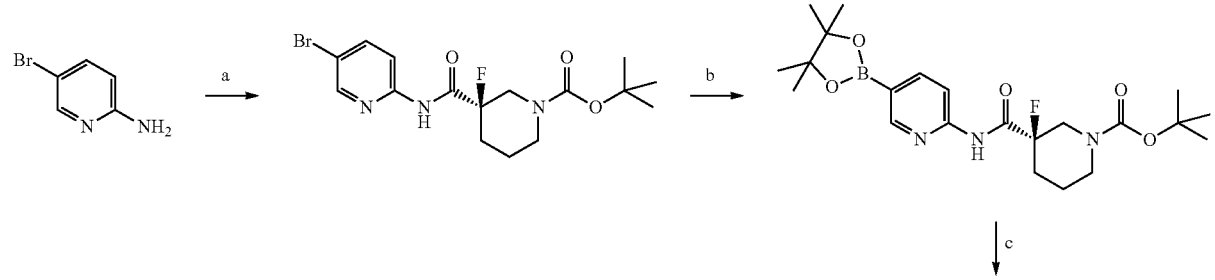

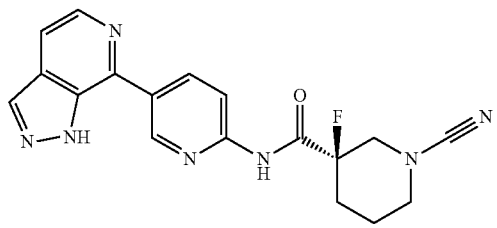 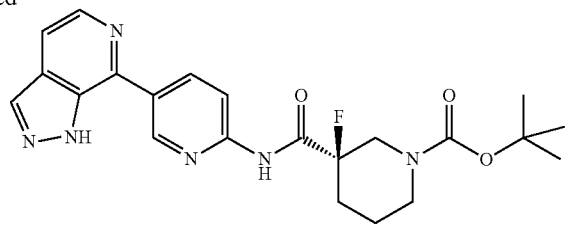

Step a. To a solution of 5-bromopyridin-2-amine (CAS Number 1072-97-5; 0.175 g, 1.01 mmol) and (R)-1-(tert-butoxycarbonyl)-3-fluoropiperidine-3-carboxylic acid (Intermediate D, 0.250 g, 1.01 mmol) in pyridine (2.5 ml) was added POCl$_3$ (0.29 ml, 3.03 mmol) dropwise at 0° C. The reaction mixture was stirred at rt for 30 min. The resulting mixture was poured into aqueous saturated NaHCO$_3$ (100 ml) and was extracted EtOAc (3×25 ml). Combined organic extracts were dried over anhydrous sodium sulfate and concentrated under reduced pressure to afford tert-butyl (R)-3-((5-bromopyridin-2-yl)carbamoyl)-3-fluoropiperidine-1-carboxylate (0.310 g, crude). LCMS: Method C, 2.34 min, MS: ES+ 402.2

Step b. To a stirred solution of (R)-3-((5-bromopyridin-2-yl)carbamoyl)-3-fluoropiperidine-1-carboxylate (0.300 g, 0.74 mmol) and bis(pinacolato)diboron (0.230 g, 0.89 mmol) in 1,4-dioxane (6 ml) was added potassium acetate (0.21 g, 2.23 mmol) at rt. The mixture was degassed for 5 min before addition of PdCl$_2$(dppf) and the mixture was heated to 90° C. for 4 h. The resulting reaction mixture was filtered and the filtrate was evaporated under reduced pressure. The residue was triturated with n-hexane (30 ml) and dried under high vacuum to yield tert-butyl (R)-3-fluoro-3-((5-(4,4,5,5-tetramethyl-1,3,2-dioxaborolan-2-yl)pyridin-2-yl)carbamoyl)piperidine-1-carboxylate (0.670 g, crude). LCMS: Method C, 1.724 min, MS: ES+ 368.42

Step c. To a stirred solution of 7-bromo-1H-pyrazolo[3,4-c]pyridine (CAS Number 957760-11-1; 0.19 g, 1.00 mmol) in 1,4-dioxane (6 ml) and water (2 ml) were added tert-butyl (R)-3-fluoro-3-((5-(4,4,5,5-tetramethyl-1,3,2-dioxaborolan-2-yl)pyridin-2-yl)carbamoyl)piperidine-1-carboxylate (0.45 g, 1.00 mmol) and Cs$_2$CO$_3$ (0.97 g, 3.00 mmol) at rt. The reaction mixture was degassed for 10 min before addition of PdCl$_2$(dppf) (0.073 g, 0.10 mmol) and the resulting solution was heated to 90° C. for 6 h. The reaction mixture was poured into water (50 ml) and extracted with EtOAc (3×25 ml). The combined organic extracts were dried over anhydrous sodium sulfate and concentrated under reduced pressure. The residue was purified by Combi-flash chromatography (compound eluted at 10% EtOAc in n-hexane) to yielding tert-butyl (R)-3-((5-(1H-pyrazolo[3,4-c]pyridin-7-yl)pyridin-2-yl)carbamoyl)-3-fluoropiperidine-1-carboxylate (0.06 g, 0.14 mmol). LCMS: Method C, 1.545 min, MS: ES+ 441.42

Steps d, e. The title compound was synthesised from the intermediate above using a procedure similar to that described for Example 1, steps b, c. LCMS: Method A, 2.80 min, MS: ES+ 266.2; $^1$H NMR (400 MHz, DMSO-d6) δ ppm: 13.97 (s, 1H), 10.60 (s, 1H), 9.07 (s, 1H), 8.51-8.53 (m, 1H), 8.37-8.38 (m, 2H), 8.21-8.23 (m, 1H), 7.82-7.83 (m, 1H), 3.57-3.81 (m, 2H), 3.42-3.41 (m, 1H), 3.08-3.25 (m, 1H), 2.15-2.18 (m, 1H), 1.86-2.10 (m, 2H), 1.69-1.72 (m, 1H).

Example 90 (R)—N-(5-(1H-pyrazolo[4,3-b]pyridin-7-yl)pyridin-2-yl)-1-cyano-3-fluoropiperidine-3-carboxamide

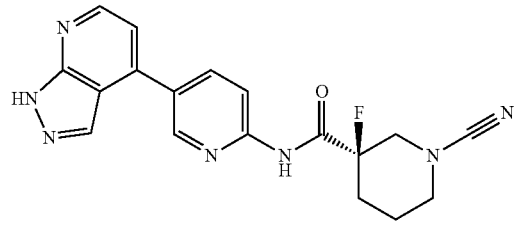 [SMILES: N#CN1CCC[C@](F)(C(=O)Nc2ccc(-c3ccnc4[nH]ncc34)cn2)C1]

The title compound was synthesised using a procedure similar to that described for Example 89, using 7-bromo-1H-pyrazolo[4,3-b]pyridine (CAS Number 1256806-33-3). LCMS: Method A, 2.780 min, MS: ES+ 366.2; $^1$H NMR (400 MHz, DMSO-d6) δ ppm: 13.73 (br, s, 1H), 10.64 (br, s, 1H), 8.87 (br, s, 1H), 8.61-8.63 (d, J=4.8 Hz, 1H), 8.33-8.44 (m, 2H), 8.20-8.22 (d, J=8.8 Hz, 1H), 7.58 (m, 1H), 3.75-3.81 (m, 1H), 3.57-3.69 (m, 1H), 3.41-3.45 (m, 1H), 3.17-3.25 (m, 1H), 2.05-2.19 (m, 2H), 1.86-1.93 (m, 1H), 1.69-1.72 (m, 1H)

Example 91 (R)—N-(6-(1H-Indazol-4-yl)pyridazin-3-yl)-1-cyano-3-fluoropiperidine-3-carboxamide

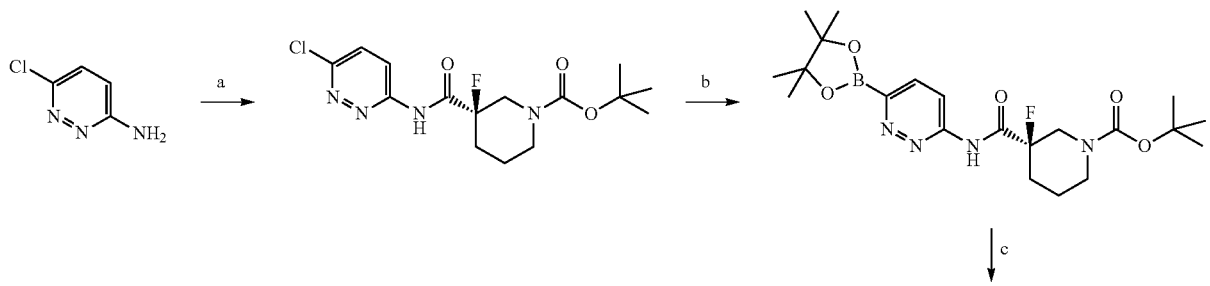

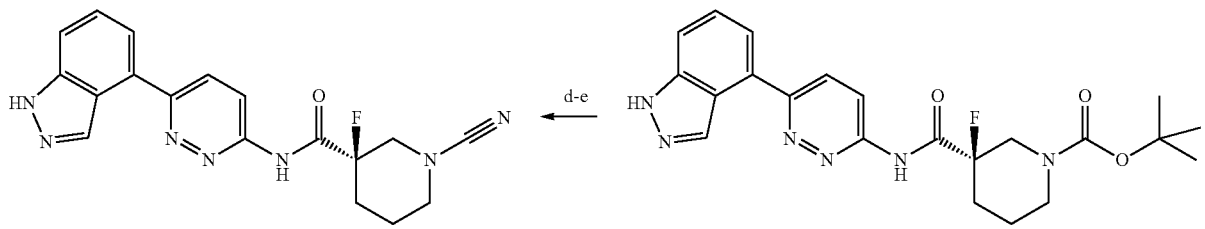

Step a. To a stirred solution of 6-chloropyridazin-3-amine (CAS Number 5469-69-2; 0.200 g, 1.55 mmol) and (R)-1-(tert-butoxycarbonyl)-3-fluoropiperidine-3-carboxylic acid (Intermediate D, 0.460 g 1.86 mmol) in DCM (8 ml) was added pyridine (0.37 ml, 4.65 mmol) at rt. The reaction mixture was cooled at 0° C. and $POCl_3$ (0.71 g, 4.65 mmol) was added dropwise. The reaction mixture was stirred at 0° C. for 30 min. The resulting mixture was poured into cold water (50 ml), basified with solid $NaHCO_3$ and extracted with DCM (3×50 ml). The combined organic extracts were dried over anhydrous sodium sulfate and concentrated under reduced pressure. The residue was purified by trituration using hexane (2 ml) and n-pentane (1 ml) and dried under reduced pressure to yield tert-butyl (R)-3-((6-chloropyridazin-3-yl) carbamoyl)-3-fluoropiperidine-1-carboxylate (0.340 g, crude). LCMS: Method C, 1.72 min, MS: ES+ 359.2

Step b. To a stirred solution of tert-butyl (R)-3-((6-chloropyridazin-3-yl)carbamoyl)-3-fluoro-piperidine-1-carboxylate (0.200 g, 0.56 mmol) in MeCN:water (6:4; 10 ml) was added potassium acetate (0.110 g 1.12 mmol) and 4-(4,4,5,5-tetramethyl-1,3,2-dioxaborolan-2-yl)-1H-indazole (CAS Number 885618-33-7; 0.270 g, 1.12 mmol) at rt. The reaction mixture was degassed for 10 min before addition of tetrakis(triphenylphosphine)palladium (0) (0.064 g, 0.05 mmol) and heated at 90° C. for 16 h. The resulting reaction mixture was poured into cold water (70 ml) and exacted with EtOAc (3×30 ml). The combined organic extracts were dried over anhydrous sodium sulfate and concentrated under reduced pressure. The residue was purified by column chromatography (compound eluted at 2% MeOH in DCM) yielding tert-butyl (S)-3-(2-(3-(4-methoxyphenyl) azetidin-1-yl)-2-oxoethyl) pyrrolidine-1-carboxylate (0.22 g, 0.5 mmol). LCMS: Method C, 1.620 min, MS: ES+441.42

Steps c-e. The title compound was synthesised from the intermediate above using a procedure similar to that described for Example 89, steps c-e. LCMS: Method A, 2.868 min, MS: ES+ 366.2; $^1$H NMR (400 MHz, DMSO-d6) δ ppm: 13.35 (s, 1H), 11.27 (s, 1H), 8.61 (s, 1H), 8.42-8.45 (m, 1H), 8.34-8.36 (m, 1H), 7.71-7.77 (m, 2H), 7.52-7.56 (m, 1H), 3.76-3.82 (m, 1H), 3.58-3.70 (m, 1H), 3.43-3.45 (m, 1H), 3.18-3.26 (m, 1H), 2.15-2.23 (m, 1H), 2.00-2.12 (m, 1H), 1.80-1.96 (m, 1H), 1.70-1.73 (m, 1H).

Example 92 (R)—N-(5-(1H-Indazol-7-yl)pyrimidin-2-yl)-1-cyano-3-fluoropiperidine-3-carboxamide

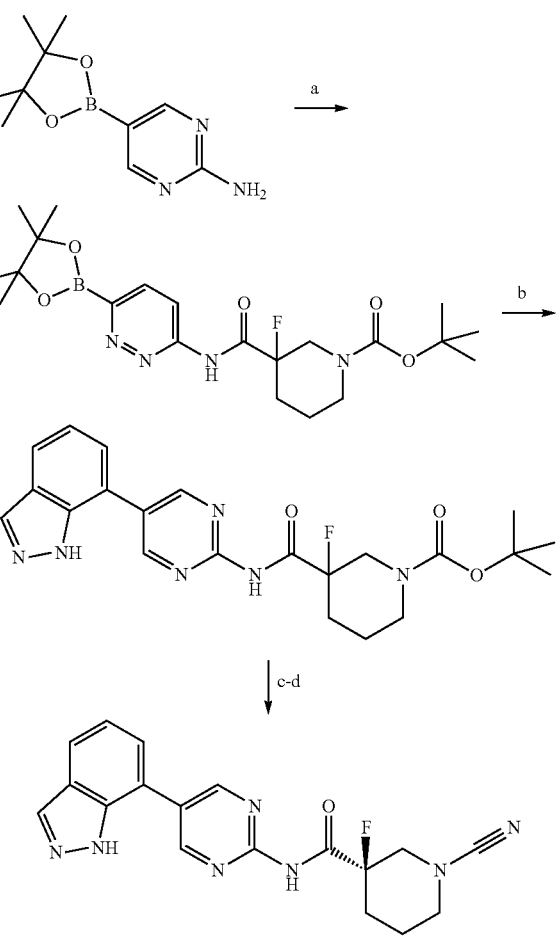

Step a. To a stirred solution of 1-(tert-butoxycarbonyl)-3-fluoropiperidine-3-carboxylic acid (0.300 g, 1.214 mmol) and 5-(4,4,5,5-tetramethyl-1,3,2-dioxaborolan-2-yl)pyrimidin-2-amine (CAS Number 402960-38-7; 0.215 g, 0.97 mmol) in pyridine (7.5 ml) was added $POCl_3$ (1.16 ml, 12.1 mmol) dropwise at 0° C. The reaction mixture was slowly warmed to rt and stirred for 1 h. The reaction mixture was poured into water (100 ml) and extracted with EtOAc (2×100 ml). The combined organic extracts were dried over anhydrous sodium sulfate and concentrated under reduced pressure. The residue was purified by flash column chromatography (compound eluted at 2% MeOH in DCM) to yield (2-(1-(tert-butoxycarbonyl)-3-fluoropiperidine-3-carboxamido)pyrimidin-5-yl)boronic acid (0.290 g, 0.79 mmol). LCMS: Method C, 1.429 min, MS: ES+ 369.28.

Step b. To a stirred solution of 7-bromo-1H-indazole (0.130 g, 0.66 mmol) and (2-(1-(tert-butoxycarbonyl)-3-fluoropiperidine-3-carboxamido)pyrimidin-5-yl)boronic acid (0.243 g, 0.66 mmol) in MeCN:water (1:1, 9 ml) was added potassium acetate (0.258 g, 2.64 mmol) at rt. The reaction mixture was degassed for 15 min before addition of tetrakis(triphenylphosphine)palladium(0) (0.076 g, 0.066 mmol) and heated at 80° C. for 16 h. The reaction mixture was cooled to rt, poured into water (100 ml) and extracted with EtOAc (2×100 ml). The combined organic extracts were washed with brine (30 ml), dried over anhydrous sodium sulfate and concentrated under reduced pressure. The resulting residue was purified by flash column chromatography (compound eluted at 90% EtOAc in n-hexane) yielding tert-butyl 3-((5-(1H-indazol-7-yl)pyrimidin-2-yl)carbamoyl)-3-fluoropiperidine-1-carboxylate (0.180 g, 0.41 mmol). LCMS: Method C, 1.594 min, MS: ES+ 441.52

Steps c, d. The title compound was synthesised from the intermediate above using a procedure similar to that described for Example 1, steps b, c. Separation of the racemate by chiral SFC provided the title compound as the first eluting isomer under the following conditions: Waters SFC 200 and UV detector, using a Chiralcel OJ-H 250×21 mm, 5 µM, column flow was 80.0 ml/min, mobile phase: (A) liquid carbon dioxide and (B) 0.1% DEA in IPA:MeCN (50:50), isocratic gradient of 20% B over 19 minutes. LCMS: Method A, 2.944 min, MS: ES+ 266.2; $^1$H NMR (400 MHz, DMSO-d6) δ ppm: 13.48 (br, s, 1H), 10.81 (br, s, 1H), 9.08 (s, 2H), 8.25 (s, 1H), 7.87-7.89 (d, J=8.0 Hz, 1H), 7.53-7.55 (d, J=6.4 Hz, 1H), 7.28 (t, J=7.6 Hz, 1H), 3.73-3.79 (m, 1H), 3.56-3.68 (m, 1H), 3.42-3.45 (m, 1H), 3.20-3.26 (m, 1H), 2.11-2.20 (m, 1H), 2.01-2.09 (m, 1H), 1.88-1.93 (m, 1H), 1.69-1.73 (m, 1H).

Biological Activity of Compounds of the Invention
Abbreviations:
TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP-40 Nonidet P-40, octylphenoxypolyethoxyethanol
BSA bovine serum albumin
PNS peripheral nervous system
BH3 Bcl-2 homology domain 3
PTEN phosphatase and tensin homologue
In Vitro USP30 Inhibition Assay USP30 biochemical kinetic assay. Reactions were performed in duplicate in black 384 well plates (small volume, Greiner 784076) in a final reaction volume of 21 µl. USP30 CD (57-517, #64-0057-050 Ubiquigent) was diluted in reaction buffer (40 mM Tris, pH 7.5, 0.005% Tween 20, 0.5 mg/ml BSA, 5 mM beta-mercaptoethanol) to the equivalent of 0, 0.005, 0.01, 0.05, 0.1 and 0.5 µl/well. Buffer was optimised for optimal temperature, pH, reducing agent, salts, time of incubation, and detergent. Reactions were initiated by the addition of 50 nM of TAMRA labelled peptide linked to ubiquitin via an iso-peptide bond as fluorescence polarisation substrate. Reactions were incubated at room temperature and read every 2 min for 120 min. Readings were performed on a Pherastar Plus (BMG Labtech). λ Excitation 540 nm; λ Emission 590 nm.

USP30 Biochemical IC50 Assay

Dilution plates were prepared at 21 times the final concentration (2100 µM for a final concentration of 100 µM) in 50% DMSO in a 96-well polypropylene V-bottom plate (Greiner #651201). A typical 8-point dilution series would be 100, 30, 10, 3, 1, 0.3, 0.1, 0.03 µM final. Reactions were performed in duplicate in black 384 well plates (small volume, Greiner 784076) in a final reaction volume of 21 µl. Either 1 µl of 50% DMSO or diluted compound was added to the plate. USP30 was diluted in reaction buffer (40 mM Tris, pH 7.5, 0.005% Tween 20, 0.5 mg/ml BSA, 5 mM beta-mercaptoethanol) to the equivalent of 0.05 µl/well and 10 µl of diluted USP30 was added to the compound. Enzyme and compound were incubated for 30 min at room temp. Reactions were initiated by the addition of 50 nM of TAMRA labelled peptide linked to ubiquitin via an iso-peptide bond as fluorescence polarisation substrate. Reactions were read immediately after addition of substrate and following a 2 h incubation at room temperature. Readings were performed on a Pherastar Plus (BMG Labtech). λ Excitation 540 nm; λ Emission 590 nm.

Activity of Exemplary Compounds in USP30 biochemical $IC_{50}$ assay
Ranges:

| Example | IC50 range |
|---|---|
| 1 | B |
| 2 | B |
| 3 | B |
| 4 | A |
| 5 | C |
| 6 | D |
| 7 | B |
| 8 | D |
| 9 | C |
| 10 | C |
| 11 | C |
| 12 | C |
| 13 | C |
| 14 | C |
| 15 | D |
| 16 | D |
| 17 | C |
| 18 | B |
| 19 | B |
| 20 | B |
| 21 | B |
| 22 | C |
| 23 | C |
| 24 | B |
| 25 | C |
| 26 | B |
| 27 | C |
| 28 | C |
| 29 | C |
| 30 | C |
| 31 | C |
| 32 | D |
| 33 | C |
| 34 | D |
| 35 | C |
| 36 | B |
| 37 | D |
| 38 | C |
| 39 | C |
| 40 | C |
| 41 | C |
| 42 | B |
| 43 | B |
| 44 | D |
| 45 | B |
| 46 | B |
| 47 | C |
| 48 | D |
| 49 | B |

-continued

| Example | IC50 range |
| --- | --- |
| 50 | C |
| 51 | B |
| 52 | B |
| 53 | A |
| 54 | C |
| 55 | D |
| 56 | C |
| 57 | C |
| 58 | C |
| 59 | C |
| 60 | D |
| 61 | C |
| 62 | B |
| 63 | D |
| 64 | B |
| 65 | C |
| 66 | C |
| 67 | D |
| 68 | C |
| 69 | D |
| 70 | D |
| 71 | C |
| 72 | B |
| 73 | B |
| 74 | A |
| 75 | A |
| 76 | A |
| 77 | B |
| 78 | A |
| 79 | B |
| 80 | B |
| 81 | B |
| 82 | B |
| 83 | B |
| 84 | A |
| 85 | A |
| 86 | A |
| 87 | A |
| 88 | A |
| 89 | A |
| 90 | B |
| 91 | A |
| 92 | A |

A < 0.1 µM;
0.1 < B < 1 µM;
1 < C < 10 µM.

The invention claimed is:
1. A compound of formula (I):

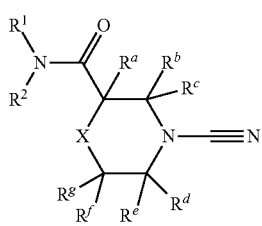

(I)

a tautomer thereof, or a pharmaceutically acceptable salt of said compound or tautomer, wherein:
X is O;
$R^a$ is selected from hydrogen and $C_1$-$C_3$ alkyl;
$R^b$, $R^c$, $R^d$, and $R^{ef}$ are each independently selected from hydrogen and $C_1$-$C_3$ alkyl;
$R^f$ and $R^g$ are each independently selected from hydrogen, fluoro, cyano and $C_1$-$C_3$ alkyl;
$R^1$ is selected from hydrogen and $C_1$-$C_3$ alkyl;
$R^2$ is selected from a 5 to 10 membered, monocyclic or bicyclic, optionally substituted heteroaryl or aryl ring, and a 3 to 10 membered, monocyclic or bicyclic, substituted heterocyclyl ring; or
$R^1$ and $R^2$ together form a 9 to 10 membered, bicyclic, optionally substituted heteroaryl ring;
wherein $R^2$, or the ring formed by $R^1$ together with $R^2$, when substituted, is substituted with one, two or three -$Q^1(R^3)_n$ which may be the same or different, wherein:
n is 0 or 1;
$Q^1$ represents $Q^{1a}$ or $Q^{1b}$; wherein
$Q^{1a}$ is selected from halo, cyano, nitro, hydroxyl, —$SR^4$, —$NR^4R^5$, —$CONR^4R^5$, —$C_0$-$C_3$-alkylene-$NR^4COR^5$, —$NR^4CONR^5R^6$, —$COR^4$, —$C(O)OR^4$, —$SO_2R^4$, —$SO_2NR^4R^5$, —$NR^4SO_2R^5$, —$NR^4SO_2NR^5R^6$, —$NR^4C(O)OR^5$, —$C_1$-$C_6$ alkyl, $C_1$-$C_6$ alkoxy, and —$C_2$-$C_6$ alkenyl;
$Q^{1b}$ is selected from a covalent bond, an oxygen atom, a sulfur atom, —$OR^7$—, —SO—, —$SO_2$—, —CO—, —C(O)O— and —$C_0$-$C_3$-alkylene-$NR^4$—$C_0$-$C_3$ alkylene;
$R^3$ is a 3 to 10 membered monocyclic or bicyclic heterocyclyl, heteroaryl, cycloalkyl or aryl ring;
$R^4$, $R^5$ and $R^6$ are each independently selected from hydrogen and optionally substituted $C_1$-$C_6$ alkyl;
$R^7$ is optionally substituted $C_1$-$C_6$ alkylene;
wherein $R^3$ is optionally substituted with one to four substituents independently selected from halo, cyano, oxo, nitro, hydroxyl, —$SR^8$, —$C_1$-$C_6$ alkyl, —$C_1$-$C_6$ alkoxy, —$C_2$-$C_6$ alkenyl, —$C_2$-$C_6$ alkynyl, -$Q^{2a}$-$R^{11}$, -$Q^{2a}$-$NR^8CONR^9R^{10}$, -$Q^{2a}$-$NR^8R^9$, -$Q^{2a}$-$COR^8$, -$Q^{2a}$-$NR^8COR^9$, -$Q^{2a}$-$NR^8C(O)OR^9$, -$Q^{2a}$-$SO_2R^8$, $Q^{2a}$-$CONR^8R^9$, -$Q^{2a}$-$CO_2R^8$, -$Q^{2a}$-$SO_2NR^8R^9$, -$Q^{2a}$-$NR^8SO_2R^9$ and -$Q^{2a}$-$NR^8SO_2NR^9R^{10}$; wherein said alkyl and alkoxy groups are optionally substituted by one or more halo;
wherein $Q^{2a}$ represents a covalent bond;
$R^8$, $R^9$ and $R^{10}$ are each independently selected from hydrogen and $C_1$-$C_6$ alkyl; and
$R^{11}$ is 5 to 10 membered heteroaryl; and
each heteroaryl or heterocyclyl ring comprises one to five heteroatoms independently selected from nitrogen, oxygen and sulfur.
2. A compound according to claim 1, wherein the ring of $R^2$ is selected from:
a 5 or 6-membered monocyclic heteroaryl, or a 9 or 10-membered bicyclic heteroaryl ring, each comprising one to three, heteroatoms independently selected from nitrogen, oxygen and sulfur;
an aryl selected from phenyl, indanyl, tetralinyl, and naphthyl; and
a 4, 5, 6 or 7-membered monocyclic heterocyclyl, or a 9 or 10-membered bicyclic heterocyclyl ring, each comprising one to three heteroatoms independently selected from nitrogen, oxygen and sulfur.
3. A compound according to claim 2, wherein the ring of $R^2$ is selected from pyridinyl, thiazolyl, thiadiazolyl, isoquinolinyl, phenyl, isoxazolyl, benzothiazolyl, pyrimidinyl, imidazolyl, pyrazolyl, pyridazinyl, pyrrolidinyl, pyrazinyl, and oxazolyl.
4. A compound according to claim 1, wherein the ring formed by $R^1$ together with $R^2$ is a 9 or 10-membered bicyclic heteroaryl ring, each comprising one to five heteroatoms independently selected from nitrogen, oxygen and sulfur, at least one of which is nitrogen.
5. A compound according to claim 4, wherein the ring formed by $R^1$ together with $R^2$ is a dihydropyrrolopyridinyl ring.

6. A compound according to claim 1, wherein $R^2$, or the ring formed by $R^1$ together with $R^2$, is substituted with one or two $R^3$ groups, each independently selected; and wherein $R^2$, or the ring formed by $R^1$ together with $R^2$, is optionally further substituted with one to four $Q^{1a}$ groups, each independently selected from halo, cyano, $C_1$-$C_3$ alkyl and $C_1$-$C_3$ alkoxy.

7. A compound according to claim 1, wherein, when $R^2$ is a heteroaryl or aryl ring, or $R^1$ and $R^2$ together form heteroaryl ring, said ring is optionally substituted with one to four $Q^{1a}$ groups, each independently selected from halo, cyano, $C_1$-$C_3$ alkyl and $C_1$-$C_3$ alkoxy.

8. A compound according to claim 1, wherein each $R^3$ is independently selected from an optionally substituted 3 to 10 membered, monocyclic or bicyclic, heterocyclyl, heteroaryl, cycloalkyl or aryl ring; and wherein each heteroaryl or heterocyclyl ring comprises one to three heteroatoms independently selected from nitrogen, oxygen and sulfur.

9. A compound according to claim 8, wherein each $R^3$ is independently selected from an optionally substituted phenyl, pyridinyl, pyrazinyl, pyrazolyl, indazolyl, and pyrazolopyridinyl ring.

10. A compound according to claim 8, wherein each $R^3$ is optionally substituted with one to four groups, each independently selected from halo, cyano, oxo, nitro, hydroxyl, $C_1$-$C_6$ alkyl, $C_1$-$C_6$ alkoxy, and $CONR^8R^9$;

$R^8$ and $R^9$ are each independently selected from hydrogen and $C_1$-$C_3$ alkyl; and said alkyl and alkoxy groups are optionally substituted by one or more halo.

11. A compound according to claim 10, wherein each $R^3$ is optionally substituted with one to four groups, each independently selected from fluoro, chloro, cyano, methyl, methoxy, isopropoxy, trifluoromethyl, trifluoromethoxy, and $CONH_2$.

12. A compound, which is selected from:
(R)-4-cyano-N-(4-phenylpyridin-2-yl)morpholine-2-carboxamide;
4-cyano-N-(5-(4-fluorophenyl)thiazol-2-yl)morpholine-2-carboxamide;
4-cyano-N-(3-propoxy-4-(1H-pyrazol-5-yl)phenyl)morpholine-2-carboxamide;
(R)-4-cyano-N-(6-(3-cyanophenyl)pyrimidin-4-yl)morpholine-2-carboxamide;
4-cyano-N-(4-(1-methyl-1H-pyrazol-4-yl)phenyl)morpholine-2-carboxamide;
(S)-2-(5-phenyl-2,3-dihydro-1H-pyrrolo[2,3-b]pyridine-1-carbonyl)morpholine-4-carbonitrile;
N-(6-(1H-pyrazol-4-yl)benzo[d]thiazol-2-yl)-4-cyanomorpholine-2-carboxamide;
4-cyano-N-(1-phenyl-1H-imidazol-4-yl)morpholine-2-carboxamide;
N-([1,1'-biphenyl]-4-yl)-4-cyanomorpholine-2-carboxamide;
4-cyano-N-(3-(3-methoxyphenyl)isoxazol-5-yl)morpholine-2-carboxamide;
4-cyano-N-(5-phenyl-1H-pyrazol-3-yl)morpholine-2-carboxamide;
4-cyano-N-(5-phenylpyridin-2-yl)morpholine-2-carboxamide;
4-cyano-N-(5-phenylisoxazol-3-yl)morpholine-2-carboxamide;
4-cyano-N-(4-cyano-[2,4'-bipyridin]-2'-yl)morpholine-2-carboxamide;
N-([1,1'-biphenyl]-3-yl)-4-cyanomorpholine-2-carboxamide;
4-cyano-N-(3-(1-methyl-1H-pyrazol-4-yl)phenyl)morpholine-2-carboxamide;
4-cyano-N-(6-phenylpyridin-3-yl)morpholine-2-carboxamide;
4-cyano-N-(2'-cyano-[4,4'-bipyridin]-2-yl)morpholine-2-carboxamide;
4-cyano-N-(3-(3-(trifluoromethyl)phenyl)isoxazol-5-yl)morpholine-2-carboxamide;
(R)-4-cyano-N-(5-phenylthiazol-2-yl)morpholine-2-carboxamide;
(R)—N-(6-(3-chlorophenyl)pyrimidin-4-yl)-4-cyano-morpholine-2-carboxamide;
(R)-4-cyano-N-(6-(3-methoxyphenyl)pyrimidin-4-yl)morpholine-2-carboxamide;
(R)-4-cyano-N-(6-(3-isopropoxyphenyl)pyrimidin-4-yl)morpholine-2-carboxamide;
(R)-4-cyano-N-(6-(3-cyano-5-fluorophenyl)pyrimidin-4-yl)morpholine-2-carboxamide;
(R)-4-cyano-N-(6-(4-cyanophenyl)pyrimidin-4-yl)morpholine-2-carboxamide;
(R)—N-(6-(4-chlorophenyl)pyrimidin-4-yl)-4-cyano-morpholine-2-carboxamide;
(R)—N-(6-(3-carbamoylphenyl)pyrimidin-4-yl)-4-cyanomorpholine-2-carboxamide;
(R)-4-cyano-N-(2-phenylthiazol-5-yl)morpholine-2-carboxamide;
(R)—N-(5-(1H-pyrazol-5-yl)pyridin-2-yl)-4-cyanomorpholine-2-carboxamide;
(R)—N-(6-(1H-indazol-4-yl)pyrimidin-4-yl)-4-cyano-morpholine-2-carboxamide;
(R)—N-(6-(1H-pyrazol-4-yl)isoquinolin-3-yl)-4-cyano-morpholine-2-carboxamide;
(R)-4-cyano-N-(5-phenyl-1,3,4-thiadiazol-2-yl)morpholine-2-carboxamide;
(S)-4-cyano-N-(5-phenylthiazol-2-yl)morpholine-2-carboxamide;
(S)-4-cyano-N-(isoquinolin-3-yl)morpholine-2-carboxamide;
(S)-4-cyano-N-(4-phenylpyridin-2-yl)morpholine-2-carboxamide;
1-cyano-N-(3-propoxy-4-(1H-pyrazol-5-yl)phenyl)piperidine-3-carboxamide;
1-cyano-N-(1-phenyl-1H-imidazol-4-yl)piperidine-3-carboxamide;
1-cyano-N-(5-phenyl-1H-pyrazol-3-yl)piperidine-3-carboxamide;
1-cyano-N-(5-phenylpyridin-2-yl)piperidine-3-carboxamide;
1-cyano-N-(4-phenylpyridin-2-yl)piperidine-3-carboxamide;
1-cyano-N-(3-phenylisoxazol-5-yl)piperidine-3-carboxamide;
1-cyano-3-fluoro-N-(5-phenylthiazol-2-yl)piperidine-3-carboxamide;
1-cyano-3-fluoro-N-(1-phenyl-1H-imidazol-4-yl)piperidine-3-carboxamide;
1-cyano-3-fluoro-N-(4-phenylpyridin-2-yl)piperidine-3-carboxamide;
1-cyano-3-fluoro-N-(5-phenylisoxazol-3-yl)piperidine-3-carboxamide;
1-cyano-N-(6-(3-cyanophenyl)pyrimidin-4-yl)-3-fluoropiperidine-3-carboxamide;
1-cyano-N-(4-(3-cyanophenyl)pyridin-2-yl)-3-fluoropiperidine-3-carboxamide;
1-cyano-3-fluoro-N-(5-phenyl-1,3,4-thiadiazol-2-yl)piperidine-3-carboxamide;

N-(5-(1H-pyrazol-5-yl)pyridin-2-yl)-1-cyano-3-fluoropiperidine-3-carboxamide;
N-(6-(1H-pyrazol-4-yl)benzo[d]thiazol-2-yl)-1-cyano-3-fluoropiperidine-3-carboxamide;
(R)-4-cyano-N-(3-(3-(trifluoromethyl)phenyl)isoxazol-5-yl)morpholine-2-carboxamide;
1-cyano-N-(4-(3-cyanophenyl)pyridin-2-yl)-3-fluoropiperidine-3-carboxamide;
(R)-4-cyano-N-(4-(3-cyanophenyl)pyridin-2-yl)morpholine-2-carboxamide;
(S)-4-cyano-N-(4-(3-cyanophenyl)pyridin-2-yl)morpholine-2-carboxamide;
(R)-1-cyano-N-(5-phenylthiazol-2-yl)piperidine-3-carboxamide;
(S)-1-cyano-N-(5-phenylthiazol-2-yl)piperidine-3-carboxamide;
(S)-1-cyano-N-(4-(3-cyanophenyl)pyridin-2-yl)piperidine-3-carboxamide;
1-cyano-5,5-difluoro-N-(1-phenyl-1H-imidazol-4-yl)piperidine-3-carboxamide;
N-(6-(1H-pyrazol-4-yl)benzo[d]thiazol-2-yl)-1-cyano-5,5-difluoropiperidine-3-carboxamide;
(2R,5*)-4-cyano-N-(6-(3-cyanophenyl)pyrimidin-4-yl)-5-methylmorpholine-2-carboxamide;
(R)—N-(6-(3-(1H-pyrazol-4-yl)phenyl)pyrimidin-4-yl)-4-cyanomorpholine-2-carboxamide;
(R)—N-(5-(3-chlorophenyl)pyridazin-3-yl)-4-cyanomorpholine-2-carboxamide;
(R)-4-cyano-N-(5-(3-cyanophenyl)pyridazin-3-yl)morpholine-2-carboxamide;
1-cyano-N-(5-(3-cyanophenyl)isoxazol-3-yl)-3-fluoropiperidine-3-carboxamide;
(R)-4-cyano-N-(6-cyanoisoquinolin-3-yl)morpholine-2-carboxamide;
(2R)-4-cyano-N-(1-(4-cyanopyridin-2-yl)pyrrolidin-3-yl)morpholine-2-carboxamide;
(S)-4-cyano-1-methyl-N-(5-phenylthiazol-2-yl)piperazine-2-carboxamide;
(R)-4-cyano-1-methyl-N-(5-phenylthiazol-2-yl)piperazine-2-carboxamide;
4-cyano-1-phenyl-N-(5-phenylthiazol-2-yl)piperazine-2-carboxamide;
1-acetyl-4-cyano-N-(5-phenylthiazol-2-yl)piperazine-2-carboxamide; and
4-cyano-1-(methylsulfonyl)-N-(5-phenylthiazol-2-yl)piperazine-2-carboxamide;
(R)—N-(5-(1H-pyrazol-5-yl)pyridin-2-yl)-1-cyano-3-fluoropiperidine-3-carboxamide;
1-cyano-N-(3-(3-cyanophenyl)isoxazol-5-yl)-3-fluoropiperidine-3-carboxamide;
(R)—N-(5-(3-chlorophenyl)isoxazol-3-yl)-1-cyano-3-fluoropiperidine-3-carboxamide;
(R)-1-cyano-3-fluoro-N-(5-(3-(trifluoromethyl)phenyl)isoxazol-3-yl)piperidine-3-carboxamide;
(R)—N-(3-(3-chlorophenyl)isoxazol-5-yl)-1-cyano-3-fluoropiperidine-3-carboxamide;
(R)—N-(5-(1H-pyrazol-1-yl)pyridin-2-yl)-1-cyano-3-fluoropiperidine-3-carboxamide;
(R)-1-cyano-N-(4-(3-cyanophenyl)oxazol-2-yl)-3-fluoropiperidine-3-carboxamide;
(R)-1-cyano-N-(1-(3-cyanophenyl)-1H-imidazol-4-yl)-3-fluoropiperidine-3-carboxamide;
1-cyano-3-fluoro-N-(1-(3-(trifluoromethyl)phenyl)-1H-imidazol-4-yl)piperidine-3-carboxamide;
1-cyano-3-fluoro-N-(1-(3-(trifluoromethoxy)phenyl)-1H-imidazol-4-yl)piperidine-3-carboxamide;
(R)-1-cyano-N-(1-(3-cyanophenyl)-1H-1,2,3-triazol-4-yl)-3-fluoropiperidine-3-carboxamide;
(R)-1-cyano-N-(1-(3-cyanophenyl)-1H-1,2,4-triazol-3-yl)-3-fluoropiperidine-3-carboxamide;
(R)—N-(5-(1H-indazol-7-yl)pyridin-2-yl)-1-cyano-3-fluoropiperidine-3-carboxamide;
(R)—N-(5-(1H-indazol-4-yl)pyridin-2-yl)-1-cyano-3-fluoropiperidine-3-carboxamide;
(R)—N-(5-(1H-indazol-7-yl)pyrazin-2-yl)-1-cyano-3-fluoropiperidine-3-carboxamide;
(R)—N-(5-(1H-indazol-4-yl)pyrazin-2-yl)-1-cyano-3-fluoropiperidine-3-carboxamide;
(R)—N-(6-(1H-indazol-7-yl)pyridazin-3-yl)-1-cyano-3-fluoropiperidine-3-carboxamide;
(R)—N-(5-(1H-pyrazolo[3,4-c]pyridin-7-yl)pyridin-2-yl)-1-cyano-3-fluoropiperidine-3-carboxamide;
(R)—N-(5-(1H-pyrazolo[4,3-b]pyridin-7-yl)pyridin-2-yl)-1-cyano-3-fluoropiperidine-3-carboxamide;
(R)—N-(6-(1H-indazol-4-yl)pyridazin-3-yl)-1-cyano-3-fluoropiperidine-3-carboxamide; and
(R)—N-(5-(1H-indazol-7-yl)pyrimidin-2-yl)-1-cyano-3-fluoropiperidine-3-carboxamide;

or a tautomer thereof, or a pharmaceutically acceptable salt of said compound or tautomer.

13. A pharmaceutical composition, comprising a compound according to claim 1, or a tautomer thereof or a pharmaceutically acceptable salt of said compound or tautomer, together with a pharmaceutically acceptable diluent or carrier.

14. A pharmaceutical composition, comprising a compound according to claim 12, or a tautomer thereof or a pharmaceutically acceptable salt of said compound or tautomer, together with a pharmaceutically acceptable diluent or carrier.

\* \* \* \* \*